United States Patent
Baughman et al.

(10) Patent No.: US 10,160,811 B2
(45) Date of Patent: *Dec. 25, 2018

(54) TREATMENT WITH ANTI-ERBB2 ANTIBODIES

(71) Applicant: GENENTECH, INC., South San Francisco, CA (US)

(72) Inventors: Sharon A. Baughman, Ventura, CA (US); Steven Shak, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 843 days.

This patent is subject to a terminal disclaimer.

(21) Appl. No.: 14/073,659

(22) Filed: Nov. 6, 2013

(65) Prior Publication Data

US 2014/0079692 A1     Mar. 20, 2014

Related U.S. Application Data

(60) Continuation of application No. 13/415,271, filed on Mar. 8, 2012, now abandoned, which is a continuation of application No. 13/167,599, filed on Jun. 23, 2011, now abandoned, which is a continuation of application No. 11/443,943, filed on May 31, 2006, now abandoned, which is a division of application No. 10/600,152, filed on Jun. 20, 2003, now Pat. No. 7,371,379, which is a division of application No. 09/648,067, filed on Aug. 25, 2000, now Pat. No. 6,627,196.

(60) Provisional application No. 60/213,822, filed on Jun. 23, 2000, provisional application No. 60/151,018, filed on Aug. 27, 1999.

(51) Int. Cl.
| | |
|---|---|
| *C07K 16/30* | (2006.01) |
| *A61K 39/395* | (2006.01) |
| *C07K 16/32* | (2006.01) |
| *A61K 45/06* | (2006.01) |
| *A61K 31/337* | (2006.01) |
| *A61K 39/00* | (2006.01) |
| *A61K 38/00* | (2006.01) |

(52) U.S. Cl.
CPC .......... *C07K 16/30* (2013.01); *A61K 31/337* (2013.01); *A61K 39/395* (2013.01); *A61K 39/39558* (2013.01); *A61K 45/06* (2013.01); *C07K 16/32* (2013.01); *A61K 38/00* (2013.01); *A61K 2039/505* (2013.01); *A61K 2039/54* (2013.01); *A61K 2039/545* (2013.01)

(58) Field of Classification Search
CPC .............................................. A61K 47/48384
See application file for complete search history.

(56) References Cited

U.S. PATENT DOCUMENTS

| | | |
|---|---|---|
| 4,676,980 A | 6/1987 | Segal et al. |
| 4,753,894 A | 6/1988 | Frankel et al. |
| 4,816,567 A | 3/1989 | Cabilly et al. |
| 4,935,341 A | 6/1990 | Bargmann et al. |
| 4,943,533 A | 7/1990 | Mendelsohn et al. |
| 4,968,603 A | 11/1990 | Slamon et al. |
| 4,975,278 A | 12/1990 | Senter et al. |
| 5,169,774 A | 12/1992 | Frankel et al. |
| 5,183,884 A | 2/1993 | Kraus et al. |
| 5,288,477 A | 2/1994 | Bacus |
| 5,359,046 A | 10/1994 | Capon et al. |
| 5,367,060 A | 11/1994 | Vandlen et al. |
| 5,401,638 A | 3/1995 | Carney et al. |
| 5,464,751 A | 11/1995 | Greene et al. |
| 5,480,968 A | 1/1996 | Kraus et al. |
| 5,578,482 A | 11/1996 | Lippman et al. |
| 5,604,107 A | 2/1997 | Carney et al. |
| 5,641,869 A | 6/1997 | Vandlen et al. |
| 5,663,144 A | 9/1997 | Greene et al. |
| 5,677,171 A | 10/1997 | Hudziak et al. |
| 5,705,157 A | 1/1998 | Greene |
| 5,720,937 A | 2/1998 | Hudziak et al. |
| 5,720,954 A | 2/1998 | Hudziak et al. |
| 5,725,856 A | 3/1998 | Hudziak et al. |
| 5,726,023 A | 3/1998 | Cheever et al. |
| 5,728,687 A | 3/1998 | Bissery |
| 5,747,261 A | 5/1998 | King et al. |
| 5,770,195 A | 6/1998 | Hudziak et al. |
| 5,772,997 A | 6/1998 | Hudziak et al. |
| 5,776,427 A | 7/1998 | Thorpe et al. |
| 5,783,186 A | 7/1998 | Arakawa et al. |
| 5,801,005 A | 9/1998 | Cheever et al. |
| 5,821,337 A | 10/1998 | Carter et al. |
| 5,824,311 A | 10/1998 | Greene et al. |
| 5,834,229 A | 11/1998 | Vandlen et al. |
| 5,837,243 A | 11/1998 | Deo et al. |
| 5,837,523 A | 11/1998 | Greene et al. |
| 5,840,525 A | 11/1998 | Vandlen et al. |
| 5,846,538 A | 12/1998 | Cheever et al. |
| 5,856,110 A | 1/1999 | Vandlen et al. |
| 5,859,206 A | 1/1999 | Vandlen et al. |
| 5,869,445 A | 2/1999 | Cheever et al. |
| 5,876,712 A | 3/1999 | Cheever et al. |
| 5,877,305 A | 3/1999 | Huston et al. |

(Continued)

FOREIGN PATENT DOCUMENTS

| | | |
|---|---|---|
| EP | 0003089 A1 | 7/1979 |
| EP | 0 599 274 A1 | 6/1994 |

(Continued)

OTHER PUBLICATIONS

Krop, I.E., et al. J. Clin. Oncol., 28: 2698-2704, 2010.*

(Continued)

*Primary Examiner* — Ilia I Ouspenski
(74) *Attorney, Agent, or Firm* — Diane L. Marschang; Ginger R. Dreger

(57) ABSTRACT

The present invention concerns dosages for treatment of human cancer patients with an anti-Epidermal Growth Factor Receptor (EGFR) antibody.

12 Claims, 5 Drawing Sheets

Specification includes a Sequence Listing.

(56) References Cited

U.S. PATENT DOCUMENTS

| | | | |
|---|---|---|---|
| 5,908,835 A | 6/1999 | Bissery | |
| 5,910,486 A | 6/1999 | Curiel et al. | |
| 5,922,845 A | 7/1999 | Deo et al. | |
| 5,939,531 A | 8/1999 | Wels et al. | |
| 5,949,245 A | 9/1999 | Liu | |
| 5,968,511 A | 10/1999 | Akita et al. | |
| 5,977,322 A | 11/1999 | Marks et al. | |
| 5,985,553 A | 11/1999 | King et al. | |
| 6,015,567 A | 1/2000 | Hudziak et al. | |
| 6,028,059 A | 2/2000 | Curiel et al. | |
| 6,054,297 A | 4/2000 | Carter et al. | |
| 6,054,561 A | 4/2000 | Ring et al. | |
| 6,096,873 A | 8/2000 | Schaefer et al. | |
| 6,123,939 A | 9/2000 | Shawver et al. | |
| 6,165,464 A | 12/2000 | Hudziak et al. | |
| 6,267,958 B1 | 7/2001 | Andya et al. | |
| 6,333,348 B1 | 12/2001 | Vogel et al. | |
| 6,365,345 B1 | 4/2002 | Biysch et al. | |
| 6,627,196 B1 | 9/2003 | Baughman et al. | |
| 6,949,245 B1 | 9/2005 | Sliwkowski | |
| 7,371,379 B2 | 5/2008 | Baughman et al. | |
| 2002/0132239 A1* | 9/2002 | Lovell-Badge | C12N 5/0623 435/5 |
| 2003/0086924 A1 | 5/2003 | Sliwkowski | |
| 2003/0170243 A1* | 9/2003 | Stern | C07K 16/40 424/146.1 |
| 2004/0013667 A1 | 1/2004 | Kelsey et al. | |
| 2004/0037824 A1 | 2/2004 | Baughman et al. | |
| 2005/0208043 A1 | 9/2005 | Adams et al. | |
| 2005/0238640 A1 | 10/2005 | Sliwkowski | |
| 2006/0034842 A1 | 2/2006 | Adams et al. | |
| 2006/0073143 A1 | 4/2006 | Adams et al. | |
| 2006/0193854 A1 | 8/2006 | Adams et al. | |
| 2006/0198843 A1 | 9/2006 | Adams et al. | |
| 2006/0210561 A1 | 9/2006 | Baughman et al. | |
| 2006/0216285 A1 | 9/2006 | Adams et al. | |
| 2010/0183645 A1* | 7/2010 | Barbeito | C07K 14/475 424/185.1 |

FOREIGN PATENT DOCUMENTS

| | | |
|---|---|---|
| EP | 0 612 812 B1 | 9/1994 |
| EP | 0 711 565 | 8/1998 |
| EP | 1 210 115 B1 | 8/2009 |
| JP | 3-240498 | 10/1991 |
| JP | 5-117165 | 5/1993 |
| JP | 5-170667 | 7/1993 |
| JP | 5-213775 | 8/1993 |
| JP | 5-317084 | 12/1993 |
| JP | 95006982 B2 | 1/1995 |
| JP | 7-59588 | 3/1995 |
| JP | 2761543 B2 | 6/1998 |
| JP | 2895105 | 5/1999 |
| WO | WO 89/06692 | 7/1989 |
| WO | WO 90/14357 | 11/1990 |
| WO | WO 91/00360 | 1/1991 |
| WO | WO 92/10573 | 6/1992 |
| WO | WO 92/20373 | 11/1992 |
| WO | WO 92/20798 | 11/1992 |
| WO | WO 93/12220 | 6/1993 |
| WO | WO 93/21232 | 10/1993 |
| WO | WO 93/21319 | 10/1993 |
| WO | WO 94/00136 | 1/1994 |
| WO | WO 94/04690 | 3/1994 |
| WO | WO 94/22478 | 10/1994 |
| WO | WO 94/28127 | 12/1994 |
| WO | WO 95/16051 | 6/1995 |
| WO | WO 1995/017507 | 6/1995 |
| WO | WO 95/28485 | 10/1995 |
| WO | WO 96/18409 | 6/1996 |
| WO | WO 96/27011 | 9/1996 |
| WO | WO 97/04801 | 2/1997 |
| WO | WO 97/20858 | 6/1997 |
| WO | WO 97/27848 | 8/1997 |
| WO | WO 97/35885 | 10/1997 |
| WO | WO 97/38731 | 10/1997 |
| WO | WO 98/02541 | 1/1998 |
| WO | WO 98/17797 | 4/1998 |
| WO | WO 98/45479 | 10/1998 |
| WO | WO 99/31140 | 6/1999 |
| WO | WO 99/48527 | 9/1999 |
| WO | WO 00/61185 A1 | 10/2000 |
| WO | WO 01/00245 A2 | 1/2001 |

OTHER PUBLICATIONS

Herceptin® (Trastuzumab), Sep. 1998, © 1998 Genentech, Inc.*
Smith, D.A., et al, Pharmacokinetics and Metabolism in Drug Design, Third Edition. Wiley-VCH Verlag GmbH & Co. KGaA, 2012; Chapter 2, Pharmacokinetics, pp. 19-40.*
Chapman et al. Nature Biotechnology (1999) 17: 780-783.*
Hudson et al. Current Opinion in Immunology (1999) 11: 548-557.*
Hyden et al. Current Opinion in Immunology (1997) 9: 201-212.*
Velders et al. British Journal of Cancer (1998) 78(4): 478-483.*
Mourad et al. Transplantation (1998) 65(5): 632-641.*
Wright et al. Trends Biotechnol. (1997) 15(1): 26-32.*
FDA Approved Label for Herceptin® (1998), 2 pages.*
Pegram, et al. Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. J. Clin. Oncol. (1998) 16: 2659-2671.*
Baselga et al. Phase II study of weekly intravenous recombinant humanized anti-p185HER2 monoclonal antibody in patients with HER2/neu-overexpressing metastatic breast cancer. J. Clin. Oncol. (1996) 14: 737-744.*
Watanabe et al. Pharmacokinetically Guided Dose Escalation Study of Anti-HER2 Monoclonal Antibody in Patients with HER2/NEU-Overexpressing Metastatic Breast Cancer. J. Clin. Oncol. (1998) 17: 182a, Abstract No. 702. 5 pages.*
Merriam-Webster Dictionary (accessed online at "https://www.merriam-webster.com/dictionary/amount" on Jun. 30, 2018. 1 page.*
Slamon et al. Addition of Herceptin® (Humanized Anti-HER2 Antibody) to First Line Chemotherapy for HER2 Overexpressing Metastatic Breast Cancer (HER2+/MBC) Markedly Increases Anti-cancer Activity: A Randomized Multinational Controlled Phase III Trial. J. Clin. Oncol. (1998) 17: 98a, Abstract No. 377. 5 pages.*
Cobleigh et al. Efficacy and Safety of Herceptin® (Humanized anti-H ER2 Antibody) as a Single Agent in 222 Women with HER2 Overexpression Who Relapsed Following Chemotherapy for Metastatic Breast Cancer. Proceedings of ASCO (1998) vol. 17, p. 97a, Abstract No. 276. 1 page.*
Goldenberg M. Trastuzumab, a recombinant DNA-derived humanized monoclonal antibody, a novel agent for the treatment of metastatic breast cancer. Clin Ther. (1999) 21(2): 309-318.*
Cobleigh et al. Multinational Study or the Efficacy and Safety of Humanized Anti-HER2 Monoclonal Antibody in Women Who Have HER2-Overexpressing Metastatic Breast Cancer That Has Progressed After Chemotherapy for Metastatic Disease. J. Clin. Oncol. (1999) 17: 2639-2648.*
Shak S. Overview of the Trastuzumab (Herceptin) Anti-HER2 Monoclonal Antibody Clinical Program in HER2-Overexpressing Metastatic Breast Cancer. Semin. Oncol. (1999) 26(suppl. 12): 71-77.*
Vogel et al. Efficacy and Safety of HerceptinTM (Trastuzumab, Humanized Anti-HER2 Antibody) as a Single Agent in First-Line Treatment of HER2 Overexpressing Metastatic Breast Cancer (HER2+/MBC). Breast Cancer Research and Treatment (1998) vol. 50(3), p. 232, Abstract No. 23 (4 pages).*
Watanabe et al. Phase I clinical trial results of anti-H ER2 monoclonal antibody (MKC-454) to HER2/neu overexpressing metastatic breast cancer. 6th Annual Meeting of the Japanese Breast Cancer Society—Program and Proceedings (1998) English translation, 3 pages.*
Perry and Wiseman "Trastuzumab", BioDrugs 12(2):129-135, Aug. 1, 1999.

(56) References Cited

OTHER PUBLICATIONS

Cobliegh and Frame, "Is Trastuzumab Every Three Weeks Ready for Prime Time?" J. Clinical Oncology, vol. 21, No. 21, 2003, pp. 3900-3901.
Anderson, V. et al., Proceedings of the American Association for Cancer Research, 39: p. 523, Abstract No. 3561, 1998.
Arteaga at al., "p195c-ernb-2 Signaling Enhances Cisplatin-induced Cytotoxicity in Human Breast Carcinoma Cells: Association Between an Oncogenic Receptor Tyrosine Kinase and Drug-induced DNA Repair" Cancer Research 54(14): 3758-3765, (Jul. 15, 1994).
Bacus et al., "Differentiation of Cultured Human Breast Cancer Cells (AU-565 and MCF-7) Associated With Loss of Cell Surface HER-2/neu Antigen" Molecular Carcinogenesis 3(6):350-362, (1990).
Bacus et al., "Tumor-inhibitory Monoclonal Antibodies to the HER-2/Neu Receptor Induce Differentiation of Human Breast Cancer Cells" Cancer Research 52(9): 2580-2589, (May 1, 1992).
Balsega, et al., "Phase II study of weekly intravenous recombinant humanized anti-p185$^{HER2}$ monoclonal antibody in patients with HER2/neu-overexpressing metastic breast cancer", Journal of Clinical Oncology, vol. 14, No. 3, pp. 737-744, (1996).
Baselga and Mendelsohn, "Receptor Blockade With Monoclonal Antibodies as Anti-Cancer Therapy" Pharmac. Ther. 64: 127-154, (1994).
Baselga at al., "Ongoing phase II study of intravenous recombinant human anti-p185 H monoclonal antibody 4D5 (MAb 405) in patients with stage IV breast cancer overexpressing HER2" Breast Cancer Research and Treatment (Abstract 8) 32(Suppl):30 (1994).
Balsega, et al., "Antitumor activity of paclitaxel in combination with anti-growth factor receptor monoclonal antibodies in breast cancer xenografts", Proceedings of the Annual Meeting of the American Association for Cancer Research 35 A2262, 380, (1994).
Baselga et al., "Anti HER2 Humanized Monoclonal Antibody (MAb) Alone and in Combination with Chemotherapy Against Human Breast Carcinoma Xenografts" Proceedings of ASCO—13th Annual Meeting (Abstract #53), Dallas, TX 13:63 (Mar 1994).
Baselga et al., "Antitumor activity of paclitaxel in combination with anti-growth factor receptor monoclonal antibodies in breast cancer xenografts" Proceedings of the American Association for Cancer Research (Abstract No. 2262), (1994).
Baselga et al., "HER2 Overexpression and Paclitaxel Sensitivity in Breast Cancer: Therapeutic Implications" Oncology (Supplement No. 2) 11(3): 43-48, (1997).
Baselga et al., "Monoclonal Antibodies Directed Against Growth Factor Receptors Enhance the Efficacy of Chemotherapeutic Agents." Annals of Oncology (abstract #010) 5 (Suppl. 5), (1994).
Baselga et al., "Phase II Study of Weekly Intravenous Recombinant Humanized Anti-p185HER$^2$ Monoclonal Antibody in Patients With HER2/neu-Overexpressing Metastatic Breast Cancer" J. Clin. Oncol. 14(3): 737-744, (Mar. 1996).
Baselga et al., "Recombinant Humanized Anti-HER2 Antibody (Herceptin) Enchances the Antitumor Activity of Paclitaxel and Doxorubicin against HER2/neu Overexpessing Human Breast Cancer Xenografts", Cancer Research 58: 2825-2831, (Jul. 1998).
Baselga, et al., Breast Cancer Research and Treatment, 32(suppl): p. 30, Abstract #5, (1994).
Baselga, J. et al. Journal of Clinical Oncology, 18(4): 904-914, 2000.
Baselga et al., "Phase II Study of Efficacy, Safety and Pharmacokinetics of Trastuzumab Monotherapy Administered on a 3-Weekly Schedule", *Journal of Clinical Oncology*, vol. 23, No. 7, (2005) pp. 2162-2171.
Bos, M. et al. Phase I studies of anti-epidermal growth factor receptor (EGFR) chimeric monoclonal antibody C225 in patients with EGFR overexpressing tumors. ASCO, 1996 ASCO Annual Meeting, Abstract No. 1381.
Carbonell Castellon et al., "Efficacy and safety of 3-weekly Herceptin (H) monotherapy in women with HER2-positive metastatic breast cancer (MBC): preliminary data from a phase II study" Proc Am Soc Clin Oncol (Abstract #73 from the 2002 ASCO Meeting) 21:19a (2002).
Carbonell et al., "Efficacy and safety of 3-weekly Herceptin monotherapy in women with HER2-positive metastatic breast cancer: preliminary data from a phase II study", (Oral presentation at the 38th Annual Meeting of the American Society of Clinical Oncology, May 18-21, 2002 in Orlando, Florida).
Carter et al., "Humanization of an Anti-p185HER$^2$ Antibody for Human Cancer Therapy" Proc. Natl. Acad. Sci. USA 89(10): 4285-4289, (May 1992).
Chothia and Lesk, "Canonical Structures for the Hypervariable Regions of Immunoglobulins" J. Mol. Biol. 196: 901-917, (1987).
Cobleigh et al., "Multinational study of the efficacy and safety of humanized anti-HER2 monoclonal antibody in women who have HER2-overexpressing metastatic breast cancer that has progressed after chemotherapy for metastatic disease" Journal of Clinical Oncology 17(9):2639-2648 (Sep. 1999).
De Santes et al., "Radiolabeled Antibody Targeting of the HER-2/neu Oncoprotein" Cancer Research 52: 1916-1923, (1992).
Di Fiore et al., "erbB-2 Is a Potent Oncogene When Overexpressed in NIH/3T3 Cells." Science, 237(4811):178-182, (Jul. 10, 1987).
Drebin at al., "Down-Modulation of an Oncogene Protein Product and Reversion of the Transformed Phenotype by Monoclonal Antibodies" Cell 41(3): 695-706, (1985).
Drebin et al., "Inhibition of Tumor Growth by a Monoclonal Antibody Reactive With an Oncogene-Encoded Tumor Antigen" Proc. Natl. Acad. Sci. 83: 9129-9133, (1986).
Drebin et al., "Monoclonal Antibodies Reactive With Distinct Domains of the neu Oncogene-Encoded Molecule Exert Synergistic Anti-Tumor Effects In Vivo" Oncogene p. 185 2: 273-277, (1988).
Drebin et al., "Monoclonal Antibodies Specific for the neu Oncogene Product Directly Mediate Anti-tumor Effects In Vivo" Oncogene 2(4): 387-394, (1988).
D'Souza and Taylor-Papadimitriou., "Overexpression of ERBB2 in Human Mammary Epithelial Cells Signals Inhibition of Transcription of the E-Cadherin Gene" Proc. Natl. Acad. Sci. USA 91(15): 7202-7206, (1994).
Eisenhauer, et al., "The Taxoids", Drugs, vol. 55, pp. 5-30, (1998).
Fendly, B.M. et al., "Characterization of Murine Monoclonal Antibodies Reactive to Either the Human Epidermal Growth Factor Receptor or HER2/neu Gene Product" Cancer Research 50: 1550-1558, (1990).
Fleiss, JL Statistical Methods for Rates and Proportions, $2^{nd}$ edition, New York, NY:Wiley pp. 13-17, (1981).
Gelmon et al., "Pharmacokinetics and safety of Herceptin when administered every 3 weeks to women with metastatic breast cancer" (Oral presentation at the 37th Annual Meeting of the American Society of Clinical Oncology, May 12-15, 2001 in San Francisco, CA).
Gemzar (gemcitabine HCL), "Product Information—PDR" (2000).
Gibaldi et al., "Pharmacokinetics vol. 15" in *Pharmacokinetics* vol. 15, (1982), pp. 1-5; 15-43, 113-143 and 385-393.
Goldenberg, et al., "Trastuzumab, a recombinant DNA-derived humanized monoclonal anitbody, a novel agent for the treatment of metastatic breast cancer", Clinical Therapeutics, vol. 21, No. 2, pp. 309-318, (1999).
Goldenberg, M., "Trastuzumab, a Recombinant DNA-Derived Humanized Monoclonal Antibody, a Novel Agent for the Treatment of Metastatic Breast Cancer" Clinical Therapeutics 21(2):309-318, (1999).
Green et al., "Preclinical Evaluation of WR-151327: An Orally Active Chemotherapy Protector" Cancer Research 54(3):738-741, (1994).
Guy et al., "Expression of the neu Protooncogene in the Mammary Epithelium of Transgenic Mice Induces Metastatic Disease." Proc. Natl. Acad. Sci. USA 89(22): 10578-10582, (1992).
Hancock et al., "A Monoclonal Antibody Against the c-erbB-2 Protein Enhances the Cytotoxicity of cis-Diamminedichloroplatinum Against Human Breast and Ovarian Tumor Cell Lines" Cancer Research 51: 4575-4580, (Sep. 1, 1991).
Harris et al., "A population pharmacokinetic (PK) model for Herceptin (H) and implications for clinical dosing" (Oral presentation at the 38th Annual Meeting of the American Society of Clinical Oncology, May 18-21, 2002 in Orlando, Florida).

(56) References Cited

OTHER PUBLICATIONS

Harris et al., "A population pharmacokinetic (PK) model for trastuzumab (Herceptin) and implications for clinical dosing" Proc Am Soc Clin Oncol (Abstract #488) 21: 123a (2002).
Harwerth et al., "Monoclonal Antibodies Against the Extracellular Domain of the erbB-2 Receptor Function as Partial Ligand Agonists" Journal of Biological Chemistry 267(21): 15160-15167, (Jul. 25, 1992).
Hortobagyi, et al., "Recent progress in the clinical development of docetaxel (Taxotere)", Seminars in Oncology, vol. 26, No. 3, supply. 9, pp. 32-36, (1999).
Hudziak et al., "Increased Expression of the Putative Growth Factor Receptor p185HER$^2$ Causes Transformation and Tumorigenesis of NIH 3T3 Cells", Proc. Natl. Acad. Sci. USA 84(20): 7159-7163, (1987).
Hudziak et al., "p185HER4 Monoclonal Antibody Has. Antiproliferative Effects In Vitro and Sensitizes Human Breast Tumor Cells to Tumor. Necrosis Factor" Molecular & Cellular Biology 9(3): 1165-1172, (1989).
Hynes and Stern, "The Biology of erbB-2/neu/HER-2 and Its Role in Cancer" Biochimica et Biophysica Acta 1198(2-3): 165-184, (Dec. 30, 1994).
Ilgen et al., "Characterization of anti-HER/2 antibodies which inhibit the growth of breast tumor cells in vitro" Proceedings of the American Association for Cancer Research (abstract #3209) 37: 470 (Mar. 1996).
Jones et al., "Replacing the Complementarily-Determining Regions in a Human Antibody with Those From a Mouse" Nature 321: 522-525, (May 29, 1986).
Kasprzyk et al., "Therapy of an Animal Model of Human Gastric Cancer Using a Combination of Anti-erbB-2 Monoclonal Antibodies", Cancer Research 52(10): 2771-2776, (1992).
Kotts et al., "Differential Growth Inhibition of Human Carcinoma Cells Exposed to Monoclonal In Vitro Antibodies Directed against the Extracellular Domain of the HER2/ERBB2 Protooncogene" (Abstract #176) 6(3): 59A (1990).
Kumar et al., "Regulation of Phosphorylation of the c-erbB-2/HER2 Gene Product by a Monoclonal Antibody and Serum Growth Factor(s) in Human Mammary Carcinoma Cells" Molecular & Cellular Biology 11(2): 979-986, (1991).
Lewis et al., "Differential Responses of Human Tumor Cell Lines to Anti-p185HER$^2$ Monoclonal Antibodies" Cancer Immunol Immunother. 37:255-263, (1993).
Lewis et al., "Growth Regulation of Human Breast and Ovarian Tumor Cells by Heregulin: Evidence for the Requirement of ErbB2 as a Critical Component in Mediating Heregulin Responsiveness" Cancer Research 56: 1457-1465, (Mar. 15, 1996).
Leyland-Jones et al., "Pharmacokinetics of Herceptin administered with paclitaxel every three weeks" Breast Cancer Res Treat (abstract only) 64:124 (2000).
Maier et al., "Requirements for the Internalization of a Murine Monoclonal Antibody Directed against the HER-2/neu Gene Product c-erbB-2" Cancer Research 51(19): 5361-5369, (Oct. 1, 1991).
Masui et al., "Growth Inhibition of Human Tumor Cells in Athymic Mice by Anti-Epidermal Growth Factor Receptor Monoclonal Antibodies" Cancer Research 44(3): 1002-1007, (1984).
Masuko et al., "A murine Monoclonal Antibody That Recognizes an Extracellular Domain of the Human c-erbB-2 Protooncogene Product" Jpn J. Cancer Res. 80: 10-14, (1989).
McCann et al., "c-erbB-2 Oncoprotein Expression in Primary Human Tumors" Cancer 65(1):88-92, (1990).
McKenzie et al., "Generation and Characterization of Monoclonal Antibodies Specific for the Human neu Oncogene Product, p185" Oncogene 4: 543-548, (1989).
Mendelsohn et al., "Receptor Blockade and Chemotherapy: A New Approach to Combination Cancer Therapy." Annals of Oncology (abstract #040), 7(Suppl. 1): 22, (1996).
Myers et al., "Biological Effects of Monoclonal Antireceptor Antibodies Reactive with neu Oncogene Product, p185neu" Methods in Enzymology 198: 277-290, (1991).

Nakamura, G.R. et al., "Strain specificity and binding affinity requirements of neutralizing monoclonal antibodies to the C4 domain of gp120 from human immunodeficiency virus type 1" Journal of Virology 67(10): 6179-6191, (Oct. 1993)
Norton, L., "Evolving Concepts in the Systemic Drug Therapy of Breast Cancer." Seminars in Oncology 24(4 Suppl 10):S10-3-S10-10, (Aug. 1997).
Osterborg, A. et al., Br. J. Haematology, 93: 151-153, 1996.
Pedley, B., et al., Pharmacokinetics of monoclonal antibodies, Clin. immunother., 6(1): 54-67, (1996).
Pegram et al., "Inhibitory effects of combinations of HER-2/neu antibody and chemotherapeutic agents used for treatment of human breast cancers" Oncogene 18: 2241-2251, (1999).
Pegram et al., "Phase II study of receptor-enhanced chemosensitivity using recombinant humanized anti-p185HBR$^2$/nea monoclonal antibody plus cisplatin in patients with HER2/neu-overexpressing metastatic breast cancer refractory to chemotherapy treatment" Journal of Clin Oncol 16(8):2659-2671 (Aug. 1998).
Pegram et al., "Phase II Study of Receptor-Enhanced Chemosensitivity Using Recombinant Humanized Anti-p165HER2/nen Monoclonal Antibody Plus Cisplatin in Patients With HER2/neu-Overexpressing Metastatic Breast Cancer Refractory to Chemotherapy Treatment" Journal of Clinical Oncology 16(8): 2659-2671, (1998).
Perez-Soler, R. et al, Journal of Clinical Oncology, 12(4): 730-739, 1994.
Pictras et al., "Antibody to HER-2/neu Receptor Blocks DNA Repair After Cisplatin in Human Breast and Ovarian Cancer Cells" Oncogene 9: 1829-1838, (1994).
Presta et al., "Humanization of an Antibody Directed Against IgE", J. Immunol 151(5): 2623-2630, (1993).
Raefsky et al., "Phase II Trial of Docetaxel and Herceptin as First-or Second-Line Chemotherapy for Women with Metastatic Breast Cancer Whose Tumors Overexpress BER2" Proceedings of ASCO (Abstract #523) 18:137a, (1999).
Ravdin and Chamness, "The c-erbB-2 proto-oncogene as a prognostic and predictive marker in breast marker cancer: a paradigm for the development of other macromolecular—a review" Gene 159(1): 19-27, (1995).
Reilly, R., et al., "Problems of delivery of monoclonal antibodies", Clin. Pharmacokinet., 28(2): 126-142, (1995).
Renz, M.E. et al., "Structural requirements for adhesion of soluble recombinant murine vascular cell adhesion molecule-1 to a4131" Journal of Cell Biology 125(6): 1395-1406, (1994).
Riechmann et al., "Reshaping Human Antibodies for Therapy" Nature 332: 323-327, (1988).
Rodeck et al., "Interactions between growth factor receptors and corresponding monoclonal antibodies in human tumors" J. Cellular Biochem. 35(4): 315-320, (1987).
Rohan et al., "Immunohistochemical detection of c-erb3-2 and p53 in benign -breast disease and breast cancer risk" Journal of the National Cancer Institute 90(17): 1262-1269, (1998).
Sarup et al., "Characterization of an Anti-P185HER$^2$ Monoclonal Antibody that Stimulates Receptor Function and Inhibits Tumor Cell Growth" Growth Regulation 1: 72-82, (1991).
Schlereth, Bernd, et al., "Feasibility of repeated subcutaneous delivery supports a new route of administration for treating cancer patients with EpCAM-specific BiTE antibody MT110," 99th AACR Annual Meeting (Apr. 2008).
Schlom, J., "Monoclonal Antibodies: They're More and Less Than You Think" Molecular Foundations of Oncology, Broder, S. ed., Baltimore, MD:Williams & Wilkins, Chapter 6, pp. 95-134, (1991).
Scott et al., "p185HER$^2$ Signal Transduction in Breast Cancer Cells" Journal of Biological Chemistry 266(22): 14300-14305, (Aug. 5, 1991).
Seidman et al., "Memorial Sloan-Kettering Cancer Center experience with paclitaxel in the treatment of breast cancer" seminars in Oncology 22(5 Suppl 12): 108-116, (1995).
Seifert et al., "Dexrazoxane in the prevention of doxorubicin-induced cardiotoxicity" Annals of Pharmacotherapy 28(9):1063-1072, (Sep. 1994).

(56) References Cited

OTHER PUBLICATIONS

Semba et al., "A v-erbB-related protooncogene, c-erbB-2, is distinct from the c-erbB-1/epidermal growth factor-receptor gene:and is amplified in a human salivary gland adenocarcinoma" Proc. Natl. Acad. Sci. USA 82: 6497-6501, (1985).
Sharili, J., et al., "Improving monoclonal antibody pharmacokinetics via chemical modification", The quarterly journal of nuclear medicine, 42: 242-249, (1998).
Shawver et al., "Ligand-Like Effects Induced by Anti-c-erbB-2 ntibodies Do Not Correlate with and Are Not Required for Growth Inhibition of Human Carcinoma Cells" Cancer Research 54(5):1367-1373, (Mar. 1, 1994).
Shepard et al., "Monoclonal Antibody Therapy of Human Cancer: Taking the HER2 Protooncogene to the Clinic" J. Clin. Immunol 11(3): 117-127, (1991).
Sims et al., "A Humanized CD18 Antibody Can Block Function Without Cell Destruction" The Journal of Immunology 151(4): 2296-2308, (Aug. 15, 1993).
Singal and Iliskovic, "Doxorubicin-induced cardiomyopathy" New England J. of Medicine 339(13): 900-905, (1998).
Singal et al., "Combination therapy with probucol prevents adriamycin-induced cardiomyopathy" Journal of Molecular & Cellular Cardiology 27(4): 1055-1063, (Apr. 1995).
Slamon et al., "Human Breast Cancer: Correlation of Relapse and Survival with Amplification of the HER-2/neu Oncogene" Science 235: 177-182, (Jan. 9, 1987).
Slamon et al., "Studies of the HER-2/neu Proto-Oncogene in Human Breast and Ovarian Cancer" Science 244: 707-712, (May 12, 1989).
Slamon et al., "Use of chemotherapy plus a monoclonal antibody against HER2 for metastatic breast cancer that overexpresses HER2" New England J. of Medicine 344(11): 783-792, (2001).
Sliwkowski et al., "A humanized monoclonal antibody for the treatment of HER2 overexpressing breast cancer" Proceedings of the American Association for Cancer Research (abstract only) 37: 625-626, (Mar. 1996).
Sliwkowski et al., "Coexpression of erbB2 and erbB3 Proteins Reconstitutes a High Affinity Receptor for Heregulin" Journal of Biological Chemistry 269(20): 14661-14665, (1994).
Stancovski et al., "Mechanistic Aspects of the Opposing Effects of Monoclonal Antibodies to the ERBB2 Receptor on Tumor Growth" Proc. Natl. Acad. Sci. USA 88(19): 8691-8695, (1991).
Stegmaier, K., et al., Blood, 106(8): 2841-2848, (2005).
Stevenson et al., "A Chimeric Antibody With Dual Fc Regions (bisFabFc) Prepared by Manipulations at the IgG Hinge" Anti-Cancer Drug Design 3(4): 219-230,(1989).
Suresh et al., "Bispecific Monoclonal Antibodies from Hybrid Hybridomas" Methods in Enzymology 121: 210-228, (1986).
Tagliabue et al., "Selection of Monoclonal Antibodies Which Induce Internalization and Phosphorylation of $P185^{HER2}$ and Growth Inhibition of Cells With HER2/NEU Gene Amplification" International Journal of Cancer 47(6): 933-937, (Apr. 1, 1991).
Tokuda, et al., "In vitro and in vivo anti-tumor effects of a humanized monoclonal antibody against c-erb132 product", British journal of Cancer, 73, 1362-1365, (1996).
Verhoeyen et al., "Reshaping Human Antibodies: Grafting an Antilysozyme Activity" Science 239: 1534-1536, (1988).
Verma et al., "Efficacy and safety of three-weekly herceptin with paclitaxel in women with her2-positive metastatic breast cancer: preliminary results of a phase II trial" European Journal of Cancer (abstract only), 37:S146, (2001).
Vitetta and Uhr, "Monoclonal Antibodies as Agonists: An Expanded Role for Their Use in Cancer Therapy" Cancer Research 54(20): 5301-5309, (Oct. 15, 1994).
Vogel et al., "First-Line Herceptin Monotherapy in Metastatic Breast Cancer" Oncology 61(Suppl. 2): 37-42, (2001).
Washington et al., "A population pharmacokinetic (PK) model for trastuzumab (T) following weekly dosing" Clin Pharmacol Ther. (abstract only) 71:P12 (2002).
Watanabe et al., "Pharmacokinetically guided dose escalation study of anti-HER2 monoclonal antibody in patients with HER2/NEU-overexpressing metastatid:,breast cancer" Proceedings of the American Society of Clinical Oncology (Abstract 702 presented at the Annual ASCO meeting held May 15-18, 1998) 17:182a (1998).
Wolff et al., "Monoclonal antibody homodimers: enhanced antitumor activity in nude mice" Cancer Research 53(11): 2560-2565, (Jun. 1993).
Xu et al., "Antibody-Induced Growth Inhibition is Mediated Through Immunochemically and Functionally Distinct Epitopes on the Extracellular Domain of the c-erbB-2 (HER-2/neu) Gene Product p185", International Journal of Cancer 53(3): 401-408, (Feb. 1, 1993).
Yamamoto et al., "Similarity of protein encoded by the human c-erb-B-2 gene to epidermal growth factor receptor" (GenBank accession No. X03363), (Mar. 30, 1995).
Yamamoto et al., "Similarity of protein encoded by the human c-erb-B-2 gene to epidermal growth factor receptor" Nature 319: 230-234, (1986).
Zhang et al., "Shared antigenic epitopes and pathobiological functions of anti-p185ner$^2$fneu monoclonal antibodies" Experimental and Molecular Pathology 67: 15-25, (1999).
"ABPI Comendium of Data Sheets and Summaries of Product Characteristics 1999-2000" Datapharm Publications Limited, Aug. 1998, pp. iii, 255-256, 394, 1172-1173, 1296-1298.
"EMEA Public Statement on Trastuzumab (Herceptin)—New Pharmacokinetic Data", Jun. 2001, pp. 1-30.
"Letter of approval, label, and administrative document related to the geric compound (Taxotere) of docetaxel approved Jan. 6, 1998".
An, "Therapeutic Monoclonal Antibodies: From Bench to Clinic" Monoclonal Antibody Pharmacokinetics and Pharmodynamics, John Wiley and Sons Inc., publishers, 2009, 440-441.
Ardvanis, et. al. "Safety and Efficacy of Trastuzumab Every 3 Weeks Combined with Cytotoxic Chemotherapy in Patients with HER2-Positive Recurrent Breast Cancer: Filings from a Case Series" Onkologie 2005, pp. 558-564.
Berinstein, et. al. "Association of serum Rituximab (IDEC-C2B8) concentration and anti-tumor response in the treatment of recurrent low-grade or follicular non-Hodgkin's Lymphoma" Annals of Oncology, Kluwers Academic Publishers, publishers, vol. 9, 1998, pp. 995-1001.
Bruno, "Assessment of the Predictive Performance of a New Population Pharmacokinetic Model for Trastuzumab (Herceptin) and Simulation of Trastuzumab Steady-State Exposure During Long-Term Weekly Dosing" Abstracts of the Annual Meeting of the Population Approach Group in Europe, 2002, Abstract 310, p. 11.
Buzzoni, et. al. "Adjuvant Chemotherapy with Doxorubicin Plus Cyclophosphamide, Methotrexate, and Fluorouracil in the Treatment of Resectable Breast Cancer with More Than Three Positive Axillary Nodes" Journal of Clinical Oncology vol. 9, No. 12, Dec. 1991 pp. 2134-2140.
Clarke, et. al. "Clinical Pharmacokinetics of Docetaxel" Clin Pharmacokinet, Feb. 1999, pp. 99-114.
Cohen, "Declaration of Robert Lawrence Cohen, M.D." Jan. 2012.
Eniu, et. al. "Weekly Administration of Docetaxel and Paclitaxel in Metastatic or Advanced Breast Cancer" The Oncologist, 2005, pp. 665-685.
Fleming, et. al. "Phase I Trial of Recombinant Human Anti-HER2 Monoclonal Antibody (H) Plus with Low-Dose Interleukin-2 (IL-2) in Patients Solid Tumors" Proceedings of the American Society of Clinical Oncology (Abstract 710 presented at the Annual ASCO meeting held May 15-18, 1999), Perry and Anderson, eds., 1999, 18:184a.
Glennie, "Expert Report of Dr. Martin J. Glennie", Dec. 2011.
Glennie, "Second Expert Report of Dr. Martin J. Glennie", Jan. 2012.
Green, Clinical Pharmacology Review of Herceptin, Nov. 1998, 98/0369.
Herceptin Prescribing Information, Sep. 1998.
Information on Herceptin clinical testing NCCTG-983252 provided by the US National Cancer institute (NCI) clinical testing information database (PDQ®) http://web.archive.org/web/20110101000000*/ http://www.cancer.gov/clinicaltrials/search/view?cdrid=66689 &version=healthprofessional, Published Dec. 1998, Modified Jun. 2007, Downloaded Oct. 13, 2013.
Jones, et. al. "Optimizing Treatment of HER2-Positive Metastatic Breast Cancer" Seminars in Oncology, 2009, pp. 29-34.

(56) References Cited

OTHER PUBLICATIONS

Kaufmann, et. al. "The Developing Role of HER2 in Cancer Treatment" *HER-2 State-of-the-Art Conference* Nov. 21-23, 1999, pp. 10-35.
Leyland-Jones, et. al. "Pharmacokinetics, Safety, and Efficacy of Trastuzumab Administered Every Three Weeks in Combination with Paclitaxel" *Journal of Clinical Oncology* 2003, 21 (21), pp. 2965-3971.
McLaughlin, et. al. "Rituximab Chimeric Anti-CD20 Monoclonal Antibody Therapy for Relapsed Indolent Lymphoma: Half of Patients Respond to a Four-Dose Treatment Program" *Journal of Clinical Oncology*, 1998, vol. 16, No. 8 pp. 2825-2833.
Nisonoff et. al. "The Antibody Molecule" *Immunology: An International Series of Monographs and Treatises*, 1975, pp. 87, 98-99.
Pietras et. al. "Remission of Human Breast Cancer Xenografts on Therapy with Humanized Monoclonal Antibody to HER-2 Receptor and DNA-Reactive Drugs" *Oncogene*, 1998 vol. 17, pp. 2235-2249.
Ray-Coquard, et. al. "Vinorelbine and Cisplatin (CIVIC Regimen) for the Treatment of Metastatic Carcinoma after Failure of Antracycline-and/or Paclitaxel-Containing Regimens" *Cancer*, Jan. 1998, vol. 82 No. 1 pp. 134-140.
Rowland, et. al. "Clinical Pharmacokinetics: Concepts and Applications", Third Edition, M. Rowland and T. Tozer, eds., Lippincot Williams & Wilkins, publishers, 1995, pp. 2-5, 83-84, 87-88, 90, 93-94, 313-322, 347-357, 394-401, 418 and 491-492.
Schacter et. al. "Anticancer Drugs" *Handbook of Phase I/II Clinical Drug Trials*, J. O'Grady and P. Joubert, eds., CRC Press Inc., publishers, 1997, Ch. 38, pp. 523-534.
Shak, "Overview of the trastuzumab (Herceptin) anti-HER2 monoclonal antibody clinical program in HER2-overexpressing metastatic breast cancer." Herceptin Multinational Investigator Study Group. *Seminars in Oncology*, Aug. 1999, vol. 26, No. 4, Suppl 12, pp. 71-77.
Sparano "Taxanes for Breast Cancer: an Evidence-Based Review of Randomized Phase II and Phase III Trials" *Clinical Breast Cancer*, 2000, vol. 1, No. 1, pp. 36-40.
Van Poznak, et. al. "Critical Review of Current Treatment Strategies for Advanced Hormone Insensitive Breast Cancer" *Cancer Investigation*, 2002, vol. 20, Suppl. 2, pp. 1-14.
Vogel, et. al. "Efficacy and Safety of Herceptin" 1998, Dec. 12-15, Abstracts, p. 232, No. 23.
Waldmann, et. al. "Metabolism of Immunoglobulins" *Progr. Allergy*, 1969, vol. 13, pp. 19-31.
Washington, et. al. "A Population Pharmacokinetic (PK) Model for Trastuzumab (T) Following Weekly Dosing", *American Society for Clinical Pharmacology and Therapeutics*, Feb. 2002. MPI-30.
Wong "Trastuzumab: Anti-Her2 Antibody for Treatment of Metastatic Breast Cancer" *Cancer Practice*, 1999, vol. 7, No. 1, pp. 48-50.
Invalidation action filed by Celltrion against Korean Patent No. 1261749.
Invalidation action filed by Celltrion against Korean Patent No. 1261749 dated May 28, 2013 (English translation) (20 pages).
Genentech's response to invalidation action against Korean Patent No. 1261749 dated Oct. 10, 2013 (English translation) (22 pages).
Celltrion's rebuttal brief submitted in invalidation action against Korean Patent No. 1261749 dated Nov. 29, 2013 (English translation) (20 pages).
Genentech's response to Celltrion's rebuttal brief submitted in invalidation action against Korean Patent No. 1261749 dated Feb. 28, 2014 (English translation) (18 pages).
Celltrion's Brief submitted in invalidation action against Korean Patent No. 1261749 dated Mar. 26, 2014 (English translation) (13 pages).
Genentech's Supplemental Brief submitted in invalidation action against Korean Patent No. 1261749 dated May 9, 2014 (English translation) (4 pages).
Celltrion's Supplemental Reply Brief submitted in invalidation action against Korean Patent No. 1261749 dated May 9, 2014 (English translation) (12 pages).

Decision by the Intellectual Property Tribunal in invalidation action against Korean Patent No. 1261749 dated May 28, 2014 (in Korean with English translation) (35 pages).
Galluppi, et. al., "Integration of pharmacokinetic and pharmacodynamics studies in the discovery, development, and review of protein therapeutic agents: a conference report", Clin. Pharmacol. Ther., Jun. 2001, vol. 69, No. 6, pp. 387-399.
Groulx, Adrienne, "Introduction to Pharmacokinetics", ScianNews, 2006, vol. 9, No. 1, pp. 1-5.
Opposition Proceedings regarding European Patent No. 1 210 115.
Opposition by BioGeneriX AG (O1) to EP 1 210 115 dated May 5, 2010 (17 pages).
Opposition by Stada R&D GmbH (O2) to Ep 1 210 115 dated May 5, 2010 (29 pages).
Notice of Opposition by Teva Pharmaceutical Industries Ltd. (O3) to EP 1 210 115 dated May 6, 2010 (4 pages).
Facts and Arguments by Teva Pharmaceutical Industries Ltd (O3) in Opposition to EP 1 210 115 dated May 6, 2010 (10 pages).
Notice of Opposition by Celltrion, Inc. (O4) to EP 1 210 115 dated May 5, 2010 (5 pages).
Facts and Arguments by Celltrion, Inc. (O4) in Opposition to EP 1 210 115 dated May 5, 2010 (14 pages).
Opposition by Sandoz AG (O5) to EP 1 210 115 dated May 5, 2010 (27 pages).
Notice of Opposition by Synthon BV (O6) to EP 1 210 115 dated May 6, 2010 (5 pages).
Facts and Arguments by Synthon BV (O6) in Opposition to EP 1 210 115 dated May 6, 2010 (18 pages).
Proprietor's Response to Oppositions to EP 1 210 115 dated Dec. 24, 2010 (25 pages).
Summons to Attend Oral Hearings in Opposition to EP 1 210 115 dated Sep. 21, 2011 (16 pages).
Annex to Summons to Attend Oral Hearings, Nonbinding, Preliminary Opinion of the Opposition Division in Opposition to EP 1 210 115 dated Sep. 21, 2011 (16 pages).
Response to the Preliminary Opinion of the Opposition Division filed by BioGeneriX AG and Teva Pharmaceutical Industries Ltd. (O1 and O3), in Opposition to EP 1 210 115, dated Dec. 9, 2011 (3 pages).
Response to the Preliminary Opinion of the Opposition Division filed by STADA R&D GmbH (O2), in Opposition to EP 1 210 115 dated Dec. 9, 2011 (27 pages).
Response to the Preliminary Opinion of the Opposition Division filed by Celltrion, Inc. (O4), in Opposition to EP 1 210 115, dated Dec. 9, 2011 (3 pages).
Response to the Preliminary Opinion of the Opposition Division filed by Sandoz AG (O5), in Opposition to EP 1 210 115, dated Dec. 9, 2011 (27 pages).
Response to the Preliminary Opinion of the Opposition Division filed by Synthon BV (O6) in Opposition to EP 1 210 115, dated Dec. 9, 2011 (1 page).
Response to the Preliminary Opinion of the Opposition Division filed by Genentech, Inc., in Opposition to EP 1 210 115, dated Dec. 9, 2011 (10 pages).
Further submission by Celltrion, Inc. (O4) in Opposition to EP 1 210 115, dated Jan. 24, 2012 (4 pages).
Further submission by Sandoz AG (O5), Opposition to EP 1 210 115, dated Jan. 17, 2012 (16 pages).
Further submission by Genentech, Inc. in Opposition to EP 1 210 115, dated Jan. 27, 2012 (2 pages).
Further submission by Genentech, Inc. in response to evidence filed by Celltrion, Inc. (O4) dated Feb. 3, 2012 (2 pages).
Minutes of the Oral Proceedings in Opposition to EP 1 210 115 dated Feb. 9, 2012 (3 pages).
Decision of Opposition Division in Opposition to EP 1 210 115, dated May 4, 2012 (22 pages).
Leyland-Jones, et. al., "Pharmacologic insights into the future of trastuzumab", Annals of Oncology, 2001, vol. 12, Suppl. 1, pp. S43-S47.
Leyland-Jones, Brian, "Dose Scheduling—Herceptin", Oncology, 2001, vol. 81, Suppl. 2, pp. 31-36.

(56) References Cited

OTHER PUBLICATIONS

Cobleigh, et. al., "Efficacy and Safety of Herceptin™ (Humanized Anti-HER2 Antibody) as a Single Agent in 222 Women with HER2 Overexpression Who Relapsed Following Chemotherapy for Metastatic Breast Cancer", Proc. Am Soc. Clin. Oncol., 1998, vol. 17, Abstract #376, p. 97a.
Tokuda, et. al., "Dose escalation and pharmacokinetic study of a humanized anti-HER2 monoclonal antibody in patients with HER2/neu-overexpressing metastatic breast cancer", British Journal of Cancer, 1999, vol. 81, No. 8, pp. 1419-1425.
Expert Report of Dr. Martin J. Glennie in Opposition to European Patent No. EP 1 210 115 dated Sep. 12, 2011 (8 pages).
Annex of Expert Report of Dr. Martin J. Glennie, Curriculum Vitae of Professor Martin Glennie, in Opposition to European Patent No. EP 1 210 115 dated Sep. 12, 2011 (7 pages).
Declaration of Jerome A. Moore in Opposition to European Patent No. EP 1 210 115 dated Dec. 8, 2011 (11 pages).
Declaration of N. "Shasha" Jumbe, PhD in Opposition to European Patent No. EP 1 210 115 dated Dec. 8, 2011 (9 pages).
Pharsight, "WinNolin®—Industry-Standard PK/PD Modeling and Analysis", 2011, retrieved from http://www.pharsight.com/products/prod_winnolin_home.php on Sep. 12, 2011 (3 pages).
Lu, et. al., "Assessment of the Predictive Performance of a New Population Pharmacokinetic Model for Trastuzumab (Herceptin) and Simulation of Trastuzumab Steady-State Exposure During Long-Term Weekly Dosing", Abstracts of the Annual Meeting of the population Approach Group in Europe, 2002, Abstract #310, p. 11.
Declaration of Robert Lawrence Cohen, M.D. in Opposition to European Patent No. EP 1 210 115 dated Jan. 26, 2012 (4 pages).
Exhibit A to Declaration of Robert Lawrence Cohen, M.D., Curriculum Vitae of Robert Lawrence Cohen in Opposition to European Patent No. EP 1 210 115 dated Jan. 26, 2012 (8 pages).
Exhibit B to Declaration of Robert Lawrence Cohen M.D., Maloney, et. al., "Phase I Clinical Trial Using Escalating Single-Dose Infusion of Chimeric Anti-CD20 Monoclonal Antibody (IDEC-C2B8) in Patients with Recurrent B-Cell Lymphoma", Blood, Oct. 1994, vol. 84, No. 8, pp. 2457-2466 in Opposition to European Patent No. EP 1 210 115 submitted on Jan. 26, 2012.
Exhibit C to Declaration of Robert Lawrence Cohen M.D., McLaughlin, et. al., "Rituximab Chimeric Anti-CD20 Antibody Therapy for Relapsed Indolent Lymphoma: Half of Patients Respond to a Four-Dose Treatment Program", J. Clin. Oncol., Aug. 1998, vol. 16, No. 8, pp. 2825-2833, in Opposition to European Patent No. EP 1 210 115 submitted on Jan. 26, 2012.
Exhibit D to Declaration of Robert Lawrence Cohen M.D., Prescribing Information of Rituxan (Rituximab), Initial US approval: 1997, in Opposition to European Patent No. EP 1 210 115 submitted on Jan. 26, 2012 (38 pages).
Exhibit E to Declaration of Robert Lawrence Cohen M.D., Final Labeling Text for Herceptin (trastuzumab), Initial US Approval: 1998, in Opposition to European Patent No. EP 1 210 115 submitted on Jan. 26, 2012 (32 pages).
Exhibit F to Declaration of Robert Lawrence Cohen M.D., Berinstein, et. al., "Association of serum Rituximab (IDEC-C2B8) concentration and anti-tumor response in the treatment of recurrent low-grade or follicular non-Hodgkin's lymphoma", Annals of Oncology, 1998, vol. 9, pp. 995-1001, in Opposition to European Patent No. EP 1 210 115 submitted on Jan. 26, 2012.
Second Declaration of Robert Lawrence Cohen, M.D. In Opposition to European Patent No. EP 1 210 115 dated Feb. 2, 2012 (2 pages).
Notice of Appeal filed by Genentech, Inc. in Opposition to European Patent No. EP 1 210 115 dated Jul. 6, 2012 (1 page).
Proprietor's Grounds of Appeal filed in Opposition to European Patent No. EP 1 210 115 dated Sep. 13, 2012 (40 pages).
Further Proprietor's Statement regarding Grounds of Appeal filed in Opposition to European Patent No. EP 1 210 115 dated Sep. 14, 2012 (1 page).
Declaration of George Grass, Pharm.D, Ph.D. in Opposition to European Patent No. EP 1 210 115 dated Sep. 11, 2012 (17 pages).
Bruno, et. al., "Population pharmacokinetics of trastuzumab in patients with HER2+ metastatic breast cancer", Cancer Chemother Pharmacol, 2005, vol. 56, pp. 361-369.
Ette, Ene I., "Stability and Performance of a Population Pharmacokinetic Model", J Clin Pharmacol, 1997, vol. 37, pp. 486-495.
Sheiner, et. al., "Estimation of Population Characteristics of Pharmacokinetic Parameters from Routine Clinical Data", Journal of Pharmacokinetics and Biopharmaceutics, 1977, vol. 5, No. 5, pp. 445-479.
US Department of Health and Human Services, "Guidance for Industry: Population Pharmacokinetics", Feb. 1999 (35 pages).
Morell, et. al., "Metabolic Properties of IgG Subclasses in Man", Journal of Clinical Investigation, 1970, col. 49, pp. 673-680.
Opponents' Response to Proprietor's Notice of Appeal by BioGeneriX AG and Teva Pharmaceutical Industries Ltd filed in Opposition to European Patent No. EP 1 210 115 dated Jan. 17, 2013 (12 pages).
Opponent's Response to Proprietor's Notice of Appeal by STADA R&D GmbH filed in Opposition to European Patent No. EP 1 210 115 dated Jan. 24, 2013 (15 pages).
Opponent's Response to Proprietor's Notice of Appeal by Celltrion, Inc. filed in Opposition to European Patent No. EP 1 210 115 dated Jan. 25, 2013 (19 pages).
Declaration of Megan A. Gibbs, Ph.D. in Opposition to European Patent No. EP 1 210 115 dated Jan. 18, 2013 (4 pages).
Exhibit A in Declaration of Megan A. Gibbs, Ph.D., Curriculum Vitae of Megan A. Gibbs, Ph.D., in Opposition to European Patent No. EP 1 210 115 dated Jan. 18, 2013 (10 pages).
Exhibit S3 in Declaration of Megan A. Gibbs, Ph.D., Morell, et. al., "Metabolic Properties of IgG Subclasses in Men", Journal of Clinical Investigation, 1970, vol. 49, pp. 673-680 in Notice of Opposition of European Patent No. EP 1 210 115 submitted on Jan. 18, 2013.
Exhibit S2 in Declaration of Megan A. Gibbs, Ph.D., Final Labeling Text for Herceptin (trastuzumab), Initial US Approval: 1998, in Opposition to European Patent No. EP 1 210 115 submitted on Jan. 26, 2012 (32 pages).
Opponent's Response to Proprietor's Notice of Appeal by Sandoz AG filed in Opposition to European Patent No. EP 1 210 115 dated Jan. 28, 2013 (19 pages).
Opponent's Response to Proprietor's Notice of Appeal by Synthon BV filed in Opposition to European Patent No. EP 1 210 115 dated Jan. 28, 2013 (21 pages).
Cancellation Action filed by Celltrion against Mexican Patent No. 259512.
Cancellation Action filed by Celltrion against Mexican Patent No. 259512 dated Jan. 6, 2012 (in Spanish with English translation) (136 pages).
Genentech's Response to Cancellation Action filed by Celltrion against Mexican Patent No. 259512 dated Apr. 16, 2012 (in Spanish with English translation) (134 pages).
Manifestations Against the Response Brief regarding Cancellation Action filed by Celltrion against Mexican Patent No. 259512 dated Aug. 28, 2012 (31 pages).
Technical Report Issued by Mexican Patent Office regarding Cancellation Action filed by Celltrion against Mexican Patent No. 259512 dated Mar. 21, 2014 (in Spanish with English translation) (196 pages).
Genentech's Allegations Brief filed in response to Technical Opinion Issued by Mexican Patent Office regarding Cancellation Action filed by Celltrion against Mexican Patent No. 259512 dated May 16, 2014 (in Spanish with English translation) (35 pages).
Dismissal of Cancellation Action filed by Celltrion against Mexican Patent No. 259512 dated May 30, 2014 (in Spanish with English translation) (56 pages).
Ex officio Cancellation Action initiated by Mexican Patent Office (IMPI) against Mexican Patent No. 259512 dated Oct. 22, 2014 (in Spanish with English translation) (22 pages).
Genentech's Answer to ex officio Cancellation Action initiated by Mexican Patent Office (IMPI) against Mexican Patent No. 259512 dated Dec. 5, 2014 (77 pages).

(56) References Cited

OTHER PUBLICATIONS

Genentech's Brief of Final Allegations filed with Federal Court of Fiscal and Administrative Justice regarding Mexican Patent No. 259512 dated Jun. 24, 2015 (in Spanish with English translation) (28 pages).
Invalidation Action filed by Celltrion against Polish Patent No. 202369.
Invalidation Action filed by Celltrion against Polish Patent No. 202369 dated Aug. 23, 2011 (21 pages).
Genentech's Motion for Suspension of Invalidation Action filed by Celltrion against Polish Patent No. 202369 dated Jan. 20, 2012 (3 pages).
Celltrion's Reply to Genentech's Motion for Suspension of Invalidation Action filed by Celltrion against Polish Patent No. 202369 dated May 11, 2012 (in Polish with English translation) (7 pages).
Genentech's Supplemental Reply regarding invalidation against Polish Patent No. 202369 dated Oct. 2, 2012 (21 pages).
Celltrion's Submission regarding invalidation against Polish Patent No. 202369 dated Oct. 12, 2012 (18 pages).
Documents submitted by Celltrion in invalidation action against Polish Patent No. 202369 dated May 21, 2013 (13 pages).
Genentech's Pleading submitted in invalidation against Polish Patent No. 202369 dated Jul. 24, 2013 (in Polish with English translation) (35 pages).
Celltrion's Pleading submitted in invalidation against Polish Patent No. 202369 dated Jul. 24, 2013 (11 pages).
Attachment to Celltrion's pleading, 2$^{nd}$ Expert Report of Dr. Martin J. Glennie dated Jan. 23, 2012 in invalidation against Polish Patent No. 202369 (12 pages).
Decision of Polish Patent Office in invalidation against Polish Patent No. 202369 dated Oct. 23, 2013 (26 pages).
Documents Submitted by Celltrion to EMEA, Submitted as evidence in invalidation against Polish Patent No. 202369, Date: May 24, 2013 (13 pages).
EMEA Scientific Advice for Trastuzumab, Submitted as evidence in invalidation against Polish Patent No. 202369, Date: Dec. 18, 2008 (29 pages).
1$^{st}$ Central-Eastern European Congress on Biosimilars, "Biosimilar, a New Treatment Option for Breast Cancer", Submitted as evidence in invalidation against Polish Patent No. 202369, Date: Oct. 13, 2011 (29 pages).
Celltrion's motion for invalidation of the Decision of Patent Office for changing the patent in invalidation against Polish Patent No. 202369 dated Nov. 3, 2013 (29 pages).
Celltrion's Motion to Suspend Court Proceedings in invalidation against Polish Patent No. 202369 dated Nov. 3, 2013 (in Polish) (15 pages).
Celltrion's Further Pleading submitted in invalidation against Polish Patent No. 202369 dated Nov. 3, 2013 (in Polish with English translation) (25 pages).
Genentech's Answer to the Application submitted in invalidation against Polish Patent No. 202369 dated Apr. 8, 2015 (10 pages).
Judgement by the Provincial Administrative Court of Warsaw in invalidation against Polish Patent No. 202369 dated Apr. 22, 2015 (in Polish with English translation) (78 pages).
Genentech's Cassation Appeal submitted in invalidation against Polish Patent No. 202369 dated Aug. 3, 2015 (in Polish with English translation) (12 pages).
*Celltrion* v. *Genentech* trial in the High Court of the Kong Special Administrative Region, Court of First Instance, Case No. 1873 regarding HK Patent No. 1048260.
*Celltrion* v. *Genentech* trial in the High Court of the Kong Special Administrative Region, Court of First Instance, Case No. 1873 regarding HK Patent No. 1048260, Order regarding Filing Defence, Date: Feb. 18, 2013 (1 page).
*Celltrion* v. *Genentech* trial in the High Court of the Kong Special Administrative Region, Court of First Instance, Case No. 1873 regarding HK Patent No. 1048260, Sealed Order for Directions, Date: Jul. 14, 2013 (6 pages).
*Celltrion* v. *Genentech* trial in the High Court of the Kong Special Administrative Region, Court of First Instance, Case No. 1873 regarding HK Patent No. 1048260, Summons, Date: Aug. 29, 2013.
*Celltrion* v. *Genentech* trial in the High Court of the Kong Special Administrative Region, Court of First Instance, Case No. 1873 regarding HK Patent No. 1048260, Order for Advertisement, Date: Sep. 17, 2014 (3 pages).
*Celltrion* v. *Genentech* trial in the High Court of the Kong Special Administrative Region, Court of First Instance, Case No. 1873 regarding HK Patent No. 1048260, Sealed Order for Adjournment, Date: Sep. 17, 2014 (3 pages).
*Celltrion* v. *Genentech* trial in the High Court of the Kong Special Administrative Region, Court of First Instance, Case No. 1873 regarding HK Patent No. 1048260, Sealed Order regarding Claim Amendment, Date: Sep. 17, 2014 (3 pages).
*Celltrion* v. *Genentech* trial in the High Court of the Kong Special Administrative Region, Court of First Instance, Case No. 1873 regarding HK Patent No. 1048260, Note from Master Ho regarding Expert Directions, Date: Oct. 7, 2014 (1 page).
*Celltrion* v. *Genentech* trial in the High Court of the Kong Special Administrative Region, Court of First Instance, Case No. 1873 regarding HK Patent No. 1048260, Sealed Order regarding Expert Directions, Date: Nov. 14, 2014 (5 pages).
*Celltrion* v. *Genentech* trial in the High Court of the Kong Special Administrative Region, Court of First Instance, Case No. 1873 regarding HK Patent No. 1048260, Consent Summons, Section 102 and Fact Evidence, Date: Dec. 10, 2014 (4 pages).
*Celltrion* v. *Genentech* trial in the High Court of the Kong Special Administrative Region, Court of First Instance, Case No. 1873 regarding HK Patent No. 1048260, Order for Cost Summary Assessment, Date: Jan. 23, 2015 (1 page).
*Celltrion* v. *Genentech* trial in the High Court of the Kong Special Administrative Region, Court of First Instance, Case No. 1873 regarding HK Patent No. 1048260, Sealed Order for Claim Amendment, Date: Jan. 26, 2015 (3 pages).
*Celltrion* v. *Genentech* trial in the High Court of the Kong Special Administrative Region, Court of First Instance, Case No. 1873 regarding HK Patent No. 1048260, Consent Summons for Extension of Time to File List of Documents, Date: Feb. 12, 2015 (3 pages).
*Celltrion* v. *Genentech* trial in the High Court of the Kong Special Administrative Region, Court of First Instance, Case No. 1873 regarding HK Patent No. 1048260, Consent Summons for Section 102 Timings for Fact Evidence, Date: Mar. 9, 2015 (3 pages).
*Celltrion* v. *Genentech* trial in the High Court of the Kong Special Administrative Region, Court of First Instance, Case No. 1873 regarding HK Patent No. 1048260, Consent Summons for Discovery, Date: Mar. 13, 2015 (2 pages).
*Celltrion* v. *Genentech* trial in the High Court of the Kong Special Administrative Region, Court of First Instance, Case No. 1873 regarding HK Patent No. 1048260, Letter from the Court with Queries Regarding Consent Summons, Date: Mar. 27, 2015 (1 page).
*Celltrion* v. *Genentech* trial in the High Court of the Kong Special Administrative Region, Court of First Instance, Case No. 1873 regarding HK Patent No. 1048260, Order of Master Ho regarding Case Management Conference, Date: Jul. 23, 2015 (3 pages).
*Celltrion* v. *Genentech* trial in the High Court of the Kong Special Administrative Region, Court of First Instance, Case No. 1873 regarding HK Patent No. 1048260, Particulars of Objections, Date: Oct. 2, 2013 (7 pages).
*Celltrion* v. *Genentech* trial in the High Court of the Kong Special Administrative Region, Court of First Instance, Case No. 1873 regarding HK Patent No. 1048260, Writ of Summons, Date: Oct. 2, 2013 (5 pages).
*Celltrion* v. *Genentech* trial in the High Court of the Kong Special Administrative Region, Court of First Instance, Case No. 1873 regarding HK Patent No. 1048260, Acknowledgement of Service of Writ of Summons, Date: Oct. 16, 2013 (1 page).
*Celltrion* v. *Genentech* trial in the High Court of the Kong Special Administrative Region, Court of First Instance, Case No. 1873 regarding HK Patent No. 1048260, Defence, Date: Jan. 22, 2014 (2 pages).

(56) References Cited

OTHER PUBLICATIONS

*Celltrion* v. *Genentech* trial in the High Court of the Kong Special Administrative Region, Court of First Instance, Case No. 1873 regarding HK Patent No. 1048260, Timetabling Questionnaire of the Plaintiff, Date; Mar. 28, 2014 (9 pages).
*Celltrion* v. *Genentech* trial in the High Court of the Kong Special Administrative Region, Court of First Instance, Case No. 1873 regarding HK Patent No. 1048260, Further and Better Particulars of Objections, Date: Jul. 4, 2014 (11 pages).
*Celltrion* v. *Genentech* trial in the High Court of the Kong Special Administrative Region, Court of First Instance, Case No. 1873 regarding HK Patent No. 1048260, Summons for Further and Better Particulars of Objections, Date: Jul. 23, 2014 (5 pages).
*Celltrion* v. *Genentech* trial in the High Court of the Kong Special Administrative Region, Court of First Instance, Case No. 1873 regarding HK Patent No. 1048260, Mediation Certificate of the Defendant, Date: Jul. 28, 2014 (4 pages).
*Celltrion* v. *Genentech* trial in the High Court of the Kong Special Administrative Region, Court of First Instance, Case No. 1873 regarding HK Patent No. 1048260, Timetabling Questionnaire of the Defendant, Date; Jul. 28, 2014 (9 pages).
*Celltrion* v. *Genentech* trial in the High Court of the Kong Special Administrative Region, Court of First Instance, Case No. 1873 regarding HK Patent No. 1048260, Agreed English Translation of Hong Kong Standard Patent No. 1048260, Date: Aug. 15, 2014 (67 pages).
*Celltrion* v. *Genentech* trial in the High Court of the Kong Special Administrative Region, Court of First Instance, Case No. 1873 regarding HK Patent No. 1048260, Plaintiff's Notice to Admit, Date: Sep. 26, 2014 (7 pages).
*Celltrion* v. *Genentech* trial in the High Court of the Kong Special Administrative Region, Court of First Instance, Case No. 1873 regarding HK Patent No. 1048260, Defendant's Admissions to Facts, Date: Oct. 23, 2014 (7 pages).
*Celltrion* v. *Genentech* trial in the High Court of the Kong Special Administrative Region, Court of First Instance, Case No. 1873 regarding HK Patent No. 1048260, Listing Documents of the Plaintiff, Date: Nov. 14, 2014 (9 pages).
*Celltrion* v. *Genentech* trial in the High Court of the Kong Special Administrative Region, Court of First Instance, Case No. 1873 regarding HK Patent No. 1048260, Listing Documents of the Defendant, Date: Feb. 16, 2015 (10 pages).
*Celltrion* v. *Genentech* trial in the High Court of the Kong Special Administrative Region, Court of First Instance, Case No. 1873 regarding HK Patent No. 1048260, Plaintiff's Listing Questionnaire, Date: Jul. 20, 2015 (7 pages).
*Celltrion* v. *Genentech* trial in the High Court of the Kong Special Administrative Region, Court of First Instance, Case No. 1873 regarding HK Patent No. 1048260, Defendant's Listing Questionnaire, Date: Jul. 21, 2015 (7 pages).
*Celltrion* v. *Genentech* trial in the High Court of the Kong Special Administrative Region, Court of First Instance, Case No. 1873 regarding HK Patent No. 1048260, Affidavit of Anthony Clinton Dudley Evans, Date: Jul. 24, 2014 (7 pages).
*Celltrion* v. *Genentech* trial in the High Court of the Kong Special Administrative Region, Court of First Instance, Case No. 1873 regarding HK Patent No. 1048260, Second Affidavit of Anthony Clinton Dudley Evans, Date: Aug. 29, 2014 (6 pages).
*Celltrion* v. *Genentech* trial in the High Court of the Kong Special Administrative Region, Court of First Instance, Case No. 1873 regarding HK Patent No. 1048260, Affidavit of Wong Tak Kay Alison, Date: Sep. 17, 2014 (7 pages).
*Celltrion* v. *Genentech* trial in the High Court of the Kong Special Administrative Region, Court of First Instance, Case No. 1873 regarding HK Patent No. 1048260, Exhibit WTKA-5, Proposed Claim Amendments to Claims of Hong Kong Standard Patent No. HK 1048260, in Affidavit of Wong Tak Kay Alison, Date: Sep. 17, 2014 (5 pages).

*Celltrion* v. *Genentech* trial in the High Court of the Kong Special Administrative Region, Court of First Instance, Case No. 1873 regarding HK Patent No. 1048260, Third Affidavit of Anthony Clinton Dudley Evans, Date: Oct. 3, 2014 (11 pages).
*Celltrion* v. *Genentech* trial in the High Court of the Kong Special Administrative Region, Court of First Instance, Case No. 1873 regarding HK Patent No. 1048260, Witness Statement and Affirmation of David Kim, Date: Mar. 20, 2015 (32 pages).
Invalidation Action by Celltrion against South African Patent No. 2002/1229.
Invalidation Action filed by Celltrion against South African Patent No. 2002/1229 dated Oct. 28, 2011 (9 pages).
Genentech's Request for Extension of Time in Invalidation Action against South African Patent No. 2002/1229 dated Jan. 3, 2012 (2 pages).
Grounds for Genentech's Request for Extension of Time—Founding affidavit and motion to amend in Invalidation Action against South African Patent No. 2002/1229 dated Jan. 3, 2012 (2 pages).
Notice of Intention to Amend in Terms of Rule 28 in Invalidation Action Against South African Patent No. 2002/1229 dated Jun. 11, 2012 (9 pages).
Founding Affidavit of Diane Marschang in Invalidation Action Against South African Patent No. 2002/1229 dated Oct. 4, 2012 (23 pages).
Order to Amend Patent in Invalidation Action Against South African Patent No. 2002/1229 dated Mar. 12, 2013 (2 pages).
Celltrion's Amended Motion for Revocation in Invalidation Actin Against South African Patent No. 2002/1229 dated Jul. 6, 2012 (18 pages).
Kostowski, W., Excerpt from "Pharmacology, Basics of Pharmacology, Coursebook for Students of Medicine and Physicians", Warsaw, First Edition, 1998, pp. 89-91.
Founding Affidavit of Martin John Glennie in Invalidation Action Against South African Patent No. 2002/1229 dated Aug. 23, 2013 (82 pages).
Supporting Affidavit of Kyungha Shin in Invalidation Action Against South African Patent No. 2002/1229 dated Aug. 20, 2013 (2 pages).
Founding Affidavit of George M. Grass in Invalidation Action Against South African Patent No. 2002/1229 dated Feb. 27, 2014 (125 pages).
Affidavit of Peter Jeffery Barrett-Lee in Invalidation Action Against South African Patent No. 2002/1229 dated Feb. 28, 2014 (40 pages).
Replying Affidavit of Martin John Glennie in Invalidation Action Against South African Patent No. 2002/1229 dated Oct. 3, 2014 (135 pages).
Replying Affidavit of Robert Howard Earhart in Invalidation Action Against South African Patent No. 2002/1229 dated Sep. 30, 2014 (129 pages).
Replying Affidavit of Robert Charles Frederick Leonard in Invalidation Action Against South African Patent No. 2002/1229 dated Sep. 30, 2014 (59 pages).
Invalidation Action Against Chinese Patent No. CN 00814890.3.
Koizumi, et. al., "Multicompartmental Analysis of the Kinetics of Radioiodinated Monoclonal Antibody in Patients with Cancer", J. Nucl. Med., 1986, vol. 27, pp. 1243-1254.
Eger, et. al., "Kinetic Model for the Biodistribution of an $^{111}$In-labeled Monoclonal Antibody in Humans", Cancer Res., 1987, vol. 47, pp. 3328-3336.
Genentech's Appeal Brief submitted in Invalidation of Chinese Decision No. 19128 dated Nov. 16, 2012 (Chinese with English translation (16 pages).
Administrative Judgement in Request for invalidation of Chinese Patent No. CN 00814890.3 dated Aug. 23, 2010 (English translation) (12 pages).
Request for Invalidation filed against Chinese Patent No. ZL00814590.3 dated Dec. 30, 2011 (11 pages).
Genentech's Response to Request for invalidation of Chinese Patent No. CN 00814890.3 dated Feb. 26, 2012 (9 pages).
Genentech's Supplemental Response to Request for invalidation of Chinese Patent No. CN 00814890.3 dated May 31, 2012 (11 pages).

(56) References Cited

OTHER PUBLICATIONS

Decision of Examination of the Request for Invalidation No. 19128 relating to Chinese Patent No. 00814590.3, Date: Aug. 8, 2012 (English translation) (20 pages).
Administrative Judgement by Beijing First Intermediate People's Court of the PRC in Request for invalidation of Chinese Patent No. CN 000814890.3, Date: Dec. 19, 2013 (English translation) (20 pages).
Administrative Judgement by Beijing High Court of the PRC in Request for invalidation of Chinese Patent No. CN 000814890.3, Date: Dec. 19, 2013 (English translation) (21 pages).
Petition to Supreme People's Court for Retrial in Request for invalidation of Chinese Patent No. CN 000814890.3, Date: Oct. 30, 2015 (Chinese with English translation) (16 pages).
*Hospira* v. *Genentech* trial in the High Court of Justice Chancery Division 2 Patents Court, Case No. HC12C03487 regarding EP (UK) 1 210 115. Grounds of Invalidity dated Sep. 13, 2012 (7 pages).
*Hospira* v. *Genentech* trial in the High Court of Justice Chancery Division 2 Patents Court, Case No. HC12C03487 regarding EP (UK) 1 210 115. Amended Particulars of Claim, Date: Sep. 13, 2012 (3 pages).
*Hospira* v. *Genentech* trial in the High Court of Justice Chancery Division 2 Patents Court, Case No. HC12C03487 regarding EP (UK) 1 210 115. Re-amended Grounds of Invalidity, Date: Sep. 13, 2012 (8 pages).
*Hospira* v. *Genentech* trial in the High Court of Justice Chancery Division 2 Patents Court, Case No. HC12C03487 regarding EP (UK) 1 210 115. Re-Amended Defence, Date: Oct. 29, 2012 (3 pages).
*Hospira* v. *Genentech* trial in the High Court of Justice Chancery Division 2 Patents Court, Case No. HC12C03487 regarding EP (UK) 1 210 115. Confidential Witness Statement of Michael John Gilbert, Date: Nov. 21, 2012 (7 pages).
*Hospira* v. *Genentech* trial in the High Court of Justice Chancery Division 2 Patents Court, Case No. HC12C03487 regarding EP (UK) 1 210 115. Exhibit MJG-1, correspondence between Taylor Wessing and Mewburn Ellis in Confidential Witness Statement of Michael John Gilbert, Date: Nov. 21, 2012 (7 pages).
*Hospira* v. *Genentech* trial in the High Court of Justice Chancery Division 2 Patents Court, Case No. HC12C03487 regarding EP (UK) 1 210 115. Exhibit MJG-2, Hospira Press Release, "Hospira, Celltrion, Enter Business Cooperation Agreement to Develop and Market Biogeneric Drugs", 2009, in Confidential Witness Statement of Michael John Gilbert, Date: Nov. 21, 2012 (2 pages).
*Hospira* v. *Genentech* trial in the High Court of Justice Chancery Division 2 Patents Court, Case No. HC12C03487 regarding EP (UK) 1 210 115. Exhibit MJG-3, Hospira website, "About Hospira", in Confidential Witness Statement of Michael John Gilbert, Date: Nov. 21, 2012 (2 pages).
*Hospira* v. *Genentech* trial in the High Court of Justice Chancery Division 2 Patents Court, Case No. HC12C03487 regarding EP (UK) 1 210 115. Exhibit MJG-4, United States Securities and Exchange Commission, Form 10-Q Quarterly report for Hospira, Inc., dated Aug. 1, 2012 in Confidential Witness Statement of Michael John Gilbert, Date: Nov. 21, 2012 (69 pages).
*Hospira* v. *Genentech* trial in the High Court of Justice Chancery Division 2 Patents Court, Case No. HC12C03487 regarding EP (UK) 1 210 115. Exhibit MJG-5, Celltrion Outlook Presentation, 2nd Quarter 2012, in Confidential Witness Statement of Michael John Gilbert, Date: Nov. 21, 2012 (15 pages).
*Hospira* v. *Genentech* trial in the High Court of Justice Chancery Division 2 Patents Court, Case No. HC12C03487 regarding EP (UK) 1 210 115. Exhibit MJG-6, Celltrion Outlook Presentation, 3rd Quarter 2012, in Confidential Witness Statement of Michael John Gilbert, Date: Nov. 21, 2012 (16 pages).
*Hospira* v. *Genentech* trial in the High Court of Justice Chancery Division 2 Patents Court, Case No. HC12C03487 regarding EP (UK) 1 210 115. Skeleton Argument of the Defendant for Case Management Conference, Date: Nov. 22, 2012 (4 pages).
*Hospira* v. *Genentech* trial in the High Court of Justice Chancery Division 2 Patents Court, Case No. HC12C03487 regarding EP (UK) 1 210 115. Skeleton Argument of the Claimant for Case Management Conference, Date: Nov. 22, 2012 (5 pages).
*Hospira* v. *Genentech* trial in the High Court of Justice Chancery Division 2 Patents Court, Case No. HC12C03487 regarding EP (UK) 1 210 115. Supplementary Skeleton Argument of the Claimant, Date: Nov. 22, 2012 (1 page).
*Hospira* v. *Genentech* trial in the High Court of Justice Chancery Division 2 Patents Court, Case No. HC12C03487 regarding EP (UK) 1 210 115. Transcript of the Case Management Conference, Date: Nov. 22, 2012 (21 pages).
*Hospira* v. *Genentech* trial in the High Court of Justice Chancery Division 2 Patents Court, Case No. HC12C03487 regarding EP (UK) 1 210 115. First Witness Statement of Nigel Martin Stoate, Date: Dec. 3, 2012 (4 pages).
*Hospira* v. *Genentech* trial in the High Court of Justice Chancery Division 2 Patents Court, Case No. HC12C03487 regarding EP (UK) 1 210 115. Order for Directions following Case Management Conference, Date: Nov. 22, 2012 (5 pages).
*Hospira* v. *Genentech* trial in the High Court of Justice Chancery Division 2 Patents Court, Case No. HC12C03487 regarding EP (UK) 1 210 115. Consent Order demanding further information, Date: Dec. 12, 2012 (3 pages).
*Hospira* v. *Genentech* trial in the High Court of Justice Chancery Division 2 Patents Court, Case No. HC12C03487 regarding EP (UK) 1 210 115. Notice to Admit Facts and Request for Further Information from the Defendant, Date: Feb. 15, 2013 (7 pages).
*Hospira* v. *Genentech* trial in the High Court of Justice Chancery Division 2 Patents Court, Case No. HC12C03487 regarding EP (UK) 1 210 115. Defendant's Response to the Claimant's Notice to Admit Facts and Part 18 Request for Further Information, Date: Mar. 1, 2013 (3 pages).
*Hospira* v. *Genentech* trial in the High Court of Justice Chancery Division 2 Patents Court, Case No. HC12C03487 regarding EP (UK) 1 210 115. Supplemental Claimant's Notice to Admit Facts and Part 18 Request for Further Information from the Defendant, Date: Jul. 4, 2013 (3 pages).
*Hospira* v. *Genentech* trial in the High Court of Justice Chancery Division 2 Patents Court, Case No. HC12C03487 regarding EP (UK) 1 210 115. Defendant's Response to the Claimant's Supplemental Notice to Admit Facts and Part 18 Request for Further Information, Date: Jul. 15, 2013 (3 pages).
*Hospira* v. *Genentech* trial in the High Court of Justice Chancery Division 2 Patents Court, Case No. HC12C03487 regarding EP (UK) 1 210 115. Witness Statement of Charles Anthony Nettleton Balme, Date: Jul. 18, 2013 (7 pages).
*Hospira* v. *Genentech* trial in the High Court of Justice Chancery Division 2 Patents Court, Case No. HC12C03487 regarding EP (UK) 1 210 115. Exhibit CAB-1, inter partes correspondence regarding confidentiality of material, in Witness Statement of Charles Anthony Nettleton Balme, Date: Jul. 18, 2013 (9 pages).
*Hospira* v. *Genentech* trial in the High Court of Justice Chancery Division 2 Patents Court, Case No. HC12C03487 regarding EP (UK) 1 210 115. Exhibit CAB-2, Affidavit by HyukJae Lee dated Dec. 5, 2012, in Witness Statement of Charles Anthony Nettleton Balme, Date: Jul. 18, 2013 (6 pages).
*Hospira* v. *Genentech* trial in the High Court of Justice Chancery Division 2 Patents Court, Case No. HC12C03487 regarding EP (UK) 1 210 115. Claimant's Pleading of Matters Falling within the Common General Knowledge, Date: Sep. 27, 2013 (7 pages).
*Hospira* v. *Genentech* trial in the High Court of Justice Chancery Division 2 Patents Court, Case No. HC12C03487 regarding EP (UK) 1 210 115. Defendant's Reply to the Claimant's Pleading of Matters Falling within the Common General Knowledge, Date: Oct. 29, 2013 (17 pages).
*Hospira* v. *Genentech* trial in the High Court of Justice Chancery Division 2 Patents Court, Case No. HC12C03487 regarding EP (UK) 1 210 115. Witness Statement of Simon Charles Cohen, Date: Nov. 18, 2013 (5 pages).
*Hospira* v. *Genentech* trial in the High Court of Justice Chancery Division 2 Patents Court, Case No. HC12C03487 regarding EP (UK) 1 210 115. Exhibit SCC-1, Correspondence between Taylor Wessing and Marks & Clerk regarding slide presentation of Dr. Leyland-Jones, in Witness Statement of Simon Charles Cohen, Date: Nov. 18, 2013 (9 pages).

(56) References Cited

OTHER PUBLICATIONS

*Hospira* v. *Genentech* trial in the High Court of Justice Chancery Division 2 Patents Court, Case No. HC12C03487 regarding EP (UK) 1 210 115. Second Witness Statement of Michael John Gilbert, Date: Nov. 22, 2013 (4 pages).

*Hospira* v. *Genentech* trial in the High Court of Justice Chancery Division 2 Patents Court, Case No. HC12C03487 regarding EP (UK) 1 210 115. Exhibit MJG-7, Correspondence between Taylor Wessing and Marks & Clerk regarding slide presentation of Dr. Leyland-Jones in Second Witness Statement of Michael John Gilbert, Date: Nov. 22, 2013 (6 pages).

*Hospira* v. *Genentech* trial in the High Court of Justice Chancery Division 2 Patents Court, Case No. HC12C03487 regarding EP (UK) 1 210 115. Claimant's Skeleton Argument for Letter of Request Application for Examination of Brian Leyland-Jones, Date: Nov. 26, 2013 (7 pages).

*Hospira* v. *Genentech* trial in the High Court of Justice Chancery Division 2 Patents Court, Case No. HC12C03487 regarding EP (UK) 1 210 115. Defendant's Skeleton Argument for Letter of Request Application for Examination of Brian Leyland-Jones, Date: Nov. 26, 2013 (6 pages).

*Hospira* v. *Genentech* trial in the High Court of Justice Chancery Division 2 Patents Court, Case No. HC12C03487 regarding EP (UK) 1 210 115. Transcript of Hearing for Letter of Request Application for Examination of Brian Leyland-Jones, Date: Nov. 26, 2013 (8 pages).

*Hospira* v. *Genentech* trial in the High Court of Justice Chancery Division 2 Patents Court, Case No. HC12C03487 regarding EP (UK) 1 210 115. Order Directing Issuance of Letter of Request Application for Examination of Brian Leyland-Jones, Date: Nov. 28, 2013 (3 pages).

*Hospira* v. *Genentech* trial in the High Court of Justice Chancery Division 2 Patents Court, Case No. HC12C03487 regarding EP (UK) 1 210 115. Expert Report of Professor Peter Barrett-Lee, Date: Dec. 18, 2013 (43 pages).

*Hospira* v. *Genentech* trial in the High Court of Justice Chancery Division 2 Patents Court, Case No. HC12C03487 regarding EP (UK) 1 210 115. Exhibit PBL-1, CV of Professor Robert Barrett-Lee, in Expert Report of Professor Peter Barrett-Lee, Date: Dec. 18, 2013 (8 pages).

*Hospira* v. *Genentech* trial in the High Court of Justice Chancery Division 2 Patents Court, Case No. HC12C03487 regarding EP (UK) 1 210 115. Exhibit PBL-2, List of Publications Authored or Co-Authored by Professor Robert Barrett-Lee, in Expert Report of Professor Peter Barrett-Lee, Date: Dec. 18, 2013 (8 pages).

*Hospira* v. *Genentech* trial in the High Court of Justice Chancery Division 2 Patents Court, Case No. HC12C03487 regarding EP (UK) 1 210 115. Exhibit PBL-3, Publication of European Patent Specification, Patent No. EP 1 210 115 B1, Published Aug. 5, 2009, in Expert Report of Professor Peter Barrett-Lee, Date: Dec. 18, 2013 (51 pages).

*Hospira* v. *Genentech* trial in the High Court of Justice Chancery Division 2 Patents Court, Case No. HC12C03487 regarding EP (UK) 1 210 115. Expert Report of Alan Vincent Boddy, Date: Dec. 18, 2013 (57 pages).

*Hospira* v. *Genentech* trial in the High Court of Justice Chancery Division 2 Patents Court, Case No. HC12C03487 regarding EP (UK) 1 210 115. Exhibit, AVB-1, Curriculum Vitae of Professor Alan Vincent Boddy, in Expert Report of Professor Alan Vincent Boddy, Date: Dec. 18, 2013 (4 pages).

*Hospira* v. *Genentech* trial in the High Court of Justice Chancery Division 2 Patents Court, Case No. HC12C03487 regarding EP (UK) 1 210 115. Exhibit, AVB-2, List of Publications Authored and Co-Authored by Professor Alan Vincent Boddy, in Expert Report of Professor Alan Vincent Boddy, Date: Dec. 18, 2013 (13 pages).

*Hospira* v. *Genentech* trial in the High Court of Justice Chancery Division 2 Patents Court, Case No. HC12C03487 regarding EP (UK) 1 210 115. Exhibit, AVB-3, List of patents and patent applications in which Alan Boddy is a named inventor, in Expert Report of Professor Alan Vincent Boddy, Date: Dec. 18, 2013 (3 pages).

*Hospira* v. *Genentech* trial in the High Court of Justice Chancery Division 2 Patents Court, Case No. HC12C03487 regarding EP (UK) 1 210 115. Exhibit, AVB-4, Schedule of Sources for Figures, in Expert Report of Professor Alan Vincent Boddy, Date: Dec. 18, 2013 (3 pages).

*Hospira* v. *Genentech* trial in the High Court of Justice Chancery Division 2 Patents Court, Case No. HC12C03487 regarding EP (UK) 1 210 115. Exhibit, AVB-5, WinNoLin output file regarding one-compartment analysis, in Expert Report of Professor Alan Vincent Boddy, Date: Dec. 18, 2013 (13 pages).

*Hospira* v. *Genentech* trial in the High Court of Justice Chancery Division 2 Patents Court, Case No. HC12C03487 regarding EP (UK) 1 210 115. Exhibit, AVB-6, WinNoLin output file regarding analysis incorporating data from figure 3, in Expert Report of Professor Alan Vincent Boddy, Date: Dec. 18, 2013 (13 pages).

*Hospira* v. *Genentech* trial in the High Court of Justice Chancery Division 2 Patents Court, Case No. HC12C03487 regarding EP (UK) 1 210 115. Exhibit, AVB-7, WinNoLin output file regarding two-compartment analysis of data from Table 2, in Expert Report of Professor Alan Vincent Boddy, Date: Dec. 18, 2013 (13 pages).

*Hospira* v. *Genentech* trial in the High Court of Justice Chancery Division 2 Patents Court, Case No. HC12C03487 regarding EP (UK) 1 210 115. Exhibit, AVB-8, WinNoLin output file regarding two-compartment analysis of data from Table 2 and Table 3, in Expert Report of Professor Alan Vincent Boddy, Date: Dec. 18, 2013 (13 pages).

*Hospira* v. *Genentech* trial in the High Court of Justice Chancery Division 2 Patents Court, Case No. HC12C03487 regarding EP (UK) 1 210 115. Exhibit, AVB-9, Output of data underlying Figure 26, in Expert Report of Professor Alan Vincent Boddy, Date: Dec. 18, 2013 (100 pages).

*Hospira* v. *Genentech* trial in the High Court of Justice Chancery Division 2 Patents Court, Case No. HC12C03487 regarding EP (UK) 1 210 115. Expert Report of Professor Robert Charles Frederick Leonard, Date: Dec. 18, 2013 (32 pages).

*Hospira* v. *Genentech* trial in the High Court of Justice Chancery Division 2 Patents Court, Case No. HC12C03487 regarding EP (UK) 1 210 115. Exhibit RFCL-1, Curriculum Vitae of Robert Charles Frederick Leonard dated Oct. 2012, in Expert Report of Professor Robert Charles Frederick Leonard, Date: Dec. 18, 2013 (42 pages).

*Hospira* v. *Genentech* trial in the High Court of Justice Chancery Division 2 Patents Court, Case No. HC12C03487 regarding EP (UK) 1 210 115. Exhibit RFCL-2, Devita, et. al., "Therapy of Locally Advanced and Inflammatory Breast Cancer", Cancer: Principles & Practices of Oncology, Caputo, Grace R., Lippincott-Raven Publishers, 5$^{th}$ Edition, 1997, p. 1599, in Expert Report of Professor Robert Charles Frederick Leonard, Date: Dec. 18, 2013 (3 pages).

*Hospira* v. *Genentech* trial in the High Court of Justice Chancery Division 2 Patents Court, Case No. HC12C03487 regarding EP (UK) 1 210 115. Exhibit RFCL-3, Taylor, et. al., "The therapeutic potential of novel aromatase inhibitors in breast cancer", Exp. Opin. Invest. Drugs, Mar. 1999, vol. 8, No. 3, pp. 269-279, in Expert Professor Robert Charles Frederick Leonard, Date: Dec. 18, 2013 (11 pages).

*Hospira* v. *Genentech* trial in the High Court of Justice Chancery Division 2 Patents Court, Case No. HC12C03487 regarding EP (UK) 1 210 115. Exhibit RFCL-4, Blainey, R. W., "The Role of Selective Non-Steroidal Aromatase Inhibitors in Future Treatment Strategies", Oncology, 1997, vol. 54, Suppl. 2, pp. 27-31, in Expert Report of Professor Robert Charles Frederick Leonard, Date: Dec. 18, 2013 (5 pages).

*Hospira* v. *Genentech* trial in the High Court of Justice Chancery Division 2 Patents Court, Case No. HC12C03487 regarding EP (UK) 1 210 115. Exhibit RFCL-5, Dixon, et. al., "Lessons from the use of aromatase inhibitors in the neoadjuvant setting", Endocrine Related Cancer, 1999, vol. 6, pp. 227-230 in Expert Report of Professor Robert Charles Frederick Leonard, Date: Dec. 18, 2013 (5 pages).

(56) References Cited

OTHER PUBLICATIONS

*Hospira* v. *Genentech* trial in the High Court of Justice Chancery Division 2 Patents Court, Case No. HC12C03487 regarding EP (UK) 1 210 115. Exhibit RFCL-6, ATAC Trialists' Group, "Anastrozole alone or in combination with tamoxifen versus tamoxifen alone for adjuvant treatment of postmenopausal women with early breast cancer: first results of the ATAC randomized trial", Lancet, 2002, vol. 159, pp. 2131-2139, in Expert Report of Professor Robert Charles Frederick Leonard, Date: Dec. 18, 2013 (9 pages).

*Hospira* v. *Genentech* trial in the High Court of Justice Chancery Division 2 Patents Court, Case No. HC12C03487 regarding EP (UK) 1 210 115. Exhibit RFCL-9, Slamon, et. al., "Addition of Herceptin (Humanized Anti-Her2 Antibody) for HER2 Overexpressing Metastatic Breast Cancer (HER2+/MBC) Markedly Increases Anticancer Activity: A Randomised, Multinational Controlled Phase III Trial", Proceedings of ASCO, 1998, vol. 17, Abstract #377, p. 98A, in Expert Report of Professor Robert Charles Frederick Leonard, Date: Dec. 18, 2013 (5 pages).

*Hospira* v. *Genentech* trial in the High Court of Justice Chancery Division 2 Patents Court, Case No. HC12C03487 regarding EP (UK) 1 210 115. Expert Report of Dr. Robert Howard Earhart, Date: Dec. 18, 2013 (39 pages).

*Hospira* v. *Genentech* trial in the High Court of Justice Chancery Division 2 Patents Court, Case No. HC12C03487 regarding EP (UK) 1 210 115. Exhibit RHE-1, Curriculum Vitae of Robert Howard Earhart, in Expert Report of Dr. Robert Howard Earhart, Date: Dec. 18, 2013 (16 pages).

*Hospira* v. *Genentech* trial in the High Court of Justice Chancery Division 2 Patents Court, Case No. HC12C03487 regarding EP (UK) 1 210 115. Exhibit RHE-2, Baselga, et. al., "Phase II Study of Weekly Intravenous Recombinant Humanized Anti-p185$^{HER2}$ Monoclonal Antibody in Patients with HER2/neu-Overexpressing Metastatic Breast Cancer", Journal of Clinical Oncology, Mar. 1996, vol. 14, No. 3, pp. 737-744, in Expert Report of Dr. Robert Howard Earhart, Date: Dec. 18, 2013 (8 pages).

*Hospira* v. *Genentech* trial in the High Court of Justice Chancery Division 2 Patents Court, Case No. HC12C03487 regarding EP (UK) 1 210 115. Exhibit RHE-3, Pegram, et. al., "Phase II Study of Receptor-Enhanced Chemosensitivity Using Recombinant Humanized Anti-p185$^{HER2/neu}$ Monoclonal Antibody Plus Cisplatin in Patients with HER2/neu-Overexpressing Metastatic Breast Cancer Refractory to Chemotherapy Treatment", Journal of Clinical Oncology, Aug. 1998. vol. 16, No. 8, pp. 2659-2671, in Expert Report of Dr. Robert Howard Earhart, Date: Dec. 18, 2013 (8 pages).

*Hospira* v. *Genentech* trial in the High Court of Justice Chancery Division 2 Patents Court, Case No. HC12C03487 regarding EP (UK) 1 210 115. Order dispensing with expert meetings and joint reports, Date: Jan. 16, 2014 (2 pages).

*Hospira* v. *Genentech* trial in the High Court of Justice Chancery Division 2 Patents Court, Case No. HC12C03487 regarding EP (UK) 1 210 115. Second Expert Report of Professor Peter Barrett-Lee, Date: Jan. 24, 2014 (4 pages).

*Hospira* v. *Genentech* trial in the High Court of Justice Chancery Division 2 Patents Court, Case No. HC12C03487 regarding EP (UK) 1 210 115. Second Expert Report of Alan Vincent Boddy, Date: Jan. 24, 2014 (24 pages).

*Hospira* v. *Genentech* trial in the High Court of Justice Chancery Division 2 Patents Court, Case No. HC12C03487 regarding EP (UK) 1 210 115. Second Expert Report of Professor Robert Charles Frederick Leonard, Date: Jan. 24, 2014 (3 pages).

*Hospira* v. *Genentech* trial in the High Court of Justice Chancery Division 2 Patents Court, Case No. HC12C03487 regarding EP (UK) 1 210 115. Second Expert Report of Dr. Robert Howard Earhart, Date: Jan. 24, 2014 (9 pages).

Transcript of Deposition of Brian Leyland-Jones dated Jan. 27, 2014 (92 pages).

Exhibit 1 from Jan. 27, 2014 Deposition of Brian Leyland-Jones. Subpoena for Dr. Leyland-Jones, (10 pages).

Exhibit 2 from Jan. 27, 2014 Deposition of Brian Leyland-Jones. Undated slide deck titled "Pharmacological/Screening Insights into the Future of Herceptin." (34 pages).

Exhibit 3 from Jan. 27, 2014 Deposition of Brian Leyland-Jones. Undated slide deck titled "Dose-Scheduling: Herceptin®." (42 pages).

Exhibit 4 from Jan. 27, 2014 Deposition of Brian Leyland-Jones. Meta data on electronic files for Exhibits 2 and 3. (2 pages).

Exhibit 5 from Jan. 27, 2014 Deposition of Brian Leyland-Jones. "HER2 State-of-the Art." (26 pages).

Exhibit 6 from Jan. 27, 2014 Deposition of Brian Leyland-Jones. HER2 State-of-the-Art Conference Report Nov. 21-23, 1999, Workshop Proceedings, from the *Annals of Oncology*, vol. 12, 6 supplement 1, 2001. (10 pages).

Exhibit 7 from Jan. 27, 2014 Deposition of Brian Leyland-Jones. Leyland-Jones, "Dose Scheduling—Herceptin®," *Oncology*, 2001; 61 (suppl 2):31-36.

Exhibit 8 from Jan. 27, 2014 Deposition of Brian Leyland-Jones. "Pharmacokinetics: Safety and efficacy of trastuzumab administered every three weeks in combination with paclitaxel" *Journal of Clinical Oncology*, 2003, vol. 21, 3965-3971.

Exhibit 9 from Jan. 27, 2014 Deposition of Brian Leyland-Jones. Face page of a publication titled "Optimising the Role of Herceptin in Breast Cancer." (1 page).

Undated slide deck titled: "Pharmacological/Screening Insights into the Future of Herceptin." (28 pages).

Undated slide deck titled: "Optimising the role of Herceptin® in breast cancer." (87 pages).

*Hospira* v. *Genentech* trial in the High Court of Justice Chancery Division 2 Patents Court, Case No. HC12C03487 regarding EP (UK) 1 210 115. Second Witness Statement of Simon Charles Cohen, Date: Jan. 27, 2014 (12 pages).

*Hospira* v. *Genentech* trial in the High Court of Justice Chancery Division 2 Patents Court, Case No. HC12C03487 regarding EP (UK) 1 210 115. Exhibit SCC-2, inter partes correspondence with regard to independently valid claims, in Second Witness Statement of Simon Charles Cohen, Date: Jan. 27, 2014 (3 pages).

*Hospira* v. *Genentech* trial in the High Court of Justice Chancery Division 2 Patents Court, Case No. HC12C03487 regarding EP (UK) 1 210 115. Exhibit SCC-3, inter partes correspondence with regard to the declaration of non-infringement, in Second Witness Statement of Simon Charles Cohen, Date: Jan. 27, 2014 (29 pages).

*Hospira* v. *Genentech* trial in the High Court of Justice Chancery Division 2 Patents Court, Case No. HC12C03487 regarding EP (UK) 1 210 115. Exhibit SCC-4, Application Notice, request that Hospira provide further information dated Nov. 23, 2012, in Second Witness Statement of Simon Charles Cohen, Date: Jan. 27, 2014 (6 pages).

*Hospira* v. *Genentech* trial in the High Court of Justice Chancery Division 2 Patents Court, Case No. HC12C03487 regarding EP (UK) 1 210 115. Exhibit SCC-5, Consent Order requesting provision of a confidential statement of case dated Dec. 12, 2012, in Second Witness Statement of Simon Charles Cohen, Date: Jan. 27, 2014 (4 pages).

*Hospira* v. *Genentech* trial in the High Court of Justice Chancery Division 2 Patents Court, Case No. HC12C03487 regarding EP (UK) 1 210 115. Exhibit SCC-6, Confidential Statement of Case Served Pursuant to Court Order dated Dec. 12, 2012, in Second Witness Statement of Simon Charles Cohen, Date: Jan. 27, 2014 (8 pages).

*Hospira* v. *Genentech* trial in the High Court of Justice Chancery Division 2 Patents Court, Case No. HC12C03487 regarding EP (UK) 1 210 115. Exhibit SCC-7, Expert Report of Professor Zhaohui Sunny Zhou dated Dec. 18, 2013, in Second Witness Statement of Simon Charles Cohen, Date: Jan. 27, 2014 (5 pages).

*Hospira* v. *Genentech* trial in the High Court of Justice Chancery Division 2 Patents Court, Case No. HC12C03487 regarding EP (UK) 1 210 115. Exhibit SCC-8, Expert Report of Dr. Uwe Gottschalk dated Dec. 18, 2013, in Second Witness Statement of Simon Charles Cohen, Date: Jan. 27, 2014 (4 pages).

(56) References Cited

OTHER PUBLICATIONS

*Hospira* v. *Genentech* trial in the High Court of Justice Chancery Division 2 Patents Court, Case No. HC12C03487 regarding EP (UK) 1 210 115. Exhibit SCC-9, Second Expert Report of Dr. Uwe Gottschalk dated Dec. 18, 2013, in Second Witness Statement of Simon Charles Cohen, Date: Jan. 27, 2014 (4 pages).
*Hospira* v. *Genentech* trial in the High Court of Justice Chancery Division 2 Patents Court, Case No. HC12C03487 regarding EP (UK) 1 210 115. Exhibit SCC-10, inter partes correspondence with regard to directions for the EP '455 amendment, in Second Witness Statement of Simon Charles Cohen, Date: Jan. 27, 2014 (12 pages).
*Hospira* v. *Genentech* trial in the High Court of Justice Chancery Division 2 Patents Court, Case No. HC12C03487 regarding EP (UK) 1 210 115. Exhibit SCC-11, Comptroller's objections to claim set 2 dated Nov. 26, 2013, in Second Witness Statement of Simon Charles Cohen, Date: Jan. 27, 2014 (4 pages).
*Hospira* v. *Genentech* trial in the High Court of Justice Chancery Division 2 Patents Court, Case No. HC12C03487 regarding EP (UK) 1 210 115. Exhibit SCC-12, Draft Trial Timetable, in Second Witness Statement of Simon Charles Cohen, Date: Jan. 27, 2014 (2 pages).
*Hospira* v. *Genentech* trial in the High Court of Justice Chancery Division 2 Patents Court, Case No. HC12C03487 regarding EP (UK) 1 210 115. Exhibit SCC-13, inter partes correspondence with regard to costs for EP '632, in Second Witness Statement of Simon Charles Cohen, Date: Jan. 27, 2014 (4 pages).
*Hospira* v. *Genentech* trial in the High Court of Justice Chancery Division 2 Patents Court, Case No. HC12C03487 regarding EP (UK) 1 210 115. Exhibit SCC-14, inter partes correspondence with regard to disclosure of documents, in Second Witness Statement of Simon Charles Cohen, Date: Jan. 27, 2014 (16 pages).
*Hospira* v. *Genentech* trial in the High Court of Justice Chancery Division 2 Patents Court, Case No. HC12C03487 regarding EP (UK) 1 210 115. Hospira's Skeleton Argument for the Pre-Trial Review, Date: Jan. 29, 2014 (15 pages).
*Hospira* v. *Genentech* trial in the High Court of Justice Chancery Division 2 Patents Court, Case No. HC12C03487 regarding EP (UK) 1 210 115. Genentech's Skeleton Argument for the Pre-Trial Review, Date: Jan. 29, 2014 (8 pages).
*Hospira* v. *Genentech* trial in the High Court of Justice Chancery Division 2 Patents Court, Case No. HC12C03487 regarding EP (UK) 1 210 115. Claimant's Civil Evidence Act Notice, Date: Jan. 2014 (3 pages).
*Hospira* v. *Genentech* trial in the High Court of Justice Chancery Division 2 Patents Court, Case No. HC12C03487 regarding EP (UK) 1 210 115. Approved Judgement—Pre-trial review, Date: Jan. 2014 (6 pages).
*Hospira* v. *Genentech* trial in the High Court of Justice Chancery Division 2 Patents Court, Case No. HC12C03487 regarding EP (UK) 1 210 115. Order from Pre-trial review, Date: Jan. 30, 2014 (6 pages).
*Hospira* v. *Genentech* trial in the High Court of Justice Chancery Division 2 Patents Court, Case No. HC12C03487 regarding EP (UK) 1 210 115. Transcript of the Pre-trial Review, Date: Jan. 30, 2014 (63 pages).
*Hospira* v. *Genentech* trial in the High Court of Justice Chancery Division 2 Patents Court, Case No. HC12C03487 regarding EP (UK) 1 210 115. Defendant's Statement of Case on Independent Validity, Date: Feb. 10, 2014 (4 pages).
*Hospira* v. *Genentech* trial in the High Court of Justice Chancery Division 2 Patents Court, Case No. HC12C03487 regarding EP (UK) 1 210 115. Third Expert Report of Professor Peter Barrett-Lee, Date: Feb. 10, 2014 (3 pages).
*Hospira* v. *Genentech* trial in the High Court of Justice Chancery Division 2 Patents Court, Case No. HC12C03487 regarding EP (UK) 1 210 115. Third Expert Report of Alan Vincent Boddy, Date: Feb. 10, 2014 (3 pages).

*Hospira* v. *Genentech* trial in the High Court of Justice Chancery Division 2 Patents Court, Case No. HC12C03487 regarding EP (UK) 1 210 115. Third Expert Report of Professor Robert Charles Frederick Leonard, Date: Feb. 10, 2014 (5 pages).
*Hospira* v. *Genentech* trial in the High Court of Justice Chancery Division 2 Patents Court, Case No. HC12C03487 regarding EP (UK) 1 210 115. Third Expert Report of Dr. Robert Howard Earhart, Date: Feb. 10, 2014 (18 pages).
*Hospira* v. *Genentech* trial in the High Court of Justice Chancery Division 2 Patents Court, Case No. HC12C03487 regarding EP (UK) 1 210 115. Exhibit RHE-4, WinNoLin analysis using Model 8, in Third Expert Report of Dr. Robert Howard Earhart, Date: Feb. 10, 2014 (12 pages).
*Hospira* v. *Genentech* trial in the High Court of Justice Chancery Division 2 Patents Court, Case No. HC12C03487 regarding EP (UK) 1 210 115. Exhibit RHE-5, WinNoLin analysis using Model 1, in Third Expert Report of Dr. Robert Howard Earhart, Date: Feb. 10, 2014 (12 pages).
*Hospira* v. *Genentech* trial in the High Court of Justice Chancery Division 2 Patents Court, Case No. HC12C03487 regarding EP (UK) 1 210 115. Exhibit RHE-6, Except from Biological Licensing Application submitted to the FDA, May 1, 1998, p. 14, in Third Expert Report of Dr. Robert Howard Earhart, Date: Feb. 10, 2014 (1 page).
*Hospira* v. *Genentech* trial in the High Court of Justice Chancery Division 2 Patents Court, Case No. HC12C03487 regarding EP (UK) 1 210 115. Exhibit RHE-8, Simulation of alternative dosing regimens, May 21, 1998, in Third Expert Report of Dr. Robert Howard Earhart, Date: Feb. 10, 2014 (10 pages).
*Hospira* v. *Genentech* trial in the High Court of Justice Chancery Division 2 Patents Court, Case No. HC12C03487 regarding EP (UK) 1 210 115. Exhibit RHE-9, Simulation of alternative dosing regimens, May 22, 1998, in Third Expert Report of Dr. Robert Howard Earhart, Date: Feb. 10, 2014 (10 pages).
*Hospira* v. *Genentech* trial in the High Court of Justice Chancery Division 2 Patents Court, Case No. HC12C03487 regarding EP (UK) 1 210 115. Exhibit RHE-10, Excerpt of letter sent by Genentech to the FDA, Feb. 20, 2001, in Third Expert Report of Dr. Robert Howard Earhart, Date: Feb. 10, 2014 (9 pages).
*Hospira* v. *Genentech* trial in the High Court of Justice Chancery Division 2 Patents Court, Case No. HC12C03487 regarding EP (UK) 1 210 115, Claimant's Response to Defendant's Statement of Case on Independent Validity, Date: Feb. 17, 2014 (3 pages).
*Hospira* v. *Genentech* trial in the High Court of Justice Chancery Division 2 Patents Court, Case No. HC12C03487 regarding EP (UK) 1 210 115. Genentech's Skeleton Argument, Date: Feb. 27, 2014 (37 pages).
*Hospira* v. *Genentech* trial in the High Court of Justice Chancery Division 2 Patents Court, Case No. HC12C03487 regarding EP (UK) 1 210 115. Hospira's Skeleton Argument, Date: Feb. 28, 2014 (61 pages).
*Hospira* v. *Genentech* trial in the High Court of Justice Chancery Division 2 Patents Court, Case No. HC12C03487 regarding EP (UK) 1 210 115. Genentech's Supplemental Skeleton Argument, Date: Mar. 4, 2014 (4 pages).
*Hospira* v. *Genentech* trial in the High Court of Justice Chancery Division 2 Patents Court, Case No. HC12C03487 regarding EP (UK) 1 210 115. Transcript of UK Patents Court Trial (Days 1-9), Date: Mar. 6-19, 2014 (487 pages).
*Hospira* v. *Genentech* trial in the High Court of Justice Chancery Division 2 Patents Court, Case No. HC12C03487 regarding EP (UK) 1 210 115. Hospira's Written Closing, Date: Mar. 17, 2014 (60 pages).
*Hospira* v. *Genentech* trial in the High Court of Justice Chancery Division 2 Patents Court, Case No. HC12C03487 regarding EP (UK) 1 210 115. Genentech's Closing Submissions, Date: Mar. 17, 2014 (86 pages).
*Hospira* v. *Genentech* trial in the High Court of Justice Chancery Division 2 Patents Court, Case No. HC12C03487 regarding EP (UK) 1 210 115. Consent Order for suspending time to appeal, Date: Apr. 10, 2014 (2 pages).

(56) References Cited

OTHER PUBLICATIONS

*Hospira* v. *Genentech* trial in the High Court of Justice Chancery Division 2 Patents Court, Case No. HC12C03487 regarding EP (UK) 1 210 115. Approved Judgement, Date: Apr. 10, 2014 (47 pages).
*Hospira* v. *Genentech* trial in the High Court of Justice Chancery Division 2 Patents Court, Case No. HC12C03487 regarding EP (UK) 1 210 115. Third Witness Statement of Simon Charles Cohen, Date: May 2, 2014 (9 pages).
*Hospira* v. *Genentech* trial in the High Court of Justice Chancery Division 2 Patents Court, Case No. HC12C03487 regarding EP (UK) 1 210 115. Fourth Witness Statement of Simon Charles Cohen, Date: May 13, 2014 (5 pages).
*Hospira* v. *Genentech* trial in the High Court of Justice Chancery Division 2 Patents Court, Case No. HC12C03487 regarding EP (UK) 1 210 115. Exhibit SCC-15, Letter from Marks & Clerk regarding draft order and supporting evidence dated Apr. 26, 2014, in Fourth Witness Statement of Simon Charles Cohen, Date: May 13, 2014 (2 pages).
*Hospira* v. *Genentech* trial in the High Court of Justice Chancery Division 2 Patents Court, Case No. HC12C03487 regarding EP (UK) 1 210 115. Exhibit SCC-16, Letter from Marks & Clerk requesting further information and clarification regarding statement of costs dated May 9, 2014, in Fourth Witness Statement of Simon Charles Cohen, Date: May 13, 2014 (3 pages).
*Hospira* v. *Genentech* trial in the High Court of Justice Chancery Division 2 Patents Court, Case No. HC12C03487 regarding EP (UK) 1 210 115. Exhibit SCC-17, Breakdown of costs incurred by Hospira, in Fourth Witness Statement of Simon Charles Cohen, Date: May 13, 2014 (2 pages).
*Hospira* v. *Genentech* trial in the High Court of Justice Chancery Division 2 Patents Court, Case No. HC12C03487 regarding EP (UK) 1 210 115. Third Witness Statement of Michael John Gilbert, Date: May 13, 2014 (10 pages).
*Hospira* v. *Genentech* trial in the High Court of Justice Chancery Division 2 Patents Court, Case No. HC12C03487 regarding EP (UK) 1 210 115. Exhibit MJC-8, Letter from Marks & Clerk requesting a limited breakdown of global costs dated May 9, 2014, in Third Witness Statement of Michael John Gilbert, Date: May 13, 2014 (3 pages).
*Hospira* v. *Genentech* trial in the High Court of Justice Chancery Division 2 Patents Court, Case No. HC12C03487 regarding EP (UK) 1 210 115. Exhibit MJC-9, inter partes correspondence regarding declaration about construction, in Third Witness Statement of Michael John Gilbert, Date: May 13, 2014 (53 pages).
*Hospira* v. *Genentech* trial in the High Court of Justice Chancery Division 2 Patents Court, Case No. HC12C03487 regarding EP (UK) 1 210 115. Genentech's Skeleton Argument on the Final Order, Date: May 14, 2014 (9 pages).
*Hospira* v. *Genentech* trial in the High Court of Justice Chancery Division 2 Patents Court, Case No. HC12C03487 regarding EP (UK) 1 210 115. Fourth Witness Statement of Michael John Gilbert, Date: May 15, 2014 (6 pages).
*Hospira* v. *Genentech* trial in the High Court of Justice Chancery Division 2 Patents Court, Case No. HC12C03487 regarding EP (UK) 1 210 115. Exhibit MJC-10, Roche Media Release, "Roche delivers strong 2013 results" dated Jan. 30, 2014, in Fourth Witness Statement of Michael John Gilbert, Date: May 15, 2014 (3 pages).
*Hospira* v. *Genentech* trial in the High Court of Justice Chancery Division 2 Patents Court, Case No. HC12C03487 regarding EP (UK) 1 210 115. Hospira's Skeleton Argument for the form-of-order hearing, Date: May 16, 2014 (15 pages).
*Hospira* v. *Genentech* trial in the High Court of Justice Chancery Division 2 Patents Court, Case No. HC12C03487 regarding EP (UK) 1 210 115. Approved Judgement—Costs, Date: May 16, 2014 (10 pages).
*Hospira* v. *Genentech* trial in the High Court of Justice Chancery Division 2 Patents Court, Case No. HC12C03487 regarding EP (UK) 1 210 115. Approved Judgement—Confidentiality of Documents, Date: May 16, 2014 (9 pages).

*Hospira* v. *Genentech* trial in the High Court of Justice Chancery Division 2 Patents Court, Case No. HC12C03487 regarding EP (UK) 1 210 115. Transcript of Form of Order Hearing, Date: May 16, 2014 (26 pages).
*Hospira* v. *Genentech* trial in the High Court of Justice Chancery Division 2 Patents Court, Case No. HC12C03487 regarding EP (UK) 1 210 115. Genentech's Skeleton Argument for Petition to Appeal, Date: Jun. 6, 2014 (17 pages).
*Hospira* v. *Genentech* trial in the High Court of Justice Chancery Division 2 Patents Court, Case No. HC12C03487 regarding EP (UK) 1 210 115. Notice of Appeal and Grounds of Appeal, Date: Jun. 6, 2014 (12 pages).
*Hospira* v. *Genentech* trial in the High Court of Justice Chancery Division 2 Patents Court, Case No. HC12C03487 regarding EP (UK) 1 210 115. Defendant's list of documents: standard disclosure, Date: Jun. 13, 2014 (12 pages).
*Hospira* v. *Genentech* trial in the High Court of Justice Chancery Division 2 Patents Court, Case No. HC12C03487 regarding EP (UK) 1 210 115. Defendant's supplemental list of documents: standard disclosure, Date: Jun. 13, 2014 (12 pages).
*Hospira* v. *Genentech* trial in the High Court of Justice Chancery Division 2 Patents Court, Case No. HC12C03487 regarding EP (UK) 1 210 115. Claimant's list of documents: standard disclosure, Date: Jun. 14, 2014 (3 pages).
*Hospira* v. *Genentech* trial in the High Court of Justice Chancery Division 2 Patents Court, Case No. HC12C03487 regarding EP (UK) 1 210 115. Fifth Witness Statement of Simon Charles Cohen, Date: Jul. 9, 2014 (8 pages).
*Hospira* v. *Genentech* trial in the High Court of Justice Chancery Division 2 Patents Court, Case No. HC12C03487 regarding EP (UK) 1 210 115. Exhibit SCC-18, Decision of Opposition Division regarding '115 patent dated May 4, 2012, in Fifth Witness Statement of Simon Charles Cohen, Date: Jul. 9, 2014 (16 pages).
*Hospira* v. *Genentech* trial in the High Court of Justice Chancery Division 2 Patents Court, Case No. HC12C03487 regarding EP (UK) 1 210 115. Exhibit SCC-19, Proprietor's Grounds of Appeal regarding '115 patent dated Sep. 13, 2012, in Fifth Witness Statement of Simon Charles Cohen, Date: Jul. 9, 2014 (41 pages).
*Hospira* v. *Genentech* trial in the High Court of Justice Chancery Division 2 Patents Court, Case No. HC12C03487 regarding EP (UK) 1 210 115. Order granting permission to appeal, Date: Jul. 21, 2014 (2 pages).
*Hospira* v. *Genentech* trial in the High Court of Justice Chancery Division 2 Patents Court, Case No. HC12C03487 regarding EP (UK) 1 210 115. Genentech's Skeleton Argument for hearing on Jul. 22, 2014, Date: Jul. 21, 2014 (6 pages).
*Hospira* v. *Genentech* trial in the High Court of Justice Chancery Division 2 Patents Court, Case No. HC12C03487 regarding EP (UK) 1 210 115. Hospira's Confidential Skeleton Argument, Date: Jul. 21, 2014 (11 pages).
*Hospira* v. *Genentech* trial in the High Court of Justice Chancery Division 2 Patents Court, Case No. HC12C03487 regarding EP (UK) 1 210 115. Transcript of Confidentiality Hearing, Date: Jul. 22, 2014 (23 pages).
*Hospira* v. *Genentech* trial in the High Court of Justice Chancery Division 2 Patents Court, Case No. HC12C03487 regarding EP (UK) 1 210 115. Order of Confidentiality, Date: Jul. 22, 2014 (3 pages).
*Hospira* v. *Genentech* trial in the High Court of Justice Chancery Division 2 Patents Court, Case No. HC12C03487 regarding EP (UK) 1 210 115. Respondent's Notice for Upholding Revocation Order and Grounds for Upholding Revocation Order, Date: Aug. 6, 2014 (11 pages).
*Hospira* v. *Genentech* trial in the High Court of Justice Chancery Division 2 Patents Court, Case No. HC12C03487 regarding EP (UK) 1 210 115. Genentech's Skeleton Argument on the Appeal, Date: Nov. 7, 2014 (29 pages).
*Hospira* v. *Genentech* trial in the High Court of Justice Chancery Division 2 Patents Court, Case No. HC12C03487 regarding EP (UK) 1 210 115. Skeleton Argument of the Respondent (Hospira), Date: Dec. 15, 2014 (26 pages).

(56) References Cited

OTHER PUBLICATIONS

*Hospira* v. *Genentech* trial in the High Court of Justice Chancery Division 2 Patents Court, Case No. HC12C03487 regarding EP (UK) 1 210 115. Transcript of Appeal Proceedings, Day 1, Date: Jan. 2015 (61 pages).
*Hospira* v. *Genentech* trial in the High Court of Justice Chancery Division 2 Patents Court, Case No. HC12C03487 regarding EP (UK) 1 210 115. Transcript of Appeal Proceedings, Day 2, Date: Jan. 14, 2015 (40 pages).
*Hospira* v. *Genentech* trial in the High Court of Justice Chancery Division 2 Patents Court, Case No. HC12C03487 regarding EP (UK) 1 210 115. Order dismissing appeal, Date: Feb. 6, 2015 (2 pages).
Coates, et. al., "On the Receiving End—Patient Perception of the Side-effects of Cancer Chemotherapy", Eur. J. Cancer Clin. Oncol., 1983, vol. 19, No. 2, pp. 203-208.
Hainsworth, et. al., "Paclitaxel Administered by 1-Hour Infusion: Preliminary Results of a Phase I/II Trial Comparing Two Schedules", Cancer, Aug. 1994, vol. 74, No. 4, pp. 1377-1382.
Griffin, et. al., "On the receiving end V: Patient Perceptions of the side effects of cancer chemotherapy in 1993", Annals of Oncology, 1996, vol. 7, pp. 189-195.
DeMario, et. al., "Oral Chemotherapy: Rationale and Future Directions", Journal of Clinical Oncology, Jul. 1998, vol. 16, No. 7, pp. 2557-2567.
Barrett-Lee, et. al., "An audit to determine the time taken to administer intravenous bisphosphonate infusions in patients diagnosed with metastatic breast cancer to bone in a hospital setting", Current Medical Research and Opinions, 2007, vol. 23, No. 7, pp. 1575-1582.
Pivot, et. al., "Preference for subcutaneous or intravenous administration of trastuzumab in patients with HER2-positive early breast cancer (PrefHer): an open-label randomized study", Lancet Oncology, Sep. 2013, vol. 14, pp. 962-970.
Figure 24.1—α and β phase (1 page).
Pharmacokinetic calculations (5 pages).
Earhart, Robert H., "Docetaxel (Taxotere): Preclinical and General Clinical Information", Seminars in Oncology, Oct. 1999, vol. 26, No. 5, Suppl. 17, pp. 8-13.
Perez, Edith A., "Paclitaxel in Breast Cancer", The Oncologist, 1998, vol. 3, pp. 373-389.
Seidman, et. al., "Dose-Dense Therapy with Weekly 1-Hour Paclitaxel Infusions in the Treatment of Metastatic Breast Cancer", Journal of Clinical Oncology, 1998, vol. 16, No. 10, pp. 3353-3361.
Decision Institution of Inter Partes Review (Paper 13), Case IPR2017-00804 re: U.S. Pat. No. 6627196, entered Jul. 27, 2017 (15 pages).
Decision Institution of Inter Partes Review (Paper 13), Case IPR2017-00805 re: U.S. Pat. No. 7371379, entered on Jul. 27, 2017 (17 pages).
Decision of the Technical Boards of Appeal of the European Patent Office relating to EP1210115, dated Jul. 24, 2017 (27 pages).
Decision of IMPI Ex-Officio Cancellation Action Initiated by IMPI against Mexican Patent No. 259512, dated Apr. 26, 2017, in Spanish with English translation (51 pages).
Board of Appeal Decision re Nullity Action No. 2016-800071 filed by Celltrion Incorporated and Pfizer Holdings G.K. against Japanese U.S. Pat. No. 5,818,545, dated Jul. 5, 2017, in Japanese (126 pages) with English Translation (126 pages).
Board Communication, Jan. 3, 2018, EP Patent No. 09008313.0 / 2111870, Appeal No. T2363/13-3.3.04 (44 pages).
Decision Institution of Inter Partes Review (Paper 12), IPR2017-01139 re: U.S. Pat. No. 6,627,196 (Baughman, et al., "Dosages for treatment with anti-ErbB2 antibodies"), entered Oct. 4, 2017 (17 pages).
Decision Institution of Inter Partes Review (Paper 12), IPR2017-01140 re: U.S. Pat. No. 7,371,379 (Baughman, et al., "Dosages for treatment with anti-ErbB2 antibodies"), entered Oct. 4, 2017 (18 pages).

Kempeni et al., "Preliminary Results of early clinical trials with the fully human anti-TNFα monoclonal antibody D2E7" Ann Rheum Dis 58(Suppl I):170-172 ( 1999).
Van de Putte et al., "Efficacy of the Fully Human Anti-TNF Antibody D2E7 in Rheumatoid Arthritis" ACR Abstract Concurrent Session RA: TNF-Blockade, Wednesday, Nov. 17, 1999, 10:30 a.m. to 12:00 p.m., (1999).
Final Written Decision (Paper No. 83), Inter Partes Review, Case No. IPR2017-00804 re: U.S. Pat. No. 6,627,196 B1, *Hospira, Inc., and Samsung Bioepis Co., Ltd.* v. *Genentech, Inc.*, entered on Oct. 3, 2018 (39 pages).
Final Written Decition (Paper No. 83), Inter Partes Review, Case No. IPR2017-00805 re U.S. Pat. No. 7,371,379 B2, entered on Oct. 3, 2018 (39 pages).
Final Written Decision (Paper No. 68), Inter Partes Review, Case No. IPR2017-01139 re: U.S. Pat. No. 6,627,196 B1, *Celltrion, Inc.,* v. *Genentech, Inc.*, entered on Oct. 3, 2018 (31 pages).
Final Written Decision (Paper No. 69), Inter Partes Review, Case No. IPR2017-01140 re: U.S. Pat. No. 7,371,379 B2, *Celltrion, Inc.,* v. *Genentech, Inc.*, entered on Oct. 3, 2018 (31 pages).
Baselga, "Current and Planned Clinical Trials With Trastuzumab (Herceptin)" Seminars in Oncology 27(5 Suppl 9):27-32 (2000).
Zandvliet et al., "Saturable Binding of Indisulam to Plasma Proteins and Distribution to Human Erythrocytes" Drug Metabolism and Disposition 34(6):1041-1046 ( 2006).
Opposition Proceedings regarding European Patent No. EP 1 210 115.
Summons to Attend Oral Hearing in Appeal relating to EP 1 210 115 dated Dec. 2, 2015 (14 pages).
Letter from Genentech regarding Oral Proceedings relating to Opposition to European Patent No. EP 1 210 115 dated Jul. 7, 2016 (2 pages).
Communication of the EPO Board of Appeal pursuant to Article 15(1) of the Rules of Procedure of the Boards of Appeal issued in Opposition to European Patent No. EP 1 210 115 dated Jul. 26, 2016 (21 pages).
Declaration of Professor Alan Vincent Boddy, including Annexes A and B; Date: Aug. 11, 2016 (11 pages).
Declaration of Professor Peter Barrett-Lee, including Exhibits PBL-1 and PBL-2; Date: Aug. 12, 2016 (21 pages).
Third Party Observation filed in accordance with Article 115 EPC in Opposition to European Patent No. EP 1 210 115 dated Sep. 8, 2016 (3 pages).
Minutes of Oral Proceedings, EPO Boards of Appeals Appeal No. T1592/12-3.3.04, held Oct. 25, 2016 in Opposition to European Patent No. EP 1 210 115 dated Oct. 28, 2016 (11 pages).
Hooks, et. al., "Muromonab CD-3: A Review of its Pharmacology, Pharmacokinetics, and Clinical Use in Transplantation", The Journal of Pharmacology and Drug Therapy, 1991, vol. 11, No. 1, pp. 26-37.
Letter from Genentech, Inc. to Dr. Glen D. Jones, Ph.D. of the Food and Drug Administration, dated Feb. 20, 2001 (9 pages).
*Hospira* v. *Genentech* trial in the High Court of Justice Chancery Division 2 Patents Court, Case No. HC12C03487 Regarding EP (UK) 1 210 115.
*Hospira* v. *Genentech* trial in the High Court of Justice Chancery Division 2 Patents Court, Case No. HC12C03487 regarding EP (UK) 1 210 115, Approved Judgement , Date: Jul. 22, 2014 (9 pages).
*Hospira* v. *Genentech* trial in the Court of Appeal (Civil Division) on Appeal from the High Court of Justice Chancery Division, Case Bo: A3 2014 1800, regarding EP (UK) 1 210 115.
*Hospira* v. *Genentech* trial in the Court of Appeal (Civil Division) on Appeal from the High Court of Justice Chancery Division, Case Bo: A3 2014 1800, regarding EP (UK) 1 210 115Approved Judgment; Date: Feb. 6, 2015(14 Pages).
Opposition Proceedings regarding Hong Kong Patent No. 1048260.
Affidavit of Monique Chu, filed in Opposition Proceedings regarding Hong Kong Patent No. 1048260, HCA 1873/2013, dated Jun. 21, 2016 (8 pages).
Fourth Affidavit of Anthony Clinton Dudley Evans, filed in Opposition Proceedings regarding Hong Kong Patent No. 1048260, HCA 1873/2013, dated Jun. 21, 2016 (33 pages).

(56) References Cited

OTHER PUBLICATIONS

Decision of High Court Deputy Judge Kent Yee, issued in Opposition Proceedings regarding Hong Kong Patent No. 1048260, HCA 1873/2013, dated Jul. 13, 2016, (9 pages).
Order of Master Ho to discontinue proceedings, issued in Opposition Proceedings regarding Hong Kong Patent No. 1048260, HCA 1873/2013, dated Jul. 20, 2016 (2 pages).
Revocation Proceedings regarding South African Patent No. 2002/1229.
Notice of Withdrawal of Action, issued in Revocation Proceedings regarding South African Patent No. 2002/1229, dated Oct. 11, 2016 (2 pages).
Nullity Action No. 2016-900071 by Celltrion against Japanese Patent No. 5818545.
Demand for Invalidation of Japanese Patent No. 5818545 by Celltrion Incorporated, dated Jun. 17, 2016, in Japanese with English translation (130 pages).
"HER2-specific humanized monoclonal antibody trastuzumab [recombinant] Mitsubishi Chemical," New Current 1998, vol. 9, No. 24 in Japanese with English translation (3 pages).
Perez et al., "Two concurrent Phase II trials of Paclitaxel/Carboplatin/Trastuzumab (weekly or every-3-week schedule) as first-line therapy in women with HER2-overexpressing metastatic breast cancer: NCCTG Study 98252," Clinical Breast Cancer 2005, vol. 6, No. 5, pp. 425-432.
"Phase II Study of Paclitaxel, Carboplatin, and Trastuzumab (Herceptin) as First-Line Chemotherapy in Women With Overexpressed HER-2, Metastatic Breast Cancer" http://web.archive.org/web/20111023025823/http://cancer.gov/clinicaltrials/search/view?cdrid=66689&version=healthprofessional; first published: Dec. 1, 1998, retrieved Apr. 16, 2013.
K.Takada and S. Asada, "Chapter 4: Repetitive administration and dosage regimens," *Essential of Pharmacokinetics*, Hirokawa Publishing Company $2^{nd}$ printing (1979) of the first edition (1978), pp. 70-85.
Watanabe et al., "Phase I clinical trial results of anti-HER2 monoclonal antibody (MKC-454) to HER2/neu overexpressing metastic breast cancer ," $6^{th}$ Annual Meeting of the Japanese Breast Cancer Society Programs and Proceedings, May 22-23, 1998, Abstract 121, p. 59. in Japanese with English translation (3 pages).
Genentech's Reply Brief, dated Nov. 2, 2016, in Japanese with English translation (70 pages).
Celltrion's Summary of Oral Arguments, dated Feb. 7, 2017, in Japanese with English translation.
Genentech's Summary of oral arguments dated Jan. 24, 2017, in Japanese with English translation (87 pages).
Declaration of Dr. Robert I. Macey with Appendix A, dated Mar. 4, 2017 (11 pages), submitted by Genentech on Mar. 30, 2017.
Genentech's post-hearing statement, dated Mar. 7, 2017, in Japanese with English translation of parts (2) and (3).
Administrative Litigation Against Chinese Patent No. 200610008639. X.
Administrative Judgement by Supreme People's Court of the People's Republic of China dated Jun. 22, 2016 in Chinese with English translation (10 pages).
Petition for Inter Partes Review of U.S. Pat. No. 6,627,196, PTAB-IPR2017-00804 by Hospira Inc.
Petition for Inter Partes Review of U.S. Pat. No. 6,627,196 under 35 U.S.C. § 311 and 37 C.F.R. §42.100 by Hospira, Inc., dated Jan. 30, 2017 (71 pages).
Declaration of Dr. Allan Lipton filed in Inter Partes Review No. IPR2017-00804 re: U.S. Pat. No. 6,627,196, dated Jan. 30, 2017 (160 pages).
Declaration of Dr. William Jusko filed in Inter Partes Review No. IPR2017-00804 re: U.S. Pat. No. 6,627,196, dated Jan. 30, 2017 (104 pages).
Aaronson, et al., "The European Organization for Research and Treatment of Cancer QLQ-C30: A Quality-of-Life Instrument for Use in International Clinical Trials in Oncology," J. Nat'l. Cancer Institute 1993, vol. 85, No. 4, pp. 365-376.
Coates, et al., "Quality of Life in Oncology Practice: Prognostic Value of EORTC QLQ-C30 Scores in Patients with Advanced Malignancy," European Journal of Cancer 1997, vol. 33, No. 7, pp. 1025-1030.
Drugs@FDA: FDA Approved Drug Products for Herceptin, retrieved Dec. 22, 2016 from http://www.accessdata.fda.gov/scripts/cder/daf/index.cfm?event=overview.process&ApplNo=103792 (3 pages).
Ferrell, "Quality of Life in Breast Cancer," Cancer Practice 1996, vol. 4, No. 6, pp. 331-340.
Pegram, et al., "Phase II Study of Intravenous Recombinant Humanized Anti-p185 HER-2 Monoclonal Antibody (rhuMAb HER-2) Plus Cisplatin in Patients with HER-2/neu Overexpressing Metastatic Breast Cancer," Proceedings of the American Society of Clinical Oncology 1995, vol. 14, No. 106, abstract 124.
Press Release, Genentech, Inc. "Biotechnology Breakthrough in Breast Cancer Wins FDA Approval," posted Sep. 25, 1998 at https://www.gene.com/media/press-releases/4763/1998-09-25/biotechnology-breakthrough-in-breast-can, retrieved Dec. 30, 2016 (5 pages).
Vogel, et al., "Efficacy and Safety of Herceptin (Trastuzumab, Humanized Anti-HER2 Antibody) as a Single Agent in First-Line Treatment of HER2 Overexpressing Metastatic Breast Cancer (HER2+/MBC)," Breast Cancer Research and Treatment 1998, vol. 50, No. 1, abstract 23, p. 232.
Declaration of Dr. Sarah Baughman filed in Inter Partes Review No. IPR2016-00172 re: U.S. Pat. No. 8,889,135, dated Nov. 5, 2015 (47 pages ).
Walpole, et al., "The weight of nations: an estimation of adult human biomass," BMC Public Health 2012, vol. 12, No. 439, retrieved Dec. 27, 2016 from https://bmcpublichealth.biomedcentral.com/articles/10.1186/1471-2458-12-439.
U.S. Environmental Protection Agency, National Center for Environmental Assessment (NCEA) Office of Research and Development (ORD), "Exposure Factors Handbook" (1997). Retrieved Dec. 27, 2016, (1216 pages) htips://ofmpub.epa.gov/eims/eimscomm.getfile?p_download_id=503445.
Patent Owner's Preliminary Response, dated May 4, 2017 (60 pages).
Petition for Inter Partes Review of U.S Pat. No. 6,627,196, PTAB-IPR2017-01139 by Celltron, Inc.
Petition for Inter Partes Review of U.S. Pat. No. 6,627,196 under 35 U.S.C. § 311 and 37 C.F.R. §42.100 by Celltrion, Inc., dated Mar. 24, 2017 (64 pages).
Declaration of Mark J. Ratain, M.D., dated Mar. 22, 2017 (85 pages).
Coleman, Metastatic Bone Disease: Clinical Features, Pathophysiology and Treatment Strategies, Cancer Treat. Rev. 2001, vol. 27, 165-175.
Ferguson et al.. High Dose, Dose-Intensive Chemotherapy with Doxorubicin and Cyclophosphamide for the Treatment of Advanced Breast Cancer, 67 Br. J. Cancer, 825-829 (1993).
Greenberg et al., "Body Size and Survival in Premenopausal Breast Cancer," Br. J. Cancer 1985, vol. 51, pp. 691-697 (1985).
Mick et al., "Statistical approaches to pharmacodynamics modeling: motivations, methods and misperceptions," Cancer Chemother. Pharmacol. 1993, vol. 33, pp. 1-9.
Miller et al., "Principles of Pharmacology," The Chemotherapy Source Book, ed. Michael C. Perry, 2nd Edition., Williams & Wilkins, 1996, pp. 27-41.
Mordenti et al., "Interspecies Scaling of Clearance and Volume of Distribution Data for Five Therapeutic Proteins," Pharma. Res. 1991, vol. 8, pp. 1351-1359.
Newman et al., "A Study of the Effect of Weight and Dietary Fat on Breast Cancer Survival Time," Am. J. Epidemiol. 1986, vol. 123, pp. 767-774.
Ratain et al., "Statistical and Ethical Issues in the Design and Conduct of Phase I and II Clinical Trials of New Anticancer Agents," 85 J. Nat'l Cancer Inst. 1992, vol. 85, pp. 1637-1643.
Ratain et al., "Critical Role of Phase I Clinical Trials in Cancer Treatment," 15 J. Clin. Onc. 1997, vol. 15, pp. 853-859.
Ratain, "Pharmacokinetics and Pharmacodynamics, Pharmacology of Cancer Chemotherapy," Cancer, 5th Edition, Lippincott-Raven, 1997, pp. 375-385.

(56) References Cited

OTHER PUBLICATIONS

Richards et al., Doxorubicin in Advanced Breast Cancer: Influence of Schedule on Response, Survival and Quality of Life, 28A, 1992, Eur. J. Cancer 1023-1028.
Rothenberg et al., "Alternative Dosing Schedules for Irinotecan," Oncology 1998, vol. 12, pp. 68-71.
Tokuda et al., "Dose Escalation and Pharmacokinetic Study of a Humanized anti-HER2 Monoclonal Antibody in Patients with HER2/Neu-Overexpressing Metastatic Breast Cancer", 81 Br. J. Cancer, 1999, 1419-1425.
Slamon et al., "Addition of Herceptin (Humanized Anti-HER2 Antibody) to First Line Chemotherapy for HER2 Overexpressing Metastatic Breast Cancer(HER2+/MBC)Markedly Increases Anticancer Activity: A Randomized Multinational Controlled Phase III Trial," Proceedings of ASCO May 1998, vol. 17, No. 377, 98a.
Petition for Inter Partes Review of U.S. Pat. No. 7,371,379, PTAB-IPR2017-00805 by Hospira, Inc.
Petition for Inter Partes Review of U.S. Pat. No. 7,371,379, under 35 U.S.C. § 311 and 37 C.F.R. § 42.100 by Hospira, Inc., dated Jan. 30, 2017 (77 pages).
Declaration of Dr. Allan Lipton filed in Inter Partes Review No. IPR2017-00805 re: U.S. Pat. No. 7,371,379, dated Jan. 30, 2017 (169 pages).
Declaration of Dr. William Jusko filed in Inter Partes Review No. IPR2017-00805 re: U.S. Pat. No. 7,371,379, dated Jan. 30, 2017 (104 pages).
Patent Owner's Preliminary Response filed in Inter Partes Review No. IPR2017-00805 re: U.S. Pat. No. 7,371,379, dated May 4, 2017 (62 pages).
Petition for Inter Partes Review of U.S. Pat. No. 7,371,379, PTAB-IPR-01140 by Celltrion, Inc.
Petition for Inter Partes Review of U.S. Pat. No. 7,371,379, under 35 U.S.C. § 311 and 37 C.F.R. §42.100 by Celltrion, Inc., dated Mar. 24, 2017 (72 pages).
Declaration of Mark Ratain M.D., dated Mar. 22, 2017 (85 pages).
William J. Jusko, "Guidelines for Collection and Pharmacokinetic Analysis of Drug Disposition Data", in Applied Pharmacokinetics, ed. William Evans, Jerome Schentag, & William Jusko, 639-80, (1980).
Rowland and Tozer (1995), "Chapter 22: Dose and Time Dependencies," in *Clinical Pharmacokinetics*, $3^{rd}$ ed. Williams & Wilkins, pp. 394-423.
Sarfaraz Niazi, "Chapter 7: Pharmacokinetic Principles", in Textbook of Biopharmaceutics and Clinical Pharmacokinetics, 141-203 (1979).

\* cited by examiner

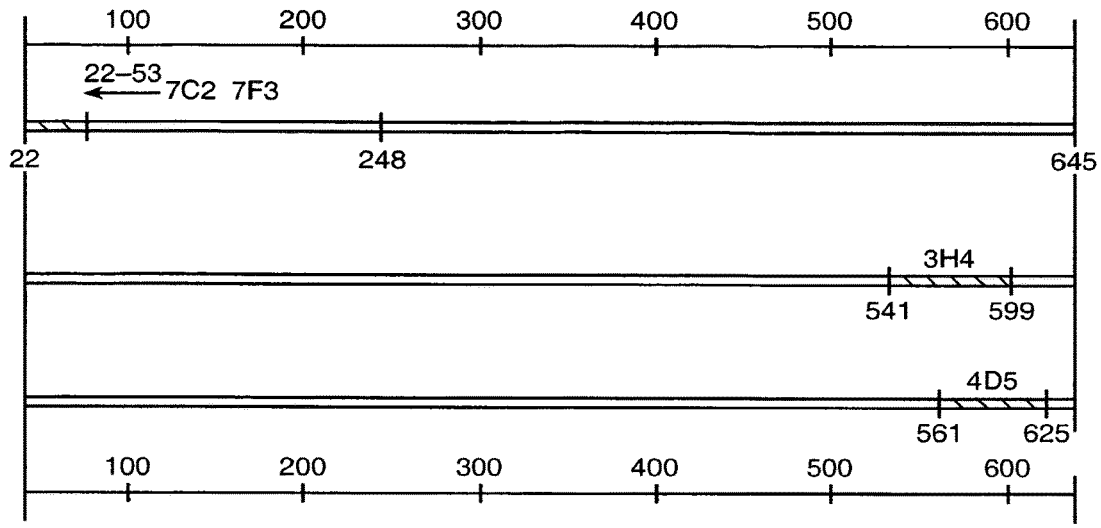

3H4 epitope (SEQ ID NO:8) 58 residues

VEECRVLQGLPREYVNARHCLPCHPECQPQNGSVTCFGPEADQCVACAHYKDPPFCVAR
|  |
541  599

4D5 epitope (SEQ ID NO:9) 64 residues

LPCHPECQPQNGSVTCFGPEADQCVACAHYKDPPFCVARCPSGVKPDLSYMPIWKFPDEEGACQP
|  |
561  625

*FIG._1*

```
  1   MELAALCRWGLLLALLPPGAASTQVCTGTDMKLRLPA
 38   SPETHLDMLRHLYQGCQVVQGNLELTYLPTNASLSFL
 75   QDIQEVQGYVLIAHNQVRQVPLQRLRIVRGTQLFEDN
112   YALAVLDNGDPLNNTPVTGASPGGLRELQLRSLTEI
149   LKGGVLIQRNPQLCYQDTILWKDIFHKNNQLALTLID
186   TNRSRA
```

*FIG._2*

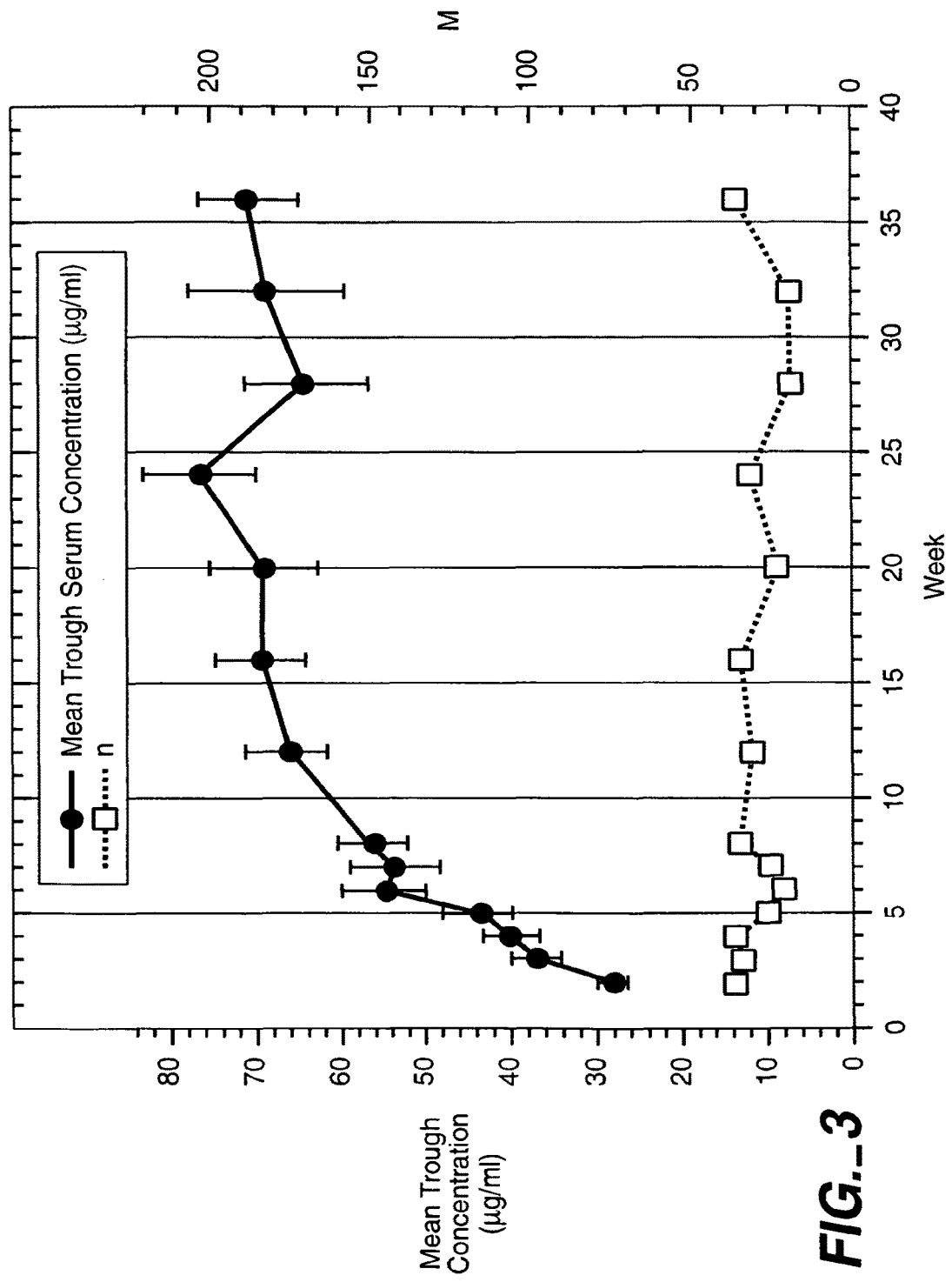
FIG._3

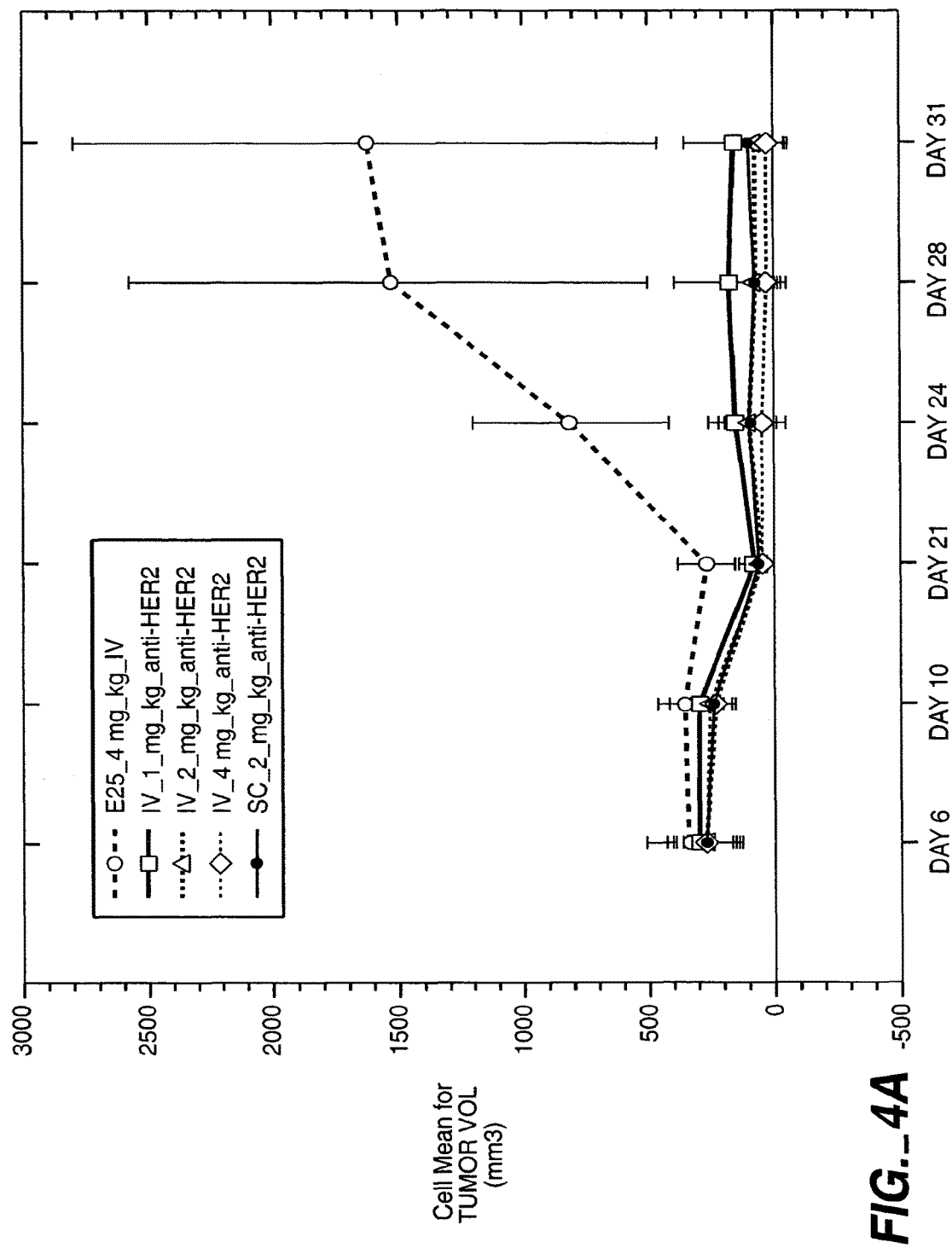
FIG._4A

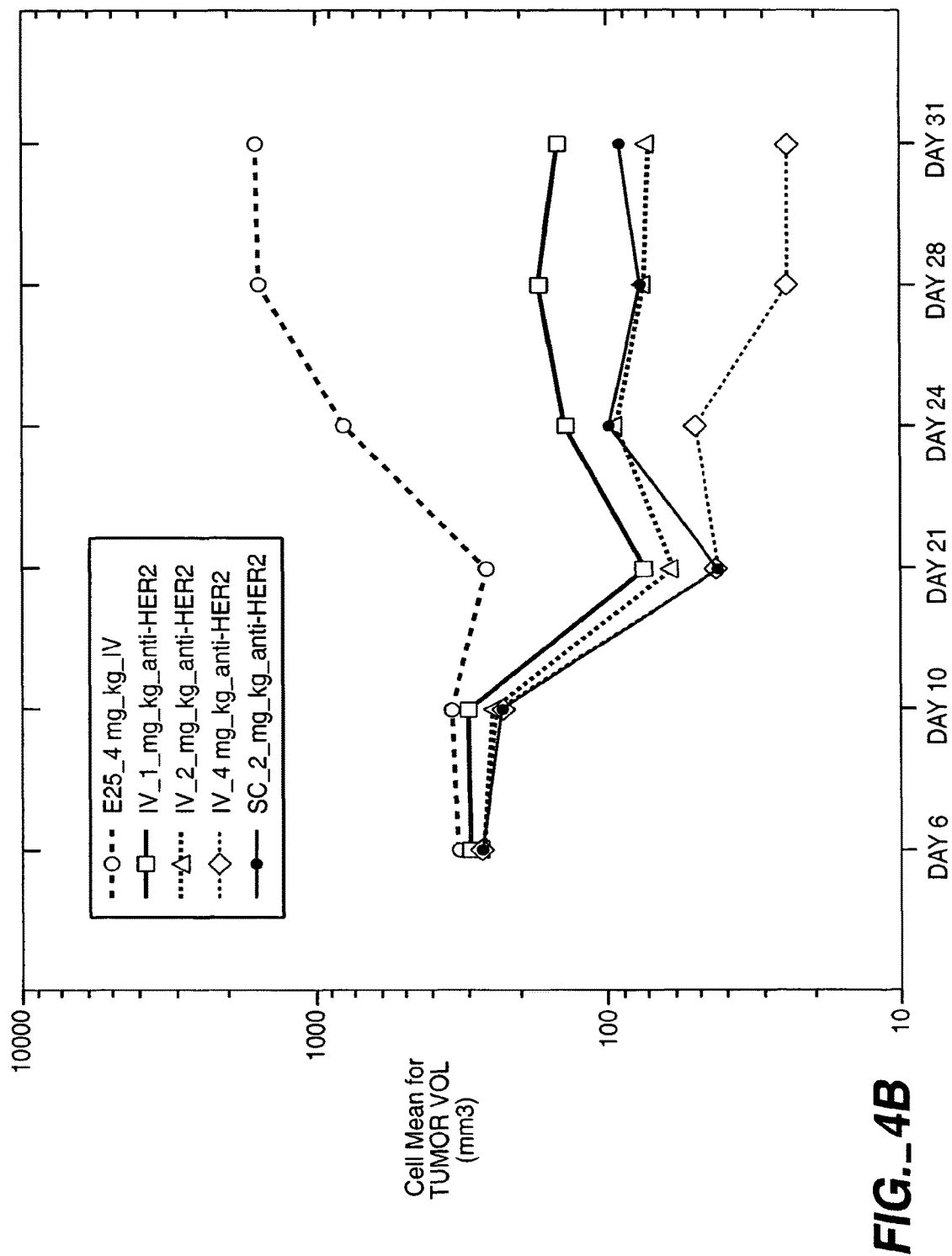
FIG._4B

VARIABLE LIGHT

```
              1         10         20          30            40
2C4      DTVMTQSHKIMSTSVGDRVSITC  [KASQDVSIGVA----]  WYQQRP
          **    **** *            *                       *
574      DIQMTQSPSSLSASVGDRVTITC  [KASQDVSIGVA----]  WYQQKP
                                    *   ****
hum kI   DIQMTQSPSSLSASVGDRVTITC  [RASQSVSTSSYSYMH]  WYQQKP 50         60         70         80
2C4      GQSPKLLIY  [SASYRYT]  GVPDRFTGSGSGTDFTFTISSVQA
          **                       *  *          *    * *
574      GKAPKLLIY  [SASYRYT]  GVPSRFSGSGSGTDFTLTISSLQP
                      *   ****
hum kI   GKAPKLLIY  [AASSLES]  GVPSRFSGSGSGTDFTLTISSLQP 90        100
2C4      EDLAVYYC  [QQYYIYPYT]  FGGGTKLEIK   (SEQ ID NO:10)
          * *                      *  *
574      EDFATYYC  [QQYYIYPYT]  FGQGTKVEIK   (SEQ ID NO:12)
                     ***
hum kI   EDFATYYC  [QQYNSLPYT]  FGQGTKVEIK   (SEQ ID NO:14)
```

*FIG._5A*

VARIABLE HEAVY

```
              1         10         20          30            40
2C4      EVQLQQSGPELVKPGTSVKISCKAS  [GFTFTDYTMD]  WVKQS
           **  **  *  * ***  **                      *
574      EVQLVESGGGLVQPGGSLRLSCAAS  [GFTFTDYTMD]  WVRQA
                                       ** *  *
humIII   EVQLVESGGGSVQPGGSLRLSCAAS  [GFTFSSYAMS]  WVRQA 50         60          70          80
2C4      HGKSLEWIG  [DVNPNSGGSIYNQRFKG]  KASLTVDRSSRIVYM
          *   *  **                       *** *    **** *
574      PGKGLEWVA  [DVNPNSGGSIYNQRFKG]  RFTLSVDRSKNTLYL
             *    ******  **  ****         *  *
humIII   PGKGLEWVS  [VISGDGGSTYYADSVKG]  RFTISRDDSKNTLYL 90        100        110
2C4      ELRSLTFEDTAVYYCAR  [NLGPSFYFDY]  WGQGTTLVTSS  (SEQ ID NO:11)
         *** **                              *
574      QMNSLRAEDTAVYYCAR  [NLGPSFYFDY]  WGQGTLVTVSS  (SEQ ID NO:13)
                                ** ***
humIII   QMNSLRAEDTAVYYCAR  [GRGGGS--DY]  WGQGTLVTVSS  (SEQ ID NO:15)
```

*FIG._5B*

SEQUENCE LISTING

```
<160> NUMBER OF SEQ ID NOS: 15

<210> SEQ ID NO 1
<211> LENGTH: 166
<212> TYPE: PRT
<213> ORGANISM: Homo sapiens

<400> SEQUENCE: 1

Cys Thr Gly Thr Asp Met Lys Leu Arg Leu Pro Ala Ser Pro Glu Thr
1               5                   10                  15

His Leu Asp Met Leu Arg His Leu Tyr Gln Gly Cys Gln Val Val Gln
            20                  25                  30
```

```
Gly Asn Leu Glu Leu Thr Tyr Leu Pro Thr Asn Ala Ser Leu Ser Phe
            35                  40                  45

Leu Gln Asp Ile Gln Glu Val Gln Gly Tyr Val Leu Ile Ala His Asn
 50                  55                  60

Gln Val Arg Gln Val Pro Leu Gln Arg Leu Arg Ile Val Arg Gly Thr
 65                  70                  75                  80

Gln Leu Phe Glu Asp Asn Tyr Ala Leu Ala Val Leu Asp Asn Gly Asp
                 85                  90                  95

Pro Leu Asn Asn Thr Thr Pro Val Thr Gly Ala Ser Pro Gly Gly Leu
                100                 105                 110

Arg Glu Leu Gln Leu Arg Ser Leu Thr Glu Ile Leu Lys Gly Gly Val
                115                 120                 125

Leu Ile Gln Arg Asn Pro Gln Leu Cys Tyr Gln Asp Thr Ile Leu Trp
    130                 135                 140

Lys Asp Ile Phe His Lys Asn Asn Gln Leu Ala Leu Thr Leu Ile Asp
145                 150                 155                 160

Thr Asn Arg Ser Arg Ala
                165
```

```
<210> SEQ ID NO 2
<211> LENGTH: 32
<212> TYPE: PRT
<213> ORGANISM: Homo sapiens

<400> SEQUENCE: 2

Ser Thr Gln Val Cys Thr Gly Thr Asp Met Lys Leu Arg Leu Pro Ala
1               5                   10                  15

Ser Pro Glu Thr His Leu Asp Met Leu Arg His Leu Tyr Gln Gly Cys
                20                  25                  30

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      salvage receptor binding epitope

<400> SEQUENCE: 3

Pro Lys Asn Ser Ser Met Ile Ser Asn Thr Pro
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      salvage receptor binding epitope

<400> SEQUENCE: 4

His Gln Ser Leu Gly Thr Gln
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      salvage receptor binding epitope
```

```
<400> SEQUENCE: 5

His Gln Asn Leu Ser Asp Gly Lys
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      salvage receptor binding epitope

<400> SEQUENCE: 6

His Gln Asn Ile Ser Asp Gly Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      salvage receptor binding epitope

<400> SEQUENCE: 7

Val Ile Ser Ser His Leu Gly Gln
1               5

<210> SEQ ID NO 8
<211> LENGTH: 59
<212> TYPE: PRT
<213> ORGANISM: Homo sapiens

<400> SEQUENCE: 8

Val Glu Glu Cys Arg Val Leu Gln Gly Leu Pro Arg Glu Tyr Val Asn
1               5                   10                  15

Ala Arg His Cys Leu Pro Cys His Pro Glu Cys Gln Pro Gln Asn Gly
            20                  25                  30

Ser Val Thr Cys Phe Gly Pro Glu Ala Asp Gln Cys Val Ala Cys Ala
        35                  40                  45

His Tyr Lys Asp Pro Pro Phe Cys Val Ala Arg
    50                  55

<210> SEQ ID NO 9
<211> LENGTH: 65
<212> TYPE: PRT
<213> ORGANISM: Homo sapiens

<400> SEQUENCE: 9

Leu Pro Cys His Pro Glu Cys Gln Pro Gln Asn Gly Ser Val Thr Cys
1               5                   10                  15

Phe Gly Pro Glu Ala Asp Gln Cys Val Ala Cys Ala His Tyr Lys Asp
            20                  25                  30

Pro Pro Phe Cys Val Ala Arg Cys Pro Ser Gly Val Lys Pro Asp Leu
        35                  40                  45

Ser Tyr Met Pro Ile Trp Lys Phe Pro Asp Glu Glu Gly Ala Cys Gln
    50                  55                  60

Pro
65
```

```
<210> SEQ ID NO 10
<211> LENGTH: 107
<212> TYPE: PRT
<213> ORGANISM: Mus musculus

<400> SEQUENCE: 10

Asp Thr Val Met Thr Gln Ser His Lys Ile Met Ser Thr Ser Val Gly
 1               5                  10                  15

Asp Arg Val Ser Ile Thr Cys Lys Ala Ser Gln Asp Val Ser Ile Gly
            20                  25                  30

Val Ala Trp Tyr Gln Gln Arg Pro Gly Gln Ser Pro Lys Leu Leu Ile
        35                  40                  45

Tyr Ser Ala Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Tyr Tyr Ile Tyr Pro Tyr
                85                  90                  95

Thr Phe Gly Gly Gly Thr Lys Leu Glu Ile Lys
            100                 105

<210> SEQ ID NO 11
<211> LENGTH: 119
<212> TYPE: PRT
<213> ORGANISM: Mus musculus

<400> SEQUENCE: 11

Glu Val Gln Leu Gln Gln Ser Gly Pro Glu Leu Val Lys Pro Gly Thr
 1               5                  10                  15

Ser Val Lys Ile Ser Cys Lys Ala Ser Gly Phe Thr Phe Thr Asp Tyr
            20                  25                  30

Thr Met Asp Trp Val Lys Gln Ser His Gly Lys Ser Leu Glu Trp Ile
        35                  40                  45

Gly Asp Val Asn Pro Asn Ser Gly Gly Ser Ile Tyr Asn Gln Arg Phe
50                  55                  60

Lys Gly Lys Ala Ser Leu Thr Val Asp Arg Ser Ser Arg Ile Val Tyr
65                  70                  75                  80

Met Glu Leu Arg Ser Leu Thr Phe Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      humanized VL polypeptide sequence

<400> SEQUENCE: 12

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45
```

```
Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      humanized VH polypeptide sequence

<400> SEQUENCE: 13

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      VL consensus sequence

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys
            100                 105
```

```
<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic
      VH consensus sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Val Gly Tyr Ser Leu Tyr Asp Tyr Trp Gly Gln Gly
            100                 105                 110

Thr Leu Val Thr Val Ser Ser
            115
```

TREATMENT WITH ANTI-ERBB2 ANTIBODIES

RELATED APPLICATIONS

This application is divisional of U.S. Ser. No. 10/600,152 filed Jun. 20, 2003, which is a divisional of U.S. Ser. No. 09/648,067 filed Aug. 25, 2000 (now U.S. Pat. No. 6,627,196), which claims priority under 35 USC 119(e) to provisional application Nos. 60/151,018, filed Aug. 27, 1999 and 60/213,822, filed Jun. 23, 2000, the contents of which are incorporated herein by reference.

FIELD OF THE INVENTION

The present invention concerns the treatment of disorders characterized by the overexpression of ErbB2 or disorders expressing epidermal growth factor receptor (EGFR), comprising administering to a human or animal presenting the disorders a therapeutically effective amount of an antibody that binds ErbB2. More specifically, the invention concerns the treatment of human patients susceptible to or diagnosed with cancer overexpressing ErbB2 or expressing EGFR, where the treatment is with an anti-ErbB2 antibody administered by front loading the dose of antibody during treatment by intravenous and/or subcutaneous administration. The invention optionally includes treatment of cancer in a human patient with a combination of an anti-ErbB2 antibody and a chemotherapeutic agent, such as, but not limited to, a taxoid. The taxoid may be, but is not limited to paclitaxel or docetaxel. The invention further includes treatment of cancer in a human patient with a combination of anti-ErbB2 antibody and a chemotherapeutic agent, such as, but not limited to, an anthracycline derivative. Optionally, treatment with a combination of anti-ErbB2 and an anthracycline derivative includes treatment with an effective amount of a cardioprotectant. The present invention further concerns infrequent dosing of anti-ErbB2 antibodies.

BACKGROUND OF THE INVENTION

Proto-oncogenes that encode growth factors and growth factor receptors have been identified to play important roles in the pathogenesis of various human malignancies, including breast cancer. It has been found that the human ErbB2 gene (erbB2, also known as her2, or c-erbB-2), which encodes a 185-kd transmembrane glycoprotein receptor ($p185^{HER2}$) related to the epidermal growth factor receptor (EGFR), is overexpressed in about 25% to 30% of human breast cancer (Slamon et al., Science 235:177-182 [1987]; Slamon et al., Science 244:707-712 [1989]).

Several lines of evidence support a direct role for ErbB2 in the pathogenesis and clinical aggressiveness of ErbB2-overexpressing tumors. The introduction of ErbB2 into non-neoplastic cells has been shown to cause their malignant transformation (Hudziak et al., Proc. Natl. Acad. Sci. USA 84:7159-7163 [1987]; DiFiore et al., Science 237:78-182 [1987]). Transgenic mice that express HER2 were found to develop mammary tumors (Guy et al., Proc. Natl. Acad. Sci. USA 89:10578-10582 [1992]).

Antibodies directed against human erbB2 protein products and proteins encoded by the rat equivalent of the erbB2 gene (neu) have been described. Drebin et al., Cell 41:695-706 (1985) refer to an IgG2a monoclonal antibody which is directed against the rat neu gene product. This antibody called 7.16.4 causes down-modulation of cell surface p185 expression on B104-1-1 cells (NIH-3T3 cells transfected with the neu proto-oncogene) and inhibits colony formation of these cells. In Drebin et al. PNAS (USA) 83:9129-9133 (1986), the 7.16.4 antibody was shown to inhibit the tumorigenic growth of neu-transformed NIH-3T3 cells as well as rat neuroblastoma cells (from which the neu oncogene was initially isolated) implanted into nude mice. Drebin et al. in Oncogene 2:387-394 (1988) discuss the production of a panel of antibodies against the rat neu gene product. All of the antibodies were found to exert a cytostatic effect on the growth of neu-transformed cells suspended in soft agar. Antibodies of the IgM, IgG2a and IgG2b isotypes were able to mediate significant in vitro lysis of neu-transformed cells in the presence of complement, whereas none of the antibodies were able to mediate high levels of antibody-dependent cellular cytotoxicity (ADCC) of the neu-transformed cells. Drebin et al. Oncogene 2:273-277 (1988) report that mixtures of antibodies reactive with two distinct regions on the p185 molecule result in synergistic anti-tumor effects on neu-transformed NIH-3T3 cells implanted into nude mice. Biological effects of anti-neu antibodies are reviewed in Myers et al., Meth. Enzym. 198:277-290 (1991). See also WO94/22478 published Oct. 13, 1994. Hudziak et al., Mol. Cell. Biol. 9(3): 1165-1172 (1989) describe the generation of a panel of anti-ErbB2 antibodies which were characterized using the human breast tumor cell line SKBR3. Relative cell proliferation of the SKBR3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel, including 7C2 and 7F3, reduced cellular proliferation to a lesser extent in this assay. Hudziak et al. conclude that the effect of the 4D5 antibody on SKBR3 cells was cytostatic rather than cytotoxic, since SKBR3 cells resumed growth at a nearly normal rate following removal of the antibody from the medium. The antibody 4D5 was further found to sensitize $p185^{erbB2}$-overexpressing breast tumor cell lines to the cytotoxic effects of TNF-α. See also WO89/06692 published Jul. 27, 1989. The anti-ErbB2 antibodies discussed in Hudziak et al. are further characterized in Fendly et al. Cancer Research 50:1550-1558 (1990); Kotts et al. In Vitro 26(3):59A (1990); Sarup et al. Growth Regulation 1:72-82 (1991); Shepard et al. J. Clin. Immunol. 11(3):117-127 (1991); Kumar et al. Mol. Cell. Biol. 11(2): 979-986 (1991); Lewis et al. Cancer Immunol. Immunother. 37:255-263 (1993); Pietras et al. Oncogene 9:1829-1838 (1994); Vitetta et al. Cancer Research 54:5301-5309 (1994); Sliwkowski et al. J. Biol. Chem. 269(20):14661-14665 (1994); Scott et al. J. Biol. Chem. 266:14300-5 (1991); and D'souza et al. Proc. Natl. Acad. Sci. 91:7202-7206 (1994).

Tagliabue et al. Int. J. Cancer 47:933-937 (1991) describe two antibodies which were selected for their reactivity on the lung adenocarcinoma cell line (Calu-3) which overexpresses ErbB2. One of the antibodies, called MGR3, was found to internalize, induce phosphorylation of ErbB2, and inhibit tumor cell growth in vitro.

McKenzie et al. Oncogene 4:543-548 (1989) generated a panel of anti-ErbB2 antibodies with varying epitope specificities, including the antibody designated TA1. This TA1 antibody was found to induce accelerated endocytosis of ErbB2 (see Maier et al. Cancer Res. 51:5361-5369 [1991]). Bacus et al. Molecular Carcinogenesis 3:350-362 (1990) reported that the TA1 antibody induced maturation of the breast cancer cell lines AU-565 (which overexpresses the erbB2 gene) and MCF-7 (which does not). Inhibition of growth and acquisition of a mature phenotype in these cells was found to be associated with reduced levels of ErbB2 receptor at the cell surface and transient increased levels in the cytoplasm.

Stancovski et al. *PNAS (USA)* 88:8691-8695 (1991) generated a panel of anti-ErbB2 antibodies, injected them i.p. into nude mice and evaluated their effect on tumor growth of murine fibroblasts transformed by overexpression of the erbB2 gene. Various levels of tumor inhibition were detected for four of the antibodies, but one of the antibodies (N28) consistently stimulated tumor growth. Monoclonal antibody N28 induced significant phosphorylation of the ErbB2 receptor, whereas the other four antibodies generally displayed low or no phosphorylation-inducing activity. The effect of the anti-ErbB2 antibodies on proliferation of SKBR3 cells was also assessed. In this SKBR3 cell proliferation assay, two of the antibodies (N12 and N29) caused a reduction in cell proliferation relative to control. The ability of the various antibodies to induce cell lysis in vitro via complement-dependent cytotoxicity (CDC) and antibody-mediated cell-dependent cytotoxicity (ADCC) was assessed, with the authors of this paper concluding that the inhibitory function of the antibodies was not attributed significantly to CDC or ADCC.

Bacus et al. *Cancer Research* 52:2580-2589 (1992) further characterized the antibodies described in Bacus et al. (1990) and Stancovski et al. of the preceding paragraphs. Extending the i.p. studies of Stancovski et al., the effect of the antibodies after i.v. injection into nude mice harboring mouse fibroblasts overexpressing human ErbB2 was assessed. As observed in their earlier work, N28 accelerated tumor growth, whereas N12 and N29 significantly inhibited growth of the ErbB2-expressing cells. Partial tumor inhibition was also observed with the N24 antibody. Bacus et al. also tested the ability of the antibodies to promote a mature phenotype in the human breast cancer cell lines AU-565 and MDA-MB453 (which overexpress ErbB2) as well as MCF-7 (containing low levels of the receptor). Bacus et al. saw a correlation between tumor inhibition in vivo and cellular differentiation; the tumor-stimulatory antibody N28 had no effect on differentiation, and the tumor inhibitory action of the N12, N29 and N24 antibodies correlated with the extent of differentiation they induced.

Xu et al. *Int. J. Cancer* 53:401-408 (1993) evaluated a panel of anti-ErbB2 antibodies for their epitope binding specificities, as well as their ability to inhibit anchorage-independent and anchorage-dependent growth of SKBR3 cells (by individual antibodies and in combinations), modulate cell-surface ErbB2, and inhibit ligand stimulated anchorage-independent growth. See also WO94/00136 published Jan. 6, 1994 and Kasprzyk et al. *Cancer Research* 52:2771-2776 (1992) concerning anti-ErbB2 antibody combinations. Other anti-ErbB2 antibodies are discussed in Hancock et al. *Cancer Res.* 51:4575-4580 (1991); Shawver et al. *Cancer Res.* 54:1367-1373 (1994); Arteaga et al. *Cancer Res.* 54:3758-3765 (1994); and Harwerth et al. *J. Biol. Chem.* 267:15160-15167 (1992).

A recombinant humanized anti-ErbB2 monoclonal antibody (a humanized version of the murine anti-ErbB2 antibody 4D5, referred to as rhuMAb HER2, HERCEPTIN®, or HERCEPTIN® anti-ErbB2 antibody) has been clinically active in patients with ErbB2-overexpressing metastatic breast cancers that had received extensive prior anti-cancer therapy (Baselga et al., *J. Clin. Oncol.* 14:737-744 [1996]). The recommended initial loading dose for HERCEPTIN® is 4 mg/kg administered as a 90-minute infusion. The recommended weekly maintenance dose is 2 mg/kg and can be administered as a 30-minute infusion if the initial loading dose is well tolerated.

ErbB2 overexpression is commonly regarded as a predictor of a poor prognosis, especially in patients with primary disease that involves axillary lymph nodes (Slamon et al., [1987] and [1989], supra; Ravdin and Chamness, *Gene* 159:19-27 [1995]; and Hynes and Stern, *Biochim Biophys Acta* 1198:165-184 [1994]), and has been linked to sensitivity and/or resistance to hormone therapy and chemotherapeutic regimens, including CMF (cyclophosphamide, methotrexate, and fluoruracil) and anthracyclines (Baselga et al., *Oncology* 11(3 Suppl 1):43-48 [1997]). However, despite the association of ErbB2 overexpression with poor prognosis, the odds of HER2-positive patients responding clinically to treatment with taxanes were greater than three times those of HER2-negative patients (Ibid). rhuMab HER2 was shown to enhance the activity of paclitaxel (TAXOL®) and doxorubicin against breast cancer xenografts in nude mice injected with BT-474 human breast adenocarcinoma cells, which express high levels of HER2 (Baselga et al., *Breast Cancer, Proceedings of ASCO*, Vol. 13, Abstract 53 [1994]).

SUMMARY OF THE INVENTION

The present invention concerns the discovery that an early attainment of an efficacious target trough serum concentration by providing an initial dose or doses of anti-ErbB2 antibodies followed by subsequent doses of equal or smaller amounts of antibody (greater front loading) is more efficacious than conventional treatments. The efficacious target trough serum concentration is reached in 4 weeks or less, preferably 3 weeks or less, more preferably 2 weeks or less, and most preferably 1 week or less, including 1 day or less. The target serum concentration is thereafter maintained by the administration of maintenance doses of equal or smaller amounts for the remainder of the treatment regimen or until suppression of disease symptoms is achieved.

The invention further concerns a method for the treatment of a human patient susceptible to or diagnosed with a disorder characterized by overexpression of ErbB2 receptor comprising administering a therapeutically effective amount of an anti-ErbB2 antibody subcutaneously. Preferably, the initial dose (or doses) as well as the subsequent maintenance dose or doses are administered subcutaneously. Optionally, where the patient's tolerance to the anti-ErbB2 antibody is unknown, the initial dose is administered by intravenous infusion, followed by subcutaneous administration of the maintenance doses if the patient's tolerance for the antibody is acceptable.

According to the invention, the method of treatment involves administration of an initial dose of anti-ErbB2 antibody of more than approximately 4 mg/kg, preferably more than approximately 5 mg/kg. The maximum initial dose or a subsequent dose does not exceed 50 mg/kg, preferably does not exceed 40 mg/kg, and more preferably does not exceed 30 mg/kg. Administration is by intravenous or subcutaneous administration, preferably intravenous infusion or bolus injection, or more preferably subcutaneous bolus injection. The initial dose may be one or more administrations of drug sufficient to reach the target trough serum concentration in 4 weeks or less, preferably 3 weeks or less, more preferably 2 weeks or less, and most preferably 1 week or less, including one day or less.

According to the invention, the initial dose or doses is/are followed by subsequent doses of equal or smaller amounts of antibody at intervals sufficiently close to maintain the trough serum concentration of antibody at or above an efficacious target level. Preferably, an initial dose or subsequent dose does not exceed 50 mg/kg, and each subsequent dose is at least 0.01 mg/kg. Preferably the amount of drug administered is sufficient to maintain the target trough serum concentration such that the interval between administration cycles is at least one week. Preferably the trough serum concentration does not exceed 2500 µg/ml and does not fall below 0.01 µg/ml during treatment. The front loading drug treatment method of the invention has the advantage of increased efficacy by reaching a target serum drug concentration early in treatment. The subcutaneous delivery of maintenance doses according to the invention has the advantage of being convenient for the patient and health care professionals, reducing time and costs for drug treatment. Preferably, the initial dose (or the last dose within an initial dose series) is separated in time from the first subsequent dose by 4 weeks or less, preferably 3 weeks or less, more preferably 3 weeks or less, most preferably 1 week or less.

In an embodiment of the invention, the initial dose of anti-ErbB2 is 6 mg/kg, 8 mg/kg, or 12 mg/kg delivered by intravenous or subcutaneous administration, such as intravenous infusion or subcutaneous bolus injection. The subsequent maintenance doses are 2 mg/kg delivered once per week by intravenous infusion, intravenous bolus injection, subcutaneous infusion, or subcutaneous bolus injection. The choice of delivery method for the initial and maintenance doses is made according to the ability of the animal or human patient to tolerate introduction of the antibody into the body. Where the antibody is well-tolerated, the time of infusion may be reduced. The choice of delivery method as disclosed for this embodiment applies to all drug delivery regimens contemplated according to the invention.

In another embodiment, the invention includes an initial dose of 12 mg/kg anti-ErbB2 antibody, followed by subsequent maintenance doses of 6 mg/kg once per 3 weeks.

In still another embodiment, the invention includes an initial dose of 8 mg/kg anti-ErbB2 antibody, followed by 6 mg/kg once per 3 weeks.

In yet another embodiment, the invention includes an initial dose of 8 mg/kg anti-ErbB2 antibody, followed by subsequent maintenance doses of 8 mg/kg once per week or 8 mg/kg once every 2 to 3 weeks.

In another embodiment, the invention includes initial doses of at least 1 mg/kg, preferably 4 mg/kg, anti-ErbB2 antibody on each of days 1, 2 and 3, followed by subsequent maintenance doses of 6 mg/kg once per 3 weeks.

In another embodiment, the invention includes an initial dose of 4 mg/kg anti-ErbB2 antibody, followed by subsequent maintenance doses of 2 mg/kg twice per week, wherein the maintenance doses are separated by 3 days.

In still another embodiment, the invention includes a cycle of dosing in which delivery of anti-ErbB2 antibody is 2-3 times per week for 3 weeks. In one embodiment of the invention, each dose is approximately 25 mg/kg or less for a human patient, preferably approximately 10 mg/kg or less. This 3 week cycle is preferably repeated as necessary to achieve suppression of disease symptoms.

In another embodiment, the invention includes a cycle of dosing in which delivery of anti-ErbB2 antibody is daily for 5 days. According to the invention, the cycle is preferably repeated as necessary to achieve suppression of disease symptoms.

The disorder preferably is a benign or malignant tumor characterized by the overexpression of the ErbB2 receptor, e.g. a cancer, such as, breast cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer. The method of the invention may further comprise administration of a chemotherapeutic agent other than an anthracycline, e.g. doxorubicin or epirubicin. The chemotherapeutic agent preferably is a taxoid, such as TAXOL® (paclitaxel) or a TAXOL® derivative.

Preferred anti-ErbB2 antibodies bind the extracellular domain of the ErbB2 receptor, and preferably bind to the epitope 4D5 or 3H4 within the ErbB2 extracellular domain sequence. More preferably, the antibody is the antibody 4D5, most preferably in a humanized form. Other preferred ErbB2-binding antibodies include, but are not limited to, antibodies 7C2, 7F3, and 2C4, preferably in a humanized form.

The method of the present invention is particularly suitable for the treatment of breast or ovarian cancer, characterized by the overexpression of the ErbB2 receptor.

The present application also provides a method of therapy involving infrequent dosing of an anti-ErbB2 antibody. In particular, the invention provides a method for the treatment of cancer (e.g. cancer characterized by overexpression of the ErbB2 receptor) in a human patient comprising administering to the patient a first dose of an anti-ErbB2 antibody followed by at least one subsequent dose of the antibody, wherein the first dose and subsequent dose are separated from each other in time by at least about two weeks (e.g. from about two weeks to about two months), and optionally at least about three weeks (e.g. from about three weeks to about six weeks). For instance, the antibody may be administered about every three weeks, about two to about 20 times, e.g. about six times. The first dose and subsequent dose may each be from about 2 mg/kg to about 16 mg/kg; e.g. from about 4 mg/kg to about 12 mg/kg; and optionally from about 6 mg/kg to about 12 mg/kg. Generally, two or more subsequent doses (e.g. from about two to about ten subsequent doses) of the antibody are administered to the patient, and those subsequent doses are preferably separated from each other in time by at least about two weeks (e.g. from about two weeks to about two months), and optionally at least about three weeks (e.g. from about three weeks to about six weeks). The two or more subsequent doses may each be from about 2 mg/kg to about 16 mg/kg; or from about 4 mg/kg to about 12 mg/kg; or from about 6 mg/kg to about 12 mg/kg. The invention additionally provides an article of manufacture, comprising a container, a composition within the container comprising an anti-ErbB2 antibody, and a package insert containing instructions to administer the antibody according to such methods.

The presently described dosing protocols may be applied to other anti-ErbB antibodies such as anti-epidermal growth factor receptor (EGFR), anti-ErbB3 and anti-ErbB4 antibodies. Thus, the invention provides a method for the treatment of cancer in a human patient, comprising administering an effective amount of an anti-ErbB antibody to the human patient, the method comprising administering to the patient an initial dose of at least approximately 5 mg/kg of the anti-ErbB antibody; and administering to the patient a plurality of subsequent doses of the antibody in an amount that is approximately the same or less than the initial dose. Alternatively, or additionally, the invention pertains to a method for the treatment of cancer in a human patient comprising administering to the patient a first dose of an anti-ErbB antibody followed by at least one subsequent dose of the antibody, wherein the first dose and subsequent dose are separated from each other in time by at least about two weeks. The invention additionally provides an article of manufacture, comprising a container, a composition within the container comprising an anti-ErbB antibody, and a package insert containing instructions to administer the antibody according to such methods.

In another aspect, the invention concerns an article of manufacture, comprising a container, a composition within the container comprising an anti-ErbB2 antibody, optionally a label on or associated with the container that indicates that the composition can be used for treating a condition characterized by overexpression of ErbB2 receptor, and a package insert containing instructions to avoid the use of anthracycline-type chemotherapeutics in combination with the composition. According to the invention, the package insert further includes instructions to administer the anti-ErbB2 antibody at an initial dose of 5 mg/kg followed by the same or smaller subsequent dose or doses. In another embodiment of the invention, the package insert further includes instructions to administer the anti-ErbB2 antibody subcutaneously for at least one of the doses, preferably for all of the subsequent doses following the initial dose, most preferably for all doses.

In a further aspect, the invention provides a method of treating ErbB2 expressing cancer in a human patient comprising administering to the patient effective amounts of an anti-ErbB2 antibody and a chemotherapeutic agent. In one embodiment of the invention, the chemotherapeutic agent is a taxoid including, but not limited to, paclitaxel and docetaxel. In another embodiment, the chemotherapeutic agent is an anthracyline derivative including, but not limited to, doxorubicin or epirubicin. In still another embodiment of the invention, treatment with an anti-ErbB2 antibody and an anthracycline derivative further includes administration of a cardioprotectant to the patient. In still another embodiment, an anthracycline derivative is not administered to the patient with the anti-ErbB2 antibody. One or more additional chemotherapeutic agents may also be administered to the patient. The cancer is preferably characterized by overexpression of ErbB2.

The invention further provides an article of manufacture comprising a container, a composition within the container comprising an anti-ErbB2 antibody and a package insert instructing the user of the composition to administer the anti-ErbB2 antibody composition and a chemotherapeutic agent to a patient. In another embodiment, the chemotherapeutic agent is other than an anthracycline, and is preferably a taxoid, such as TAXOL®. In still another embodiment, the chemotherapeutic agent is an anthracycline, including but not limited to, doxorubicin or epirubicin. In yet another embodiment, the chemotherapeutic agent is an anthracycline and the package insert further instructs the user to administer a cardioprotectant.

The methods and compositions of the invention comprise an anti-ErbB2 antibody and include a humanized anti-ErbB2 antibody. Thus, the invention further pertains to a composition comprising an antibody that binds ErbB2 and the use of the antibody for treating ErbB2 expressing cancer, e.g., ErbB2 overexpressing cancer, in a human. The invention also pertains to the use of the antibody for treating EGFR expressing cancer. Preferably the antibody is a monoclonal antibody 4D5, e.g., humanized 4D5 (and preferably huMAb4D5-8 (HERCEPTIN® anti-ErbB2 antibody); or monoclonal antibody 2C4, e.g., humanized 2C4. The antibody may be an intact antibody (e.g., an intact IgG$_1$ antibody) or an antibody fragment (e.g., a Fab, F(ab')$_2$, diabody, and the like). The variable light chain and variable heavy chain regions of humanized anti-ErbB2 antibody 2C4 are shown in FIGS. 5A and 5B.

BRIEF DESCRIPTION OF THE DRAWINGS

FIG. 1 shows epitope-mapping of the extracellular domain of ErbB2 as determined by truncation mutant analysis and site-directed mutagenesis (Nakamura et al. *J. of Virology* 67(10):6179-6191 [October 1993]; Renz et al. *J. Cell Biol.* 125(6):1395-1406 [June 1994]). The anti-proliferative MAbs 4D5 and 3H4 bind adjacent to the transmembrane domain. The various ErbB2-ECD truncations or point mutations were prepared from cDNA using polymerase chain reaction technology. The ErbB2 mutants were expressed as gD fusion proteins in a mammalian expression plasmid. This expression plasmid uses the cytomegalovirus promoter/enhancer with SV40 termination and polyadenylation signals located downstream of the inserted cDNA. Plasmid DNA was transfected into 293S cells. One day following transfection, the cells were metabolically labeled overnight in methionine and cysteine-free, low glucose DMEM containing 1% dialyzed fetal bovine serum and 25 µCi each of $^{35}$S methionine and $^{35}$S cysteine. Supernatants were harvested either the ErbB2 MAbs or control antibodies were added to the supernatant and incubated 2-4 hours at 4° C. The complexes were precipitated, applied to a 10-20% Tricine SDS gradient gel and electrophoresed at 100 V. The gel was electroblotted onto a membrane and analyzed by autoradiography. SEQ ID NOs:8 and 9 depict the 3H4 and 4D5 epitopes, respectively.

FIG. 2 depicts with underlining the amino acid sequence of Domain 1 of ErbB2 (SEQ ID NO:1). Bold amino acids indicate the location of the epitope recognized by MAbs 7C2 and 7F3 as determined by deletion mapping, i.e. the "7C2/7F3 epitope" (SEQ ID NO:2).

FIG. 3 is a graph of anti-ErbB2 antibody (HERCEPTIN®) trough serum concentration (µg/ml, mean±SE, dark circles) by week from week 2 through week 36 for ErbB2 overexpressing patients treated with HERCEPTIN® anti-ErbB2 antibody at 4 mg/kg initial dose, followed by 2 mg/kg weekly. The number of patients at each time point is represented by "n" (white squares).

FIG. 4A is a linear plot of tumor volume changes over time in mice treated with HERCEPTIN® anti-ErbB2 antibody. FIG. 4B is a semi-logarithmic plot of the same data as in FIG. 4A such that the variation in tumor volume for the treated animals is observed more readily.

FIGS. 5A and 5B depict alignments of the amino acid sequences of the variable light (V$_L$) (FIG. 5A) and variable heavy (V$_H$) (FIG. 5B) domains of murine monoclonal antibody 2C4 (SEQ ID Nos. 10 and 11, respectively); V$_L$ and V$_H$ domains of humanized Fab version 574 (SEQ ID Nos. 12 and 13, respectively), and human V$_L$ and V$_H$ consensus frameworks (hum κ1, light kappa subgroup I; humIII, heavy subgroup III) (SEQ ID Nos. 14 and 15, respectively). Asterisks identify differences between humanized Fab version 574 and murine monoclonal antibody 2C4 or between humanized Fab version 574 and the human framework. Complementarity Determining Regions (CDRs) are in brackets. Humanized Fab version 574, with the changes ArgH71Val, AspH73Arg and IleH69Leu, appears to have binding restored to that of the original chimeric 2C4 Fab fragment. Additional FR and/or CDR residues, such as L2, L54, L55, L56, H35 and/or H48, may be modified (e.g.

substituted as follows—IleL2Thr; ArgL54Leu; TyrL55Glu; ThrL56Ser; AspH35Ser; and ValH48Ile) in order to further refine or enhance binding of the humanized antibody. Alternatively, or additionally, the humanized antibody may be affinity matured in order to further improve or refine its affinity and/or other biological activities.

DETAILED DESCRIPTION OF THE
PREFERRED EMBODIMENTS

I. Definitions

An "ErbB receptor" is a receptor protein tyrosine kinase which belongs to the ErbB receptor family and includes EGFR, HER2, ErbB3 and ErbB4 receptors as well as TEGFR (U.S. Pat. No. 5,708,156) and other members of this family to be identified in the future. The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a native sequence ErbB receptor or an amino acid sequence variant thereof. Preferably the ErbB receptor is native sequence human ErbB receptor.

The terms "ErbB1", "epidermal growth factor receptor" and "EGFR" are used interchangeably herein and refer to native sequence EGFR as disclosed, for example, in Carpenter et al. *Ann. Rev. Biochem.* 56:881-914 (1987), including variants thereof (e.g. a deletion mutant EGFR as in Humphrey et al. *PNAS (USA)* 87:4207-4211 (1990)). erbB1 refers to the gene encoding the EGFR protein product. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225) and reshaped human 225 (H225) (see, WO 96/40210, Imclone Systems Inc.).

"ErbB3" and "HER3" refer to the receptor polypeptide as disclosed, for example, in U.S. Pat. Nos. 5,183,884 and 5,480,968 as well as Kraus et al. *PNAS (USA)* 86:9193-9197 (1989), including variants thereof. Examples of antibodies which bind HER3 are described in U.S. Pat. No. 5,968,511 (Akita and Sliwkowski), e.g. the 8B8 antibody (ATCC HB 12070) or a humanized variant thereof.

The terms "ErbB4" and "HER4" herein refer to the receptor polypeptide as disclosed, for example, in EP Pat Appln No 599,274; Plowman et al., *Proc. Natl. Acad. Sci. USA,* 90:1746-1750 (1993); and Plowman et al., *Nature,* 366:473-475 (1993), including variants thereof such as the HER4 isoforms disclosed in WO 99/19488.

The terms "HER2", "ErbB2" "c-Erb-B2" are used interchangeably. Unless indicated otherwise, the terms "ErbB2" "c-Erb-B2" and "HER2" when used herein refer to the human protein, and "erbB2," "c-erb-B2," and "her2" refer to human gene. The human erbB2 gene and ErbB2 protein are, for example, described in Semba et al., *PNAS (USA)* 82:6497-6501 (1985) and Yamamoto et al. *Nature* 319:230-234 (1986) (Genebank accession number X03363). ErbB2 comprises four domains (Domains 1-4).

The "epitope 4D5" is the region in the extracellular domain of ErbB2 to which the antibody 4D5 (ATCC CRL 10463) binds. This epitope is close to the transmembrane region of ErbB2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed (see FIG. 1) to assess whether the antibody binds to the 4D5 epitope of ErbB2 (i.e. any one or more residues in the region from about residue 529, e.g. about residue 561 to about residue 625, inclusive).

The "epitope 3H4" is the region in the extracellular domain of ErbB2 to which the antibody 3H4 binds. This epitope is shown in FIG. 1, and includes residues from about 541 to about 599, inclusive, in the amino acid sequence of ErbB2 extracellular domain.

The "epitope 7C2/7F3" is the region at the N-terminus of the extracellular domain of ErbB2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on ErbB2 (i.e. any one or more of residues in the region from about residue 22 to about residue 53 of ErbB2; SEQ ID NO:2).

The term "induces cell death" or "capable of inducing cell death" refers to the ability of the antibody to make a viable cell become nonviable. The "cell" here is one which expresses the ErbB2 receptor, especially where the cell overexpresses the ErbB2 receptor. A cell which "overexpresses" ErbB2 has significantly higher than normal ErbB2 levels compared to a noncancerous cell of the same tissue type. Preferably, the cell is a cancer cell, e.g. a breast, ovarian, stomach, endometrial, salivary gland, lung, kidney, colon, thyroid, pancreatic or bladder cell. In vitro, the cell may be a SKBR3, BT474, Calu 3, MDA-MB-453, MDA-MB-361 or SKOV3 cell. Cell death in vitro may be determined in the absence of complement and immune effector cells to distinguish cell death induced by antibody dependent cellular cytotoxicity (ADCC) or complement dependent cytotoxicity (CDC). Thus, the assay for cell death may be performed using heat inactivated serum (i.e. in the absence of complement) and in the absence of immune effector cells. To determine whether the antibody is able to induce cell death, loss of membrane integrity as evaluated by uptake of propidium iodide (PI), trypan blue (see Moore et al. Cytotechnology 17:1-11 [1995]) or 7AAD can be assessed relative to untreated cells. Preferred cell death-inducing antibodies are those which induce PI uptake in the "PI uptake assay in BT474 cells".

The phrase "induces apoptosis" or "capable of inducing apoptosis" refers to the ability of the antibody to induce programmed cell death as determined by binding of annexin V, fragmentation of DNA, cell shrinkage, dilation of endoplasmic reticulum, cell fragmentation, and/or formation of membrane vesicles (called apoptotic bodies). The cell is one which overexpresses the ErbB2 receptor. Preferably the "cell" is a tumor cell, e.g. a breast, ovarian, stomach, endometrial, salivary gland, lung, kidney, colon, thyroid, pancreatic or bladder cell. In vitro, the cell may be a SKBR3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering as disclosed in the example herein; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an "annexin binding assay using BT474 cells" (see below).

Sometimes the pro-apoptotic antibody will be one which blocks HRG binding/activation of the ErbB2/ErbB3 complex (e.g. 7F3 antibody). In other situations, the antibody is one which does not significantly block activation of the ErbB2/ErbB3 receptor complex by HRG (e.g. 7C2). Further, the antibody may be one like 7C2 which, while inducing apoptosis, does not induce a large reduction in the percent of cells in S phase (e.g. one which only induces about 0-10% reduction in the percent of these cells relative to control).

The antibody of interest may be one like 7C2 which binds specifically to human ErbB2 and does not significantly cross-react with other proteins such as those encoded by the erbB1, erbB3 and/or erbB4 genes. Sometimes, the antibody may not significantly cross-react with the rat neu protein, e.g., as described in Schecter et al. *Nature* 312:513 (1984) and Drebin et al., *Nature* 312:545-548 (1984). In such embodiments, the extent of binding of the antibody to these proteins (e.g., cell surface binding to endogenous receptor) will be less than about 10% as determined by fluorescence activated cell sorting (FACS) analysis or radioimmunoprecipitation (RIA).

"Heregulin" (HRG) when used herein refers to a polypeptide which activates the ErbB2-ErbB3 and ErbB2-ErbB4 protein complexes (i.e. induces phosphorylation of tyrosine residues in the complex upon binding thereto). Various heregulin polypeptides encompassed by this term are disclosed in Holmes et al., *Science*, 256:1205-1210 (1992); WO 92/20798; Wen et al., *Mol. Cell. Biol.*, 14(3):1909-1919 (1994); and Marchionni et al., *Nature*, 362:312-318 (1993), for example. The term includes biologically active fragments and/or variants of a naturally occurring HRG polypeptide, such as an EGF-like domain fragment thereof (e.g. HRGβ1$_{177-244}$).

The "ErbB2-ErbB3 protein complex" and "ErbB2-ErbB4 protein complex" are noncovalently associated oligomers of the ErbB2 receptor and the ErbB3 receptor or ErbB4 receptor, respectively. The complexes form when a cell expressing both of these receptors is exposed to HRG and can be isolated by immunoprecipitation and analyzed by SDS-PAGE as described in Sliwkowski et al., *J. Biol. Chem.*, 269(20):14661-14665 (1994).

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity determining regions (CDRs) or hypervariable regions both in the light-chain and the heavy-chain variable domains. The more highly conserved portions of variable domains are called the framework region (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FRs and, with the CDRs from the other chain, contribute to the formation of the antigen-binding site of antibodies (see Kabat et al., *NIH Publ. No.* 91-3242, Vol. I, pages 647-669 [1991]). The constant domains are not involved directly in binding an antibody to an antigen, but exhibit various effector functions, such as participation of the antibody in antibody dependent cellular cytotoxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "antibody" is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10):1057-1062 [1995]); single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity, and capacity. In some instances, framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDRs correspond to those of a non-human immunoglobulin and all or substantially all of the FRs are those of a human immunoglobulin sequence. The humanized antibody optimally also will comprise at least a portion of an immunoglobulin constant region (Fc), typically that of a human immunoglobulin. For further details, see Jones et al., *Nature*, 321:522-525 (1986); Reichmann et al., *Nature*, 332:323-329 (1988); and Presta, *Curr. Op. Struct. Biol.*, 2:593-596 (1992). The humanized antibody includes a PRIMATIZED™ antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the anti-ErbB2 antibody. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The term "therapeutically effective amount" is used to refer to an amount having antiproliferative effect. Preferably, the therapeutically effective amount has apoptotic activity, or is capable of inducing cell death, and preferably death of benign or malignant tumor cells, in particular cancer cells. Efficacy can be measured in conventional ways, depending on the condition to be treated. For cancer therapy, efficacy can, for example, be measured by assessing the time to disease progression (TTP), or determining the response rates (RR) (see Example 1, below). Therapeutically effective amount also refers to a target serum concentration, such as a trough serum concentration, that has been shown to be effective in suppressing disease symptoms when maintained for a period of time.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, prostate cancer, vulval cancer, thyroid cancer, hepatic carcinoma and various types of head and neck cancer.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially an ErbB2-overexpressing cancer cell either in vitro or in vivo. Thus, the growth inhibitory agent is one which significantly reduces the percentage of ErbB2 overexpressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders:

Philadelphia, 1995), especially p. 13. The 4D5 antibody (and functional equivalents thereof) can also be employed for this purpose.

"Doxorubicin" is an athracycline antibiotic. The full chemical name of doxorubicin is (8S-cis)-10-[(3-amino-2,3,6-trideoxy-α-L-lyxo-hexopyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above:

By "solid phase" is meant a non-aqueous matrix to which the antibodies used in accordance with the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "serum concentration," "serum drug concentration," or "serum HERCEPTIN® anti-ErbB2 antibody concentration" refers to the concentration of a drug, such as HERCEPTIN® anti-ErbB2 antibody, in the blood serum of an animal or human patient being treated with the drug. Serum concentration of HERCEPTIN® anti-ErbB2 antibody, for example, is preferably determined by immunoassay. Preferably, the immunoassay is an ELISA according to the procedure disclosed herein.

The term "peak serum concentration" refers to the maximal serum drug concentration shortly after delivery of the drug into the animal or human patient, after the drug has been distributed throughout the blood system, but before significant tissue distribution, metabolism or excretion of drug by the body has occurred.

The term "trough serum concentration" refers to the serum drug concentration at a time after delivery of a previous dose and immediately prior to delivery of the next subsequent dose of drug in a series of doses. Generally, the trough serum concentration is a minimum sustained efficacious drug concentration in the series of drug administrations. Also, the trough serum concentration is frequently targeted as a minimum serum concentration for efficacy because it represents the serum concentration at which another dose of drug is to be administered as part of the treatment regimen. If the delivery of drug is by intravenous administration, the trough serum concentration is most preferably attained within 1 day of a front loading initial drug delivery. If the delivery of drug is by subcutaneous administration, the peak serum concentration is preferably attained in 3 days or less. According to the invention, the trough serum concentration is preferably attained in 4 weeks or less, preferably 3 weeks or less, more preferably 2 weeks or less, most preferably in 1 week or less, including 1 day or less using any of the drug delivery methods disclosed herein.

The term "intravenous infusion" refers to introduction of a drug into the vein of an animal or human patient over a period of time greater than approximately 5 minutes, preferably between approximately 30 to 90 minutes, although, according to the invention, intravenous infusion is alternatively administered for 10 hours or less.

The term "intravenous bolus" or "intravenous push" refers to drug administration into a vein of an animal or human such that the body receives the drug in approximately 15 minutes or less, preferably 5 minutes or less.

The term "subcutaneous administration" refers to introduction of a drug under the skin of an animal or human patient, preferable within a pocket between the skin and underlying tissue, by relatively slow, sustained delivery from a drug receptacle. The pocket may be created by pinching or drawing the skin up and away from underlying tissue.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is preferably less than approximately 15 minutes, more preferably less than 5 minutes, and most preferably less than 60 seconds. Administration is preferably within a pocket between the skin and underlying tissue, where the pocket is created, for example, by pinching or drawing the skin up and away from underlying tissue.

The term "front loading" when referring to drug administration is meant to describe an initially higher dose followed by the same or lower doses at intervals. The initial higher dose or doses are meant to more rapidly increase the animal or human patient's serum drug concentration to an efficacious target serum concentration. According to the present invention, front loading is achieved by an initial dose or doses delivered over three weeks or less that causes the animal's or patient's serum concentration to reach a target serum trough concentration. Preferably, the initial front loading dose or series of doses is administered in two weeks or less, more preferably in 1 week or less, including 1 day or less. Most preferably, where the initial dose is a single dose and is not followed by a subsequent maintenance dose for at least 1 week, the initial dose is administered in 1 day or less. Where the initial dose is a series of doses, each dose is separated by at least 3 hours, but not more than 3 weeks or less, preferably 2 weeks or less, more preferably 1 week or less, most preferably 1 day or less. To avoid adverse immune reaction to an antibody drug such as an anti-ErbB2 antibody (e.g., HERCEPTIN® anti-ErbB2 antibody) in an animal or patient who has not previously been treated with the antibody, it may be preferable to deliver initial doses of the antibody by intravenous infusion. The present invention includes front loading drug delivery of initial and maintenance doses by infusion or bolus administration, intravenously or subcutaneously.

Published information related to anti-ErbB2 antibodies includes the following issued patents and published applications: PCT/US89/00051, published Jan. 5, 1989; PCT/US90/02697, published May 18, 1990; EU 0474727 issued Jul. 23, 1997; DE 69031120.6, issued Jul. 23, 1997; PCT/US97/18385, published Oct. 9, 1997; SA 97/9185, issued Oct. 14, 1997; U.S. Pat. No. 5,677,171, issued Oct. 14, 1997; U.S. Pat. No. 5,720,937, issued Feb. 24, 1998; U.S. Pat. No. 5,720,954, issued Feb. 24, 1998; U.S. Pat. No. 5,725,856, issued Mar. 10, 1998; U.S. Pat. No. 5,770,195, issued Jun. 23, 1998; U.S. Pat. No. 5,772,997, issued Jun. 30, 1998; PCT/US98/2626, published Dec. 10, 1998; and PCT/US99/06673, published Mar. 26, 1999, each of which patents and publications is herein incorporated by reference in its entirety.

II. Production of Anti-ErbB2 Antibodies

A description follows as to exemplary techniques for the production of the antibodies used in accordance with the present invention. The ErbB2 antigen to be used for production of antibodies may be, e.g., a soluble form of the extracellular domain of ErbB2 or a portion thereof, containing the desired epitope. Alternatively, cells expressing ErbB2 at their cell surface (e.g. NIH-3T3 cells transformed to overexpress ErbB2; or a carcinoma cell line such as SKBR3 cells, see Stancovski et al., *PNAS (USA)* 88:8691-8695 [1991]) can be used to generate antibodies. Other forms of ErbB2 useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N$=C=NR, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 [Marcel Dekker, Inc., New York, 1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 [Academic Press, 1986]). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130:151-188 (1992).

In a further embodiment, antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 [1992]), as well as combinatorial infection and in vivo recombination as a strategy for constructing very large phage libraries (Waterhouse et al., *Nuc. Acids. Res.*, 21:2265-2266 [1993]). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 [1984]), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized and Human Antibodies

Methods for humanizing non-human antibodies are well known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 [1988]), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 [1987]). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immnol.*, 151:2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993). Human antibodies can also be derived from phage-display libraries (Hoogenboom et al., *J. Mol. Biol.*, 227:381 (1991); Marks et al., *J. Mol. Biol.*, 222:581-597 [1991]).

(iv) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229:81 [1985]). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 [1992]). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(v) Bispecific Antibodies

Bispecific antibodies are antibodies that have binding specificities for at least two different epitopes. Exemplary bispecific antibodies may bind to two different epitopes of the ErbB2 protein. For example, one arm may bind an epitope in Domain 1 of ErbB2 such as the 7C2/7F3 epitope, the other may bind a different ErbB2 epitope, e.g. the 4D5 epitope. Other such antibodies may combine an ErbB2 binding site with binding site(s) for EGFR, ErbB3 and/or ErbB4. Alternatively, an anti-ErbB2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the ErbB2-expressing cell. Bispecific antibodies may also be used to localize cytotoxic agents to cells which express ErbB2. These antibodies possess an ErbB2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 [1983]). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147: 60 (1991).

(vi) Screening for Antibodies with the Desired Properties

Techniques for generating antibodies have been described above. Those antibodies having the characteristics described herein are selected.

To select for antibodies which induce cell death, loss of membrane integrity as indicated by, e.g., PI, trypan blue or 7AAD uptake is assessed relative to control. The preferred assay is the "PI uptake assay using BT474 cells". According to this assay, BT474 cells (which can be obtained from the American Type Culture Collection [Rockville, Md.]) are cultured in Dulbecco's Modified Eagle Medium (D-MEM): Ham's F-12 (50:50) supplemented with 10% heat-inactivated FBS (Hyclone) and 2 mM L-glutamine. (Thus, the assay is performed in the absence of complement and immune effector cells). The BT474 cells are seeded at a density of 3×10$^6$ per dish in 100×20 mm dishes and allowed to attach overnight. The medium is then removed and replaced with fresh medium alone or medium containing 10 µg/ml of the appropriate MAb. The cells are incubated for a 3 day time period. Following each treatment, monolayers are washed with PBS and detached by trypsinization. Cells are then centrifuged at 1200 rpm for 5 minutes at 4° C., the pellet resuspended in 3 ml ice cold Ca$^{2+}$ binding buffer (10 mM Hepes, pH 7.4, 140 mM NaCl, 2.5 mM CaCl$_2$) and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake are selected.

In order to select for antibodies which induce apoptosis, an "annexin binding assay using BT474 cells" is available. The BT474 cells are cultured and seeded in dishes as discussed in the preceding paragraph. The medium is then removed and replaced with fresh medium alone or medium containing 10 µg/ml of the MAb. Following a three day incubation period, monolayers are washed with PBS and detached by trypsinization. Cells are then centrifuged, resuspended in Ca$^{2+}$ binding buffer and aliquoted into tubes as discussed above for the cell death assay. Tubes then receive labeled annexin (e.g. annexin V-FTIC) (1 µg/ml). Samples may be analyzed using a FACSCAN™ flow cytometer and FACSCONVERT™ CellQuest software (Becton Dickinson). Those antibodies which induce statistically significant levels of annexin binding relative to control are selected as apoptosis-inducing antibodies.

In addition to the annexin binding assay, a "DNA staining assay using BT474 cells" is available. In order to perform this assay, BT474 cells which have been treated with the antibody of interest as described in the preceding two paragraphs are incubated with 9 µg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay.

To screen for antibodies which bind to an epitope on ErbB2 bound by an antibody of interest, a routine cross-blocking assay such as that described in *Antibodies, A Laboratory Manual*, Cold Spring Harbor Laboratory, Ed Harlow and David Lane (1988), can be performed. Alternatively, epitope mapping can be performed by methods known in the art.

To identify anti-ErbB2 antibodies which inhibit growth of SKBR3 cells in cell culture by 50-100%, the SKBR3 assay described in WO 89/06692 can be performed. According to this assay, SKBR3 cells are grown in a 1:1 mixture of F12 and DMEM medium supplemented with 10% fetal bovine serum, glutamine and penicillinstreptomycin. The SKBR3 cells are plated at 20,000 cells in a 35 mm cell culture dish (2 mls/35 mm dish). 2.5 µg/ml of the anti-ErbB2 antibody is added per dish. After six days, the number of cells, compared to untreated cells are counted using an electronic COULTER™ cell counter. Those antibodies which inhibit growth of the SKBR3 cells by 50-100% are selected for combination with the apoptotic antibodies as desired.

(vii) Effector Function Engineering

It may be desirable to modify the antibody of the invention with respect to effector function, so as to enhance the effectiveness of the antibody in treating cancer, for example. For example, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

(viii) Immunoconjugates

The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. A variety of radionuclides are available for the production of radioconjugated anti-ErbB2 antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(ix) Immunoliposomes

The anti-ErbB2 antibodies disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19)1484 (1989).

(x) Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO 81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 [1987]). Antibody-abzyme conjugates can be prepared as described herein for delivery of the abzyme to a tumor cell population.

The enzymes of this invention can be covalently bound to the anti-ErbB2 antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature*, 312: 604-608 [1984]).

(xi) Antibody-Salvage Receptor Binding Epitope Fusions

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g. by mutation of the appropriate region in the antibody fragment or by incorporating the epitope into a peptide tag that is then fused to the antibody fragment at either end or in the middle, e.g., by DNA or peptide synthesis).

A systematic method for preparing such an antibody variant having an increased in vivo half-life comprises several steps. The first involves identifying the sequence and conformation of a salvage receptor binding epitope of an Fc region of an IgG molecule. Once this epitope is identified, the sequence of the antibody of interest is modified to include the sequence and conformation of the identified binding epitope. After the sequence is mutated, the antibody variant is tested to see if it has a longer in vivo half-life than that of the original antibody. If the antibody variant does not have a longer in vivo half-life upon testing, its sequence is further altered to include the sequence and conformation of the identified binding epitope. The altered antibody is tested for longer in vivo half-life, and this process is continued until a molecule is obtained that exhibits a longer in vivo half-life.

The salvage receptor binding epitope being thus incorporated into the antibody of interest is any suitable such epitope as defined above, and its nature will depend, e.g., on the type of antibody being modified. The transfer is made such that the antibody of interest still possesses the biological activities described herein.

The epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

In one most preferred embodiment, the salvage receptor binding epitope comprises the sequence (5' to 3'): PKNSSMISNTP (SEQ ID NO:3), and optionally further comprises a sequence selected from the group consisting of HQSLGTQ (SEQ ID NO:4), HQNLSDGK (SEQ ID NO:5), HQNISDGK (SEQ ID NO:6), or VISSHLGQ (SEQ ID NO:7), particularly where the antibody fragment is a Fab or F(ab)$_2$. In another most preferred embodiment, the salvage receptor binding epitope is a polypeptide containing the sequence(s) (5' to 3'): HQNLSDGK (SEQ ID NO:5), HQNISDGK (SEQ ID NO:6), or VISSHLGQ (SEQ ID NO:7) and the sequence: PKNSSMISNTP (SEQ ID NO:3).

(xii) Purification of Anti-ErbB2 Antibody

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are preferably first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 [1983]). Protein G is recommended for all mouse isotypes and for human γ3 (Guss et al., *EMBO J.* 5:15671575 [1986]). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g. from about 0-0.25M salt).

III. Determination of Anti-ErbB2 Antibody Concentration in Serum

The following non-limiting assay is useful for determining the presence of and to quantitate the amount of specific rhuMAb HER2 (humanized anti-p185$^{HER2}$ monoclonal antibody, including HERCEPTIN® anti-ErbB2 antibody) in a body fluid of a mammal including, but not limited to, serum, amniotic fluid, milk, umbilical cord serum, ocular aqueous and vitreous liquids, and ocular vitreous gel.

Plate Binding Activity Assay for rhuMAb HER2 (Humanized Anti-p185$^{HER2}$ Monoclonal Antibody The method of assaying rhuMAb HER2 described herein is meant as an example of such a method and is not meant to be limiting. A standardized preparation of rhuMAb HER2 (Genentech, Inc., South San Francisco, Calif.), controls, and serum samples were diluted with Assay Diluent (PBS/0.5% BSA/0.05% Polysorbate 20/0.01% Thimerosal). The dilutions of standardized rhuMAb HER2 were prepared to span a range of concentrations useful for a standard curve. The samples were diluted to fall within the standard curve.

An aliquot of Coat Antigen in Coating buffer (recombinant p185$^{HER2}$ (Genentech, Inc.) in 0.05 M sodium carbonate buffer) was added to each well of a microtiter plate and incubated at 2-8° C. for 12-72 hours. The coating solution was removed and each well was washed six times with water, then blotted to remove excess water:

An aliquot of Assay Diluent was added to each well and incubated for 1-2 hours at ambient temperature with agitation. The wells were washed as in the previous step.

Aliquots of diluted standard, control and sample solutions were added to the wells and incubated at ambient temperature for 1 hour with agitation to allow binding of the antibody to the coating antigen. The wells are washed again with water as in previous steps.

Horse radish peroxidase-conjugate (HRP-conjugate, Goat anti-human IgG Fc conjugated to horseradish peroxidase; Organon Teknika catalog #55253 or equivalent) was diluted with Assay Diluent to yield an appropriate optical density range between the highest and lowest standards. An aliquot of the HRP-conjugate solution was added to each well and incubated at ambient temperature for 1 hour with agitation. The wells were washed with water as in previous steps.

An aliquot of Substrate Solution (o-phenylenediamine (OPD) 5 mg tablet (Sigma P6912 or equivalent) in 12.5 ml 4 mM $H_2O_2$ in PBS) was added to each well and incubated for a sufficient period of time (approximately 8-10 minutes) in the dark at ambient temperature to allow color development. The reaction was stopped with an aliquot of 4.5 N sulfuric acid. Optical density was read at 490-492 nm for detection absorbance and 405 nm for reference absorbance. The standard curve data are plotted and the results for the controls and samples are determined from the standard curve.

IV. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as TWEEN™, PLURONICS™ or polyethylene glycol (PEG). Preferred lyophilized anti-ErbB2 antibody formulations are described in WO 97/04801, expressly incorporated herein be reference.

The formulation herein may also contain more than one active compound as necessary for the particular indication being treated, preferably those with complementary activities that do not adversely affect each other. For example, it may be desirable to further provide antibodies which bind to EGFR, ErbB2 (e.g. an antibody which binds a different epitope on ErbB2), ErbB3, ErbB4, or vascular endothelial growth factor (VEGF) in the one formulation. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

V. Treatment with the Anti-ErbB2 Antibodies

It is contemplated that, according to the present invention, the anti-ErbB2 antibodies may be used to treat various conditions characterized by overexpression and/or activation of the ErbB2 receptor. Exemplary conditions or disorders include benign or malignant tumors (e.g. renal, liver, kidney, bladder, breast, gastric, ovarian, colorectal, prostate, pancreatic, lung, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders.

The antibodies of the invention are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

The treatment of the present invention involves the administration of an anti-ErbB2 antibody to an animal or human patient, followed at intervals by subsequent doses of equal or smaller doses such that a target serum concentration is achieved and maintained during treatment. Preferably, maintenance doses are delivered by bolus delivery, preferably by subcutaneous bolus administration, making treatment convenient and cost-effective for the patient and health care professionals.

Where combined administration of a chemotherapeutic agent (other than an antracycline) is desired, the combined administration includes coadministration, using separate formulations or a single pharmaceutical formulation, and consecutive administration in either order, wherein preferably there is a time period while both (or all) active agents simultaneously exert their biological activities. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration of the antibody or may be given simultaneously therewith. The antibody may be combined with an anti-estrogen compound such as tamoxifen or an anti-progesterone such as onapristone (see, EP 616 812) in dosages known for such molecules.

It may be desirable to also administer antibodies against other tumor associated antigens, such as antibodies which bind to the EGFR, ErbB3, ErbB4, or vascular endothelial growth factor (VEGF). Alternatively, or additionally, two or more anti-ErbB2 antibodies may be co-administered to the patient. Sometimes, it may be beneficial to also administer one or more cytokines to the patient. The ErbB2 antibody may be co-administered with a growth inhibitory agent. For example, the growth inhibitory agent may be administered first, followed by the ErbB2 antibody. However, simultaneous administration, or administration of the ErbB2 antibody first is also contemplated. Suitable dosages for the growth inhibitory agent are those presently used and may be lowered due to the combined action (synergy) of the growth inhibitory agent and anti-ErbB2 antibody.

In addition to the above therapeutic regimens, the patient may be subjected to surgical removal of cancer cells and/or radiation therapy.

For the prevention or treatment of disease, the appropriate dosage of anti-ErbB2 antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Where the treatment involves a series of treatments, the initial dose or initial doses are followed at daily or weekly intervals by maintenance doses. Each maintenance dose provides the same or a smaller amount of antibody compared to the amount of antibody administered in the initial dose or doses.

Depending on the type and severity of the disease, about 1 µg/kg to 15 mg/kg (e.g. 0.1-20 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy is easily monitored by conventional techniques and assays.

According to the invention, dosage regimens may include an initial dose of anti-ErbB2 of 6 mg/kg, 8 mg/kg, or 12 mg/kg delivered by intravenous or subcutaneous infusion, followed by subsequent weekly maintenance doses of 2 mg/kg by intravenous infusion, intravenous bolus injection, subcutaneous infusion, or subcutaneous bolus injection. Where the antibody is well-tolerated by the patient, the time of infusion may be reduced.

Alternatively, the invention includes an initial dose of 12 mg/kg anti-ErbB2 antibody, followed by subsequent maintenance doses of 6 mg/kg once per 3 weeks.

Another dosage regimen involves an initial dose of 8 mg/kg anti-ErbB2 antibody, followed by 6 mg/kg once per 3 weeks.

Still another dosage regimen involves an initial dose of 8 mg/kg anti-ErbB2 antibody, followed by subsequent maintenance doses of 8 mg/kg once per week or 8 mg/kg once every 2 to 3 weeks.

As an alternative regimen, initial doses of 4 mg/kg anti-ErbB2 antibody may be administered on each of days 1, 2 and 3, followed by subsequent maintenance doses of 6 mg/kg once per 3 weeks.

An additional regimen involves an initial dose of 4 mg/kg anti-ErbB2 antibody, followed by subsequent maintenance doses of 2 mg/kg twice per week, wherein the maintenance doses are separated by 3 days.

Alternatively, the invention may include a cycle of dosing in which delivery of anti-ErbB2 antibody is 2-3 times per week for 3 weeks. The 3 week cycle is preferably repeated as necessary to achieve suppression of disease symptoms.

The invention further includes a cyclic dosage regimen in which delivery of anti-ErbB2 antibody is daily for 5 days. According to the invention, the cycle is preferably repeated as necessary to achieve suppression of disease symptoms. Further information about suitable dosages is provided in the Examples below.

VI. Articles of Manufacture

In another embodiment of the invention, an article of manufacture containing materials useful for the treatment of the disorders described above is provided. The article of manufacture comprises a container, a label and a package insert. Suitable containers include, for example, bottles, vials, syringes, etc. The containers may be formed from a variety of materials such as glass or plastic. The container holds a composition which is effective for treating the condition and may have a sterile access port (for example, the container may be an intravenous solution bag or a vial having a stopper pierceable by a hypodermic injection needle). At least one active agent in the composition is an anti-ErbB2 antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, and syringes. In addition, the article of manufacture may comprise a package inserts with instructions for use, including, e.g., a warning that the composition is not to be used in combination with anthacycline-type chemotherapeutic agent, e.g. doxorubicin or epirubicin.

Deposit of Materials

The following hybridoma cell lines have been deposited with the American Type Culture Collection, 12301 Parklawn Drive, Rockville, Md., USA (ATCC):

| Antibody Designation | ATCC No. | Deposit Date |
| --- | --- | --- |
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |
| 2C4 | ATCC HB-12697 | Apr. 8, 1999 |

Further details of the invention are illustrated by the following non-limiting Examples.

EXAMPLES

Example 1: Preparation and Efficacy of HERCEPTIN® Anti-ErbB2 Antibody

Materials and Methods

Anti-ErbB2 Monoclonal Antibody

The anti-ErbB2 IgG$_1$κ murine monoclonal antibody 4D5, specific for the extracellular domain of ErbB2, was produced as described in Fendly et al., *Cancer Research* 5o:1550-1558 (1990) and WO89/06692. Briefly, NIH 3T3/HER2-3$_{400}$ cells (expressing approximately 1×10$^5$ ErbB2 molecules/cell) produced as described in Hudziak, et al., *Proc. Natl. Acad. Sci.* (*USA*) 84:7159 (1987) were harvested with phosphate buffered saline (PBS) containing 25 mM EDTA and used to immunize BALB/c mice. The mice were given injections i.p. of 10$^7$ cells in 0.5 ml PBS on weeks, 0, 2, 5 and 7. The mice with antisera that immunoprecipitated $^{32}$P-labeled ErbB2 were given i.p. injections of a wheat germ agglutinin-Sepharose (WGA) purified ErbB2 membrane extract on weeks 9 and 13. This was followed by an i.v. injection of 0.1 ml of the ErbB2 preparation and the splenocytes were fused with mouse myeloma line X63-Ag8.653. Hybridoma supernatants were screened for ErbB2-binding by ELISA and radioimmunoprecipitation. MOPC-21 (IgG1), (Cappell, Durham, N.C.), was used as an isotype-matched control.

The treatment was performed with a humanized version of the murine 4D5 antibody (HERCEPTIN® anti-ErbB2 antibody). The humanized antibody was engineered by inserting the complementarity determining regions of the murine 4D5 antibody into the framework of a consensus human immunoglobulin IgG$_1$ (IgG$_1$) (Carter et al., *Proc. Natl. Acad. Sci. USA* 89:4285-4289 [1992]). The resulting humanized anti-ErbB2 monoclonal antibody has high affinity for p185$^{HER2}$ (Dillohiation constant [K$_d$]=0.1 nmol/L), markedly inhibits, in vitro and in human xenografts, the growth of breast cancer cells that contain high levels of p185$^{HER2}$, induces antibody-dependent cellular cytotoxicity (ADCC), and has been found clinically active, as a single agent, in patients with ErbB2-overexpressing metastatic breast cancers that had received extensive prior therapy. HERCEPTIN® anti-ErbB2 antibody is produced by a genetically engineered Chinese Hamster Ovary (CHO) cell line, grown in large scale, that secretes the antibody into the culture medium. The antibody is purified from the CHO culture media using standard chromatographic and filtration methods. Each lot of antibody used in this study was assayed to verify identity, purity, and potency, as well as to meet Food and Drug Administration requirements for sterility and safety.

Eligibility Criteria

Patients had to fulfill all of the following criteria to be eligible for study admission:

Metastatic breast cancer

Overexpression of the ErbB2 (HER2) oncogene (2+ to 3+ as determined by immunohistochemistry or fluorescence in situ hybridization (FISH). [Tumor expression of ErbB2 can be determined by immunohistochemical analysis, as previously described (Slamon et al., [1987] and [1989], supra), of a set of thin sections prepared from the patient's paraffin-archived tumor blocks. The primary detecting antibody used is murine 4D5 MAb, which has the same CDRs as the humanized antibody used for the treatment. Tumors are considered to overexpress ErbB2 if at least 25% of tumor cells exhibit characteristic membrane staining for p185$^{HER2}$].

Bidimensionally measurable disease (including lytic bone lesions) by radiographic means, physical examination, or photographs Measurable disease was defined as any mass reproducibly measurable in two perpendicular diameters by physical examination, X-ray (plain films), computerized tomography (CT), magnetic resonance imaging (MRI), ultrasound, or photographs.

Osteoblastic metastases, pleural effusions, or ascites were not considered to be measurable. Measurable lesions must be at least 1 cm in greatest dimension. Enumeration of evaluable sites of metastatic disease and number of lesions in an evaluable site (e.g. lung) had to be recorded on the appropriate Case Report Form (CRF). If a large number of pulmonary or hepatic lesions were present, the six largest lesions per site were followed.

The ability to understand and willingness to sign a written informed consent form Women ≤18 years Suitable candidates for receiving concomitant cytotoxic chemotherapy as evidenced by screening laboratory assessments of hematologic, renal, hepatic, and metabolic functions.

Exclusion Criteria

Patients with any of the following were excluded from study entry:

Prior cytotoxic chemotherapy for metastatic breast cancer

Patients may have received prior hormonal therapy (e.g. tamoxifen) for metastatic disease or cytotoxic therapy in the adjuvant setting.

Concomitant malignancy that has not been curatively treated

A performance status of <60% on the Karnofsky scale

Pregnant or nursing women; women of childbearing potential, unless using effective contraception as determined by the investigator Bilateral breast cancer (either both primary tumors must have 2+ to 3+ HER2 overexpression, or the metastatic site must have 2+ to 3+ HER2 overexpression)

Use of investigational or unlicensed agents within 30 days prior to study entry

Clinically unstable or untreated metastases to the brain (e.g. requiring radiation therapy)

Based upon the foregoing criteria, 469 patients were chosen, and enrolled in the study. Half the patients (stratified by chemotherapy) were randomized to additionally receive the HERCEPTIN® anti-ErbB2 antibody (see below).

Administration and Dosage

Anti-ErbB2 Antibody

On day 0, a 4 mg/kg dose of humanized anti-ErbB2 antibody (HERCEPTIN®, H) was administered intravenously, over a 90-minute period. Beginning on day 7, patients received weekly administration of 2 mg/kg antibody (i.v.) over a 90-minute period.

Chemotherapy

The patients received one of two chemotherapy regimens for a minimum of six cycles, provided their disease was not progressing: a) cyclophosphamide and doxorubicin or epirubicin (AC), if patients have not received anthracycline therapy in the adjuvant setting, or b) paclitaxel (T, TAXOL®), if patients have received any anthracycline therapy in the adjuvant setting. The initial dose of the HERCEPTIN® anti-ErbB2 antibody preceded the first cycle of either chemotherapy regimen by 24 hours. Subsequent doses of the antibody were given immediately before chemotherapy administration, if the initial dose of the antibody was well tolerated. If the first dose of the antibody was not well tolerated, subsequent infusions continued to precede chemotherapy administration by 24 hours. Patients were permitted to continue receiving chemotherapy beyond six cycles if, in the opinion of the treating physician, they were continuing to receive treatment benefit.

Cyclophosphamide (600 mg/m$^2$) was given either by iv push over a minimum period of 3 minutes or by infusion over a maximum period of 2 hours.

Doxorubicin (60 mg/m$^2$) or epirubicin (75 mg/m$^2$) were given either by slow iv push over a minimum period of 3-5 minutes or by infusion over a maximum period of 2 hours, according to institutional protocol.

Paclitaxel (TAXOL®) was given at a dose of 175 mg/m$^2$ over 3 hours by intravenous administration. All patients receiving paclitaxel were premedicated with dexamethasone (or its equivalent) 20 mg×2, administered orally 12 and 6 hours prior to paclitaxel; diphenhydramine (or its equivalent) 50 mg, iv, administered 30 minutes prior to paclitaxel, and dimetidine (or another H$_2$ blocker) 300 mg, iv, administered 30 minutes prior to paclitaxel.

Response Criteria

Progressive Disease

Objective evidence of an increase of 25% or more in any measurable lesion. Progressive disease also includes those instances when new lesions have appeared. For bone lesions, progression is defined as a 25% increase in objective measurement by plain film, CT, MRI; symptomatic new lesions not due to fracture; or requirement for palliative radiotherapy.

Complete Response

Disappearance of all radiographically and/or visually apparent tumor for a minimum of 4 weeks. Skin and chest wall complete responses had to be confirmed by biopsy.

Partial Response

A reduction of at least 50% in the sum of the products of the perpendicular diameters of all measurable lesions for a minimum period of 4 weeks. No new lesions may have appeared, nor may any lesions have progressed in size.

Minor Response

A reduction of 25% to 49% in the sum of the products of the perpendicular diameters of all measurable lesions. No new lesions may have appeared, nor may any lesions have progressed in size.

Stable Disease

No change of greater than 25% in the size of measurable lesions. No lesions may have appeared.

Time to disease progression (TTP) was calculated from the beginning of therapy to progression.

Confidence limits for response rates were calculated using the exact method for a single proportion. (Fleiss, J L, *Statistical Methods for Rates and Proportions* (ed. 2), New York, N.Y., Wiley, 1981, pp 13-17).

Results

At a median follow-up of 10.5 months, assessments of time to disease progression (TTP in months) and response rates (RR) showed a significant augmentation of the chemotherapeutic effect by HERCEPTIN® anti-ErbB2 antibody, without increase in overall severe adverse events (AE):

TABLE 1

HERCEPTIN ® Anti-ErbB2 Antibody Efficacy

|  | Enrolled | TTP (months) | RR (%) | AE (%) |
| --- | --- | --- | --- | --- |
| CRx | 234 | 5.5 | 36.2 | 66 |
| CRx + H | 235 | 8.6* | 62.00** | 69 |
| AC | 145 | 6.5 | 42.1 | 71 |
| AC + H | 146 | 9.0 | 64.9 | 68 |
| T | 89 | 4.2 | 25.0 | 59 |
| T + H | 89 | 7.1 | 57.3 | 70 |

*p < 0.001 by log-rank test;
**p < 0.01 by X$^2$ test;
CRx: chemotherapy;
AC: anthracycline/cyclophosphamide treatment;
H: HERCEPTIN ® anti-ErbB2 antibody;
T: TAXOL ®

A syndrome of myocardial dysfunction similar to that observed with anthracyclines was reported more commonly with a combined treatment of AC+H (18% Grade 3/4) than with AC alone (3%), T (0%), or T+H (2%).

These data indicate that the combination of anti-ErbB2 antibody treatment with chemotherapy markedly increases the clinical benefit, as assessed by response rates and the evaluation of disease progression. However, due to the increased cardiac side-effects of doxorubicin or epirubicin, the combined use of anthracyclines with anti-ErbB2 antibody therapy is contraindicated. The results, taking into account risk and benefit, favor treatment with HERCEPTIN® anti-ErbB2 antibody and paclitaxel (TAXOL®) where a combined treatment regimen is desired.

Example 2: Pharmacokinetic and Pharmacodynamic Properties of Anti-ErbB2 Antibody (HERCEPTIN®)

HERCEPTIN® anti-ErbB2 antibody was administered by intravenous infusion to human patients selected according to the criteria provided in Example 1. An initial dose of 4 mg/kg HERCEPTIN® anti-ErbB2 antibody was delivered by intravenous infusion, followed by subsequent i.v. infusions of 2 mg/kg HERCEPTIN® anti-ErbB2 antibody weekly for several weeks. Two hundred thirteen patients began this treatment regimen and serum drug concentration was obtained beyond 8 weeks for fewer than 90 patients as selective discontinuation of patients with rapidly progressing disease occurred. Of the 213 patients who began treatment, serum trough concentration data were available for 80 patients at Week 12, for 77 patients at Week 16, for 44 patients at Week 20, for 51 patients at Week 24, for 25 patients at Week 28, for 23 patients at Week 32, and for 37 patients at Week 36.

HERCEPTIN® Anti-ErbB2 Antibody Trough Serum Concentrations for Weeks 0-36

The HERCEPTIN® anti-ErbB2 antibody trough serum concentrations (µg/ml, mean±SE) from Week 2 through Week 36 are plotted in FIG. 3 (dark circles). The number of patients was fairly constant because data from patients discontinued from the program due to rapidly progressing disease were excluded from this analysis. Trough serum concentrations tended to increase through Week 12 and tended to plateau after that time.

HERCEPTIN® Anti-ErbB2 Antibody Trough and Peak Serum Concentrations for Weeks 1-8

Some HERCEPTIN® anti-ErbB2 antibody serum concentration data were available for 212 of the original 213 patients. Trough and peak serum concentration data reflecting the first HERCEPTIN® anti-ErbB2 antibody infusion were available for 195 of the 212 patients. For the seventh infusion, trough serum concentration data were available for 137/212 patients and peak serum concentration data were available for 114/212 patients. Table 2 presents a summary of statistics from trough and peak serum concentrations for the first 8 weeks of treatment. Peak samples were drawn shortly after the end of HERCEPTIN® anti-ErbB2 antibody administration; trough samples were drawn prior to the subsequent dose (i.e., 1 week later). Serum concentrations of HERCEPTIN® anti-ErbB2 antibody were determined as disclosed herein.

TABLE 2

HERCEPTIN ® Anti-ErbB2 Antibody Trough and Peak Serum Concentrations for the First 8 Weeks of Treatment (µg/ml)

| | Dose Number | n | Mean | SD | Minimun | Maximum |
|---|---|---|---|---|---|---|
| Peak | 1 | 195 | 100.3 | 35.2 | 30.7 | 274.6 |
| Trough | | 195 | 25.0 | 12.7 | 0.16 | 60.7 |
| Peak | 2 | 190 | 74.3 | 31.3 | 20.8 | 307.9 |
| Trough | | 167 | 30.4 | 16.0 | 0.2 | 74.4 |
| Peak | 3 | 167 | 75.3 | 26.8 | 16.1 | 194.8 |
| Trough | | 179 | 33.7 | 17.9 | 0.2 | 98.2 |
| Peak | 4 | 175 | 80.2 | 26.9 | 22.2 | 167 |
| Trough | | 132 | 38.6 | 20.1 | 0.2 | 89.4 |
| Peak | 5 | 128 | 85.9 | 29.2 | 27.8 | 185.8 |
| Trough | | 141 | 42.1 | 24.8 | 0.2 | 148.7 |
| Peak | 6 | 137 | 87.2 | 32.2 | 28.9 | 218.1 |
| Trough | | 115 | 43.2 | 24.0 | 0.2 | 109.9 |
| Peak | 7 | 114 | 89.7 | 32.5 | 16.3 | 187.8 |
| Trough | | 137 | 48.8 | 24.9 | 0.2 | 105.2 |
| Peak | 8 | 133 | 95.6 | 35.9 | 11.4 | 295.6 |

The data in Table 2 suggest that there was an increase in trough serum concentration over time. Of the many patients studied, there were 18 patients for whom the trough concentrations did not exceed 20 µg/ml from Week 2 through Week 8. A HERCEPTIN® anti-ErbB2 antibody trough serum concentration of 20 µg/ml was nominally targeted for these studies based on prior pharmacologic studies in animals and exploratory analyses in clinical trials.

Patient response status was evaluated relative to serum concentration of HERCEPTIN® anti-ErbB2 antibody. For this purpose, mean serum concentration (an average of troughs and peaks) was calculated for various times and patient response status (where the patient response status was determined by an independent Response Evaluation Committee). The increase in serum concentration between Weeks 2 and 8 appeared to be greater in responders than in nonresponders, suggesting that there is a relationship between response status and HERCEPTIN® anti-ErbB2 antibody serum concentration. A statistical analysis (analysis of variance) of trough serum concentration values at Week 2 and an average of Weeks 7 and 8 in relation to response status indicated a highly significant relationship between response status and average trough of Weeks 7 and 8 ($p<0.001$). The results indicated that there was a significant difference between the trough serum concentration (average troughs of Weeks 7 and 8) in the responders and nonresponders: trough concentrations were 60±20 µg/ml in the responders versus 44±25 µg/ml in the nonresponders (mean±SD). HER2 overexpression level and type of metastatic sites were associated with significant differences in trough serum concentrations. At Week 2, patients with 2+ HER2 overexpression had significantly higher trough serum concentrations (n=40, mean=28.8 µg/ml, SD=10.4) compared with patients with 3+ HER2 overexpression (n=155, mean=24.1 µg/ml, SD=13.1). This difference in the average trough serum concentrations for Weeks 7 and 8 was no longer statistically significant. Further, at Week 2, patients with superficial disease had significantly higher trough serum concentrations (n=12, mean 34.1 µg/ml, SD=12.0) compared with patients with visceral disease (n=183, mean=24.4 µg/ml, SD=12.6). This difference in the average trough serum concentrations for Weeks 7 and 8 was significant. These data indicate that the rise in trough serum concentrations between Weeks 2 and 7/8 occurs for human patients with various disease profiles.

In a subsequent, similarly designed study, human breast cancer patients were treated with a loading dose of 8 mg/kg followed by maintenance doses of 4 mg/kg weekly. The results of this preliminary human study indicated that an 8 mg/kg load:4 mg/kg weekly maintenance regimen was efficacious in reducing tumor volume in the patients.

The data disclosed in this Example indicate that front loading of antibody, such that a target serum concentration is reached more quickly, may be associated with improved outcomes.

Example 3: I.V. Bolus Delivery and Subcutaneous Infusion of HERCEPTIN® Anti-ErbB2 Antibody Effectively Decrease Tumor Volume in the Mouse The efficacy of infusion or bolus delivery of humanized anti-ErbB2 antibody (HERCEPTIN® see Example 1 for preparation), either by intravenous injection or subcutaneous injection, was examined. The purpose of the study was to ask whether subcutaneous delivery was feasible and whether the convenient subcutaneous bolus delivery was useful in treating metastatic breast cancer in animals inoculated with a cell line that overexpresses the HER2 gene. The results, detailed below, show that i.v. and s.c. infusion and bolus delivery are feasible treatment methodologies.

A study in a nude mouse xenograft model, which incorporates a human breast cancer cell line that naturally overexpresses the HER2 gene (BT-474M1, derived from BT-474 cells, ATCC Accession number HTB-20), comparing tumor volume as a function of i.v. bolus versus s.c. infusion was performed as follows. In the first study athymic nude nu nu 7-9 week old female mice were obtained from Taconic Inc (Germantown, N.Y.). To initiate tumor development, each mouse was inoculated subcutaneously with $3\times10^6$ BT474M 1 cells suspended in Matrigel™. When tumor nodules reached a volume of approximately 100 mm³, animals were randomized to 4 treatment groups. The groups were treated according to Table 3.

TABLE 3

Animal Groups and Doses for Comparison of I.V. Bolus and S.C. Infusion

| Group, Dose, Antibody | Target Serum Conc. µg/ml | Route of Administration | Loading Dose (mg/kg) | Maintenance Dose |
|---|---|---|---|---|
| 1—Control, rhuMAb E25 | 20 | IV LD and SC infusion | 2.20 | 0.250 mg/ml (infusate) |
| 2—Low Dose SC rhuMAb HER2 | 1 | IV LD and SC infusion | 0.313 | 0.050 mg/ml (infusate) |
| 3—High Dose SC rhuMAb HER2 | 20 | IV LD and SC infusion | 6.25 | 1.00 mg/ml (infusate) |
| 4—IV Multi-Dose rhuMAb HER2 | 20 (trough) | IV LD and MD | 4.00 | 2 mg/kg/week (IV bolus) |

Serum Conc. = concentration in serum.
LD = loading dose.
MD = maintenance dose.
Infusate concentration was calculated to achieve targeted serum concentration using Alzet ® osmotic minipumps (Alza Corp., Palo Alto, CA).

Animals were exposed to estrogen by subcutaneous sustained release estrogen pellet 9 days before the start of dosing to promote growth of grafted tumor cells. The animals were inoculated with the BT474M1 cells 8 days before the beginning of treatment and tumors were allowed to grow. The animals were then treated with nonrelevant antibody E25 (non-specific for HER2 receptor, but a member of the monoclonal IgG class) or test antibody HERCEPTIN® anti-ErbB2 antibody as indicated in Table 3. The dosage levels were selected to achieve target serum concentrations of HERCEPTIN®, either 1 µg/ml or 20 µg/ml, by subcutaneous pump infusion or by i.v. bolus delivery. The study groups were treated until day 35. The serum concentration of HERCEPTIN® anti-ErbB2 antibody was measured weekly (just prior to dosing for Group 4) using 3 mice/group/time point. The anti-ErbB2 antibody concentration was determined according to the method disclosed herein involving standard techniques. Tumor volumes were measured two days before dosing began and twice per week from day 6 to day 35 in the study for which data is tabulated below. Tumors were measured in three dimensions and volumes were expressed in $mm^3$. Efficacy was determined by a statistical comparison (ANOVA) of tumor volumes of test animals relative to untreated control animals.

As shown in Table 4, below, treatment of the BT474M1 tumor-bearing mice with HERCEPTIN® anti-ErbB2 antibody by the indicated dosage methods significantly inhibited the growth of the tumors. All HERCEPTIN®-treated groups showed similar inhibition of tumor growth relative to the control group. No dose-response was observed.

The results tabulated above indicate that maintenance of a serum concentration of approximately 2 µg/ml was as effective as a concentration of 20 µg/ml in this study. The results indicated that dosing by subcutaneous infusion was as effective as intravenous bolus dosing and achieved similar trough serum concentrations. The results also indicate that the dose levels studied are at the top of the dose-response curve in this model and that subcutaneous dosing is effective in treating breast cancer tumors. Thus, subcutaneous administration of maintenance doses is feasible as part of a HERCEPTIN® anti-ErbB2 antibody treatment regimen.

Example 4: I.V. Bolus and Subcutaneous Bolus Deliveries of HERCEPTIN® Anti-ErbB2 Antibody Effectively Decrease Tumor Volume in the Mouse Subcutaneous bolus delivery is convenient and cost-effective for the patient and health care professionals. The results of the study disclosed in this example indicate that subcutaneous bolus delivery was as effective as intravenous bolus delivery in reducing breast cell tumor size in a mouse.

This study was set up as disclosed herein in Example 3 for the comparison of intravenous bolus and subcutaneous infusion delivery. A sustained release estrogen implant was inserted subcutaneously one day before tumor cell inoculation as described in Example 3. Six days after tumor cell inoculation, the initial tumor measurement was performed. Seven days after tumor cell inoculation, the first dose of control antibody or HERCEPTIN® anti-ErbB2 antibody was delivered. The animal groups, type of delivery, loading dose and maintenance doses are provided in Table 4. Animals were dosed once weekly for 4 weeks.

TABLE 4

Comparison of S.C. Infusion and I.V. Bolus Delivery

| Treatment Group | Tumor Volume ($mm^3$), Day 35, (n = 14) | Tumor Volume (area under curve) Day 6-Day 35 (n = 13) | HERCEPTIN® Serum Conc. (µg/ml), Day 27, (n = 3) |
|---|---|---|---|
| control s.c. infusion | 764 ± 700 | 5650 ± 4700 | 4.16 ± 1.94 |
| s.c. infusion (low dose) | 80.6 ± 158 | 1610 ± 1250 | 2.11 ± 1.74 |
| s.c. infusion (high dose) | 31 ± 75.6 | 1440 ± 1140 | 22.1 ± 5.43 |
| i.v. bolus dose* | 49.7 ± 95.7 | 2150 ± 1480 | 21.7 ± 17.1** | s.c. = subcutaneous delivery;
i.v. = intravenous delivery.
*4.0 mg/kg Loading Dose and 2.0 mg/kg/week Maintenance Dose.
**at predose (trough serum concentration immediately prior to a maintenance dose)

TABLE 5

Animal Groups and Doses for Comparison of I.V. Bolus and S.C. Bolus Delivery

| Group | Route of Administration | Loading Dose (mg/kg) | Maintenance Dose (mg/kg/week) | n |
|---|---|---|---|---|
| 1—Control rhuMAb E25 | IV | 8 | 4 | 10 |
| 2—rhuMAb HER2 | IV | 2 | 1 | 10 |
| 3—rhuMAb HER2 | IV | 4 | 2 | 10 |
| 4—rhuMAb HER2 | IV | 8 | 4 | 10 |
| 5—rhuMAb HER2 | SC | 4 | 2 | 10 |

IV = intravenous;
SC = subcutaneous;
n = number of animals per group.

The mice were treated according to the information in Table 4 and using the techniques disclosed in Example 3. The serum concentration of HERCEPTIN® anti-ErbB2 antibody was measured weekly before each weekly i.v. maintenance dose according to the procedure described herein and using standard techniques. The control E25 antibody serum concentration was determined according to standard immunoassay techniques. Table 6 shows the increase in HERCEPTIN® anti-ErbB2 antibody serum concentrations with time.

TABLE 6

IV versus SC Bolus Delivery: Serum HERCEPTIN® Anti-ErbB2 Antibody Concentration
Serum Concentration, µg/ml

| Treatment Group (delivery, MD) | Day 0 Mean (SD) | Day 7 Mean (SD) | Day 14 Mean (SD) | Day 21 Mean (SD) |
|---|---|---|---|---|
| 1—Control rhu MAb E25 (IV, 4 mg/kg) | 0 (0) | 25.9 (8.29) | 34.6 (11.2) | 38.5 (14.4) |
| 2—rhu MAb HER2 (IV, 1 mg/kg) | 0 (0) | 4.96 (3.79) | 8.55 (5.83) | 8.05 (4.67) |
| 3—rhu MAb HER2 (IV, 2 mg/kg) | 0 (0) | 13.4 (9.24) | 18.9 (12.0) | 22.6 (9.21) |
| 4—rhu MAb HER2 (IV, 4 mg/kg) | 0 (0) | 29.6 (13.5) | 37.7 (14.4) | 46.2 (13.8) |
| 5—rhu MAb HER2 (SC, 2 mg/kg) | 0 (0) | 12.5 (7.33) | 16.9 (10.2) | 17.6 (10.7) | n = 10 for time points Days 0, 7 and 14.
N = 9 for Day 21.

Table 7 shows the relative efficacy of intravenous bolus delivery and subcutaneous bolus delivery for Groups 1-5 having achieved the serum antibody concentrations presented in Table 6. For this study, efficacy was measured as a decrease in tumor volume. Tumor volume was measured twice weekly.

TABLE 7

Efficacy of HERCEPTIN® Anti-ErbB2 Antibody Measured as a Change in Tumor Volume Comparing Intravenous Bolus and Subcutaneous Bolus Delivery, Mean (SD)

| Treatment Group (Delivery, MD) | Tumor Vol. Day 6, mm$^3$ | Tumor Vol. Day 28, mm$^3$ | Tumor Vol. Day 31, mm$^3$ | Day 6-Day 31* Area Under Curve Tumor Vol., mm$^3$ | Tumor Growth Rate on Log (TM + 1) |
|---|---|---|---|---|---|
| 1—IV Control | 321 (190) | 1530 (1040) | 1630 (1170) | 13600 (7230) | 0.0660 (0.0200) |
| 2—IV Herceptin 1 mg/kg | 297 (130) | 175 (215) | 151 (188) | 4690 (1400) | −0.0505 (0.142) |
| 3—IV Herceptin 2 mg/kg | 269 (129) | 75.7 (92.4) | 73.6 (84.5) | 3510 (1220) | −0.0608 (0.110) |
| 4—IV Herceptin 4 mg/kg | 272 (117) | 25.3 (75.9) | 25.8 (72.9) | 2880 (1230) | −0.0810 (0.0859) |
| 5—SC Herceptin 2 mg/kg | 268 (117) | 76.2 (98.8) | 90.4 (105) | 3230 (1440) | −0.0304 (0.104) |

N = 10 for each data point.
TM = tumor measurement.
IV = intravenous.
SC = subcutaneous.
MD = maintenance dose.
Tumor Vol. = tumor volume, mm$^3$.
*Day 17 excluded due to measurement error.
Tumor growth rate calculated on Day 21-Day 31 Log(TM + 1). Area under the curve is the area beneath a plot of tumor volume versus time.

FIGS. 4A and 4B are graphical plots of changes in tumor volume over time, some of which data is found in Table 7. FIG. 4A is a linear plot of tumor volume versus time. FIG. 4B is a semilogarithmic plot of the same data, allowing the test points be viewed more clearly. The data in Table 7 and FIGS. 4A and 4B indicate that, although a dose-related response was not observed between HERCEPTIN-treated groups, dosing by subcutaneous bolus was as effective as intravenous bolus dosing and achieved similar trough serum concentrations.

Example 5: Regimens for Intravenous and Subcutaneous Delivery of Anti-ErbB2 Antibody According to the invention, methods of anti-ErbB2 antibody (e.g., HERCEPTIN®) delivery comprise greater front loading of the drug to achieve a target serum concentration in approximately 4 weeks or less, preferably 3 weeks or less, more preferably 2 weeks or less, and most preferably 1 week or less, including one day or less. According to the invention, this initial dosing is followed by dosing that maintains the target serum concentration by subsequent doses of equal or smaller amount. An advantage of the methods of the invention is that the maintenance dosing may be less frequent and/or delivered by subcutaneous injection, making the treatment regimens of the invention convenient and cost-effective for the patient and medical professionals administering the antibody. In addition, a subcutaneous maintenance dose regimen may be interrupted by intravenous dosing (such as infusion) when the patient's chemotherapy requires delivery of other drugs by intravenous injection.

To test the following dosage regimens, human subjects are selected according to the criteria disclosed in Example 1, above. The number of initial doses is one or more doses sufficient to achieve an efficacious target serum concentration in approximately 4 weeks or less, preferably 3 weeks or less, more preferably 2 weeks or less, and most preferably 1 week or less, including 1 day or less. The number of maintenance doses may be one or more doses sufficient to achieve suppression of disease symptoms, such as a decrease in tumor volume. The maintenance doses are equal to or smaller than the initial dose or doses, consistent with an object of the invention of administering HERCEPTIN® anti-ErbB2 antibody by regimens providing greater front loading. The specific drug delivery regimens disclosed herein are representative of the invention and are not meant to be limiting.

In one trial, an initial dose of 6 mg/kg, 8 mg/kg, or 12 mg/kg of HERCEPTIN® anti-ErbB2 antibody is delivered to human patients by intravenous or subcutaneous injection. Initial doses (loading doses) are delivered by intravenous infusion or bolus injection or preferably subcutaneous bolus injection. Preferably a target trough serum concentration of HERCEPTIN® anti-ErbB2 antibody of approximately 10-20 µg/m$^1$ is achieved (averaged for all patients in the treatment group) and maintained by subsequent doses of anti-ErbB2 antibody that are equal to or smaller than the initial dose. In one method, a target trough serum concentration is achieved and maintained by once-per-week deliveries of 2 mg/kg HERCEPTIN® anti-ErbB2 antibody by intravenous or subcutaneous injection for at least eight weeks. Alternatively, for this or any dosage regimen disclosed herein, subcutaneous continuous infusion by subcutaneous pump is used to delivery subsequent maintenance doses.

In another method, an initial (front loading) dose of 8 mg/kg HERCEPTIN® anti-ErbB2 antibody is delivered by intravenous injection (infusion or bolus injection) or by subcutaneous bolus injection. This is followed by intravenous bolus injections, intravenous infusion, subcutaneous infusion, or subcutaneous bolus injection of 6 mg/kg at 3-week intervals to maintain a trough serum concentration of approximately 10-20 µg/ml, averaged for an entire treatment group.

In another method, an initial (front loading) dose of 12 mg/kg HERCEPTIN® anti-ErbB2 antibody is delivered by intravenous injection (infusion or bolus injection) or by subcutaneous bolus injection. This is followed by intravenous bolus injections, intravenous infusion, subcutaneous infusion, or subcutaneous bolus injection of 6 mg/kg at 3-week intervals to maintain a trough serum concentration of approximately 10-20 µg/ml.

In yet another method, an initial (front loading) dose of 8 mg/kg HERCEPTIN® anti-ErbB2 antibody is delivered by intravenous infusion or bolus injection, or preferably by subcutaneous bolus injection or infusion. This is followed by administration of 8 mg/kg per week or 8 mg/kg per 2-3 weeks to maintain a trough serum concentration of HERCEPTIN® anti-ErbB2 antibody of approximately 10-20 µg/ml. Maintenance doses are delivered by intravenous infusion or bolus injection, or preferably by subcutaneous infusion or bolus injection.

In another method, the front loading initial dose is a series of intravenous or subcutaneous injections, for example, one on each of days 1, 2, and 3 of at least 1 mg/kg for each injection (where the amount of anti-ErbB2 antibody delivered by the sum of initial injections is more than 4 mg/kg), followed by maintenance doses of 6 mg/kg once each 3 week interval to maintain a target trough serum concentration (for example, approximately 10-20 µg/ml) of HERCEPTIN® anti-ErbB2 antibody. The maintenance doses are delivered by intravenous infusion or bolus injection or by subcutaneous infusion or subcutaneous bolus injection.

In yet another method, the front loading is by intravenous infusion of at least 1 mg/kg, preferably 4 mg/kg on each of five consecutive days, followed by repeats of this cycle a sufficient number of times to achieve suppression of disease symptoms. Following the initial dose or doses, subsequent doses may be delivered by subcutaneous infusion or bolus injection if tolerated by the patient. Such subcutaneous delivery is convenient and cost-effective for the patient and administering health care professionals.

In still another method, HERCEPTIN® anti-ErbB2 antibody is delivered initially as at least 2 intravenous infusions per week for three weeks, followed by repeats of this cycle to maintain an efficacious trough serum concentration of HERCEPTIN® anti-ErbB2 antibody. The dose is at least 4 mg/kg of anti-ErbB2 antibody, preferably at least 5 mg/kg. The maintenance drug deliveries may be intravenous or subcutaneous.

Where the animal or patient tolerates the antibody during and after an initial dose, delivery of subsequent doses may be subcutaneous, thereby providing greater convenience and cost-effectiveness for the patient and health care professionals.

In animal studies, an initial dose of more than 4 mg/kg, preferably more than 5 mg/kg delivered by intravenous or subcutaneous injection, is followed by subcutaneous bolus injections of 2 mg/kg twice per week (separated by 3 days) to maintain a trough serum concentration of approximately 10-20 µg/ml. In addition, where the animal or patient is known to tolerate the antibody, an initial dose of HERCEPTIN® anti-ErbB2 antibody is optionally and preferably deliverable by subcutaneous bolus injection followed by subcutaneous maintenance injections.

While target serum concentrations are disclosed herein for the purpose of comparing animal studies and human trials, target serum concentrations in clinical uses may differ. The disclosure provided herein guides the user in selecting a front loading drug delivery regimen that provides an efficacious target trough serum concentration.

The methods of the invention disclosed herein optionally include the delivery of HERCEPTIN® anti-ErbB2 antibody in combination with a chemotherapeutic agent (other than an anthrocycline derivative) to achieve suppression of disease symptoms. The chemotherapeutic agent may be delivered with HERCEPTIN® anti-ErbB2 antibody or separately and according to a different dosing schedule. For example, subcutaneous delivery of HERCEPTIN® anti-ErbB2 antibody with TAXOL® is included in the invention. In addition, intravenous or subcutaneous injection of 8 mg/kg HERCEPTIN® anti-ErbB2 antibody, followed by intravenous or subcutaneous injection of 6 mg/kg HERCEPTIN® anti-ErbB2 antibody every 3 weeks is administered in combination with a chemotherapeutic agent, such as a taxoid (e.g. paclitaxel 175 mg/m2 every 3 weeks) or an anthracycline derivative (e.g. doxorubicin 60 mg/m2 or epirubicin 75 mg/m2 every 3 weeks). Optionally, where an anthracycline derivative is administered, a cardioprotectant (e.g. 600 mg/m2 cyclophosphamide every 3 weeks) is also administered. In another combination therapy, anti-ErbB2 antibody is administered in a loading dose of more than 4 mg/kg, preferably more than 5 mg/kg, and more preferably at least 8 mg/kg. The loading dose is followed by maintenance doses of at least 2 mg/kg weekly, preferably 6 mg/kg every 3 weeks. The combination therapy includes administration of a taxoid during treatment with anti-ErbB2 antibody. According to one embodiment of the invention, the taxoid is paclitaxel and is administered at a dose of 70-100 mg/m²/week. According to another embodiment of the invention, the taxoid is docetaxel and is administered at a dose of 30-70 mg/m²/week.

Example 6: HERCEPTIN® Administered Intravenously Every Three Weeks in Combination with Paclitaxel Currently, the recommended dose of HERCEPTIN® is 2 mg/kg once weekly. Patients will be administered HERCEPTIN® every three weeks instead of weekly, along with paclitaxel (175 mg/m² every three weeks). Simulation of the proposed treatment regimen suggests that the trough serum concentrations will be 17 mcg/ml, in the range (10-20 mcg/ml) of the targeted trough serum concentrations from previous HERCEPTIN® IV clinical trials. After the first 12 patients the PK parameters will be assessed, if exposure is felt inadequate, then the dose will be increased to 8 mg/kg every three weeks for the remaining 12 patients.

Inclusion Criteria
1) Females ≤18 years of age
2) Histologically confirmed ErbB2 over-expressing metastatic breast cancer
3) Patients who have been newly diagnosed with metastatic disease
4) Have a Karnofsky performance status of ≤70%
5) Give written informed consent prior to any study specific screening procedures with the understanding that the patient has the right to withdraw from the study at any time, without prejudice.

Exclusion Criteria
1) Pregnant or lactating women
2) Women of childbearing potential unless (1) surgically sterile or (2) using adequate measures of contraception such as oral contraceptive, intra-uterine device or barrier method of contraception in conjunction with spermicidal jelly.
3) Clinical or radiologic evidence of CNS metastases.
4) History of any significant cardiac disease
5) LVEF ≤50%
6) No prior taxane therapy in any treatment setting.
7) Any of the following abnormal baseline hematologic values:
  Hb less than 9 g/dl
  WBC less than $3.0 \times 10^9/l$
  Granulocytes less than $1.5 \times 10^9/l$
  Platelets less than $100 \times 10^9/l$
8) Any of the following abnormal baseline liver function tests:
  Serum bilirubin greater than 1.5×ULN (upper normal limit)
  ALT and/or AST greater than 2.5×ULN (greater than 4.0×ULN if liver or bone metastasis)
  Alkaline phosphatase greater than 2.5×ULN (greater than 4.0×ULN if liver or bone metastasis)
9) The following abnormal baseline renal function tests:
  serum creatinine greater than 1.5×ULN
10) History of other serious medical conditions that would preclude patient participation in an investigational study.

HERCEPTIN®
Loading dose and schedule: 8 mg/kg for first dose. Maintenance dose and schedule: 6 mg/kg every 3 weeks.
Paclitaxel—
175 mg/m² IV every 3 weeks×6 cycles as a 3-hour infusion.
NOTE: On the first cycle of treatment, paclitaxel will be dosed 8 hours prior to HERCEPTIN® to determine the PK of paclitaxel alone. HERCEPTIN® will be administered 8 hours post-paclitaxel for the $1^{st}$ cycle only. In subsequent treatment cycles, HERCEPTIN® will be administered prior to paclitaxel.

The total duration of this study is 18 weeks. Study subjects will receive up to 6 total HERCEPTIN® doses. After the last subject has received the last cycle of paclitaxel, data collection for safety and pharmacokinetic analysis will stop, and the study will close to protocol specified treatment. Study subjects may continue to receive the HERCEPTIN®+/−paclitaxel at the discretion of the investigator.

It is believed that the above treatment regimen will be effective in treating metastatic breast cancer, despite the infrequency with which HERCEPTIN® is administered to the patient.

While the particular aspects and embodiments of the invention as herein shown and disclosed in detail is fully capable of obtaining the objects and providing the advantages herein before stated, it is to be understood that it is merely illustrative of some of the presently preferred embodiments of the invention and that no limitations are intended to the details of methods and articles of manufacture shown other than as described in the appended claims. The disclosures of all citations in the specification are expressly incorporated herein by reference.

The invention claimed is:

1. A method for the treatment of a human patient diagnosed with breast cancer characterized by 2+ or 3+ overexpression of ErbB2 receptor as determined by immunohistochemistry or fluorescence in situ hybridization (FISH), comprising the steps of administering to the patient an initial dose of 8 mg/kg of anti-ErbB2 huMAb 4D5-8 antibody; and administering to the patient a plurality of subsequent doses of 6 mg/kg of the antibody, wherein all doses are separated in time from each other by three weeks.

2. The method of claim 1, further comprising administering an effective amount of a chemotherapeutic agent.

3. The method of claim 2, wherein said chemotherapeutic agent is a taxoid.

4. The method of claim 3, wherein said taxoid is paclitaxel or docetaxel.

5. The method of claim 4 wherein said taxoid is paclitaxel.

6. The method of claim 1, wherein said antibody is administered by intravenous injection.

7. A method for the treatment of a human patient diagnosed with breast cancer characterized by 2+ or 3+ overexpression of ErbB2 receptor as determined by immunohistochemistry or fluorescence in situ hybridization (FISH), the method comprising: administering intravenously to the patient an initial dose of 8 mg/kg of anti-ErbB2 huMAb 4D5-8 antibody; and administering intravenously to the patient a plurality of subsequent 6 mg/kg doses of the antibody, wherein the initial dose is separated in time from the first subsequent dose by three weeks, and the subsequent doses are separated from each other in time by three weeks.

8. The method of claim 7, wherein the intravenous administration is an intravenous infusion.

9. The method of claim 8, wherein the subsequent doses maintain a trough serum concentration of the anti-ErbB2 huMAb 4D5-8 antibody at or above 10 µg/mL.

10. The method of claim 8, wherein the subsequent doses maintain a trough serum concentration of the anti-ErbB2 huMAb 4D5-8 antibody at or above 20 µg/mL.

11. The method of claim 7, wherein the subsequent doses maintain a trough serum concentration of the anti-ErbB2 huMAb 4D5-8 antibody at or above 10 µg/mL.

12. The method of claim 7, wherein the subsequent doses maintain a trough serum concentration of the anti-ErbB2 huMAb 4D5-8 antibody at or above 20 µg/mL.

* * * * *